(12) United States Patent
Fujisaki et al.

(10) Patent No.: US 11,446,051 B2
(45) Date of Patent: Sep. 20, 2022

(54) ULTRASONIC VIBRATION TRANSMITTABLE PROBE AND ULTRASONIC TREATMENT ASSEMBLY

(71) Applicant: OLYMPUS CORPORATION, Hachioji (JP)

(72) Inventors: Ken Fujisaki, Sagamihara (JP); Takamitsu Sakamoto, Hachioji (JP); Ken Yokoyama, Fussa (JP); Hideto Yoshimine, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 108 days.

(21) Appl. No.: 16/732,829

(22) Filed: Jan. 2, 2020

(65) Prior Publication Data

US 2020/0138469 A1    May 7, 2020

Related U.S. Application Data

(63) Continuation of application No. PCT/JP2017/024734, filed on Jul. 5, 2017.

(51) Int. Cl.
*A61B 17/32* (2006.01)

(52) U.S. Cl.
CPC ........ *A61B 17/320068* (2013.01); *A61B 17/320016* (2013.01); *A61B 2017/320073* (2017.08); *A61B 2217/007* (2013.01)

(58) Field of Classification Search
CPC .... A61B 17/320068; A61B 17/320016; A61B 2017/320073; A61B 2017/320072; A61B 2017/320077; A61B 2090/062

USPC ................................................ 606/169, 170
See application file for complete search history.

(56) References Cited

U.S. PATENT DOCUMENTS

| 5,989,274 A | 11/1999 | Davison et al. |
| 6,241,703 B1 | 6/2001 | Levin et al. |
| 2005/0090829 A1* | 4/2005 | Martz ............... A61B 17/1604 606/79 |

(Continued)

FOREIGN PATENT DOCUMENTS

| CN | 205964114 U | 2/2017 |
| JP | H05-070515 U | 9/1993 |

(Continued)

OTHER PUBLICATIONS

Nov. 4, 2020 Office Action issued in Japanese Patent Application No. 2019-528271.

(Continued)

*Primary Examiner* — Kathleen S Holwerda
*Assistant Examiner* — Lauren Dubose
(74) *Attorney, Agent, or Firm* — Oliff PLC

(57) ABSTRACT

An ultrasonic vibration transmittable probe includes a probe body configured to transmit ultrasonic vibration generated by an ultrasonic transducer. A treatment section is provided on a distal end side of the probe body along its longitudinal axis and is configured to cut a treatment object with the ultrasonic vibration. The treatment section includes first to third cutting surfaces disposed at progressively proximal positions. A portion of the first cutting surface has a dimension along a first orthogonal direction orthogonal to the longitudinal axis that is smaller than a dimension of the second cutting surface along the first orthogonal direction.

13 Claims, 30 Drawing Sheets

(56) References Cited

U.S. PATENT DOCUMENTS

| | | | |
|---|---|---|---|
| 2006/0004396 A1* | 1/2006 | Easley | A61B 17/1659 606/169 |
| 2006/0253050 A1 | 11/2006 | Yoshimine et al. | |
| 2008/0194999 A1* | 8/2008 | Yamaha | A61B 17/320068 601/2 |
| 2008/0234710 A1* | 9/2008 | Neurohr | A61B 17/320068 606/169 |
| 2010/0121197 A1 | 5/2010 | Ota et al. | |
| 2019/0110799 A1 | 4/2019 | Sun et al. | |

FOREIGN PATENT DOCUMENTS

| | | |
|---|---|---|
| JP | 07-255736 A | 10/1995 |
| JP | H10-5237 A | 1/1998 |
| JP | 2001-502216 A | 2/2001 |
| JP | 2001-079013 A | 3/2001 |
| JP | 2010-207431 A | 9/2010 |
| JP | 2016-041215 A | 3/2016 |
| WO | 2006/030563 A1 | 3/2006 |
| WO | 2016/205335 A1 | 12/2016 |

OTHER PUBLICATIONS

Oct. 10, 2017 International Search Report issued in International Patent Application No. PCT/JP2017/030596.
U.S. Appl. No. 16/713,773, filed Dec. 13, 2019 in the name of Fujisaki et al.
Aug. 29, 2017 International Search Report issued in International Patent Application No. PCT/JP2017/024732.
Aug. 29, 2017 International Search Report issued in International Patent Application No. PCT/JP2017/024733.
Jan. 7, 2020 Translation of International Preliminary Report on Patentability issued in PCT Patent Application No. PCT/JP2017/024732.
Jan. 7, 2020 Translation of International Preliminary Report on Patentability issued in PCT Patent Application No. PCT/JP2017/024733.
Jan. 7, 2020 Translation of International Preliminary Report on Patentability issued in PCT Patent Application No. PCT/JP2017/024734.
Jan. 7, 2020 Translation of International Preliminary Report on Patentability issued in PCT Patent Application No. PCT/JP2017/030596.
U.S. Appl. No. 16/732,879, filed Jan. 2, 2020 in the name of Fujisaki et al.
U.S. Appl. No. 16/732,873, filed Jan. 2, 2020 in the name of Fujisaki et al.
Aug. 29, 2017 International Search Report issued in International Patent Application No. PCT/JP2017/024734.
Nov. 2, 2021 Office Action issued in Japanese Patent Application No. 2020-195401.
Dec. 7, 2021 Office Action issued in U.S. Appl. No. 16/713,773.
May 10, 2022 Office Action issued in U.S. Appl. No. 16/713,773.
May 25, 2022 Office Action issued in Chinese Patent Application No. 201780092912.8.

\* cited by examiner

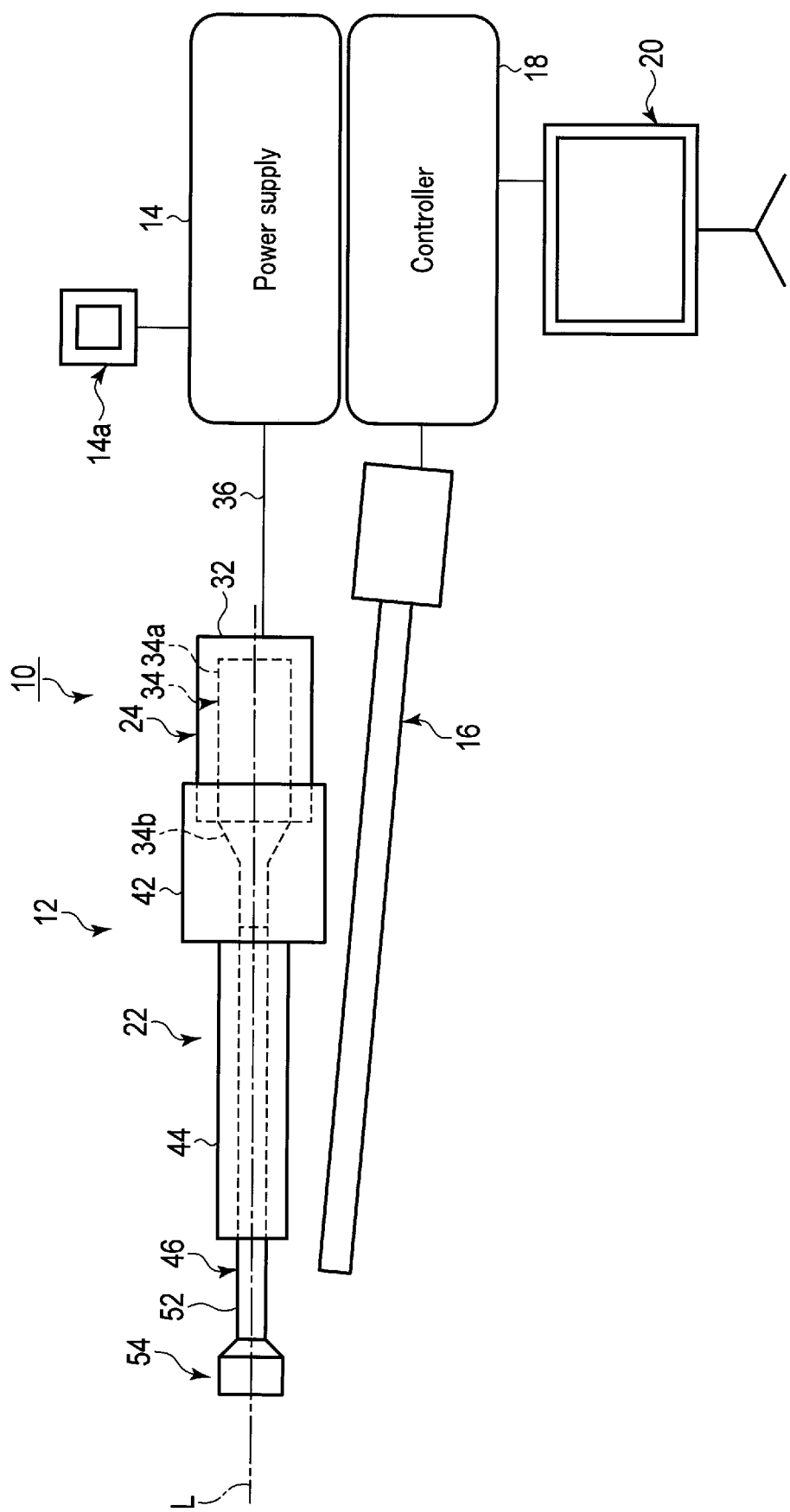
F I G. 1

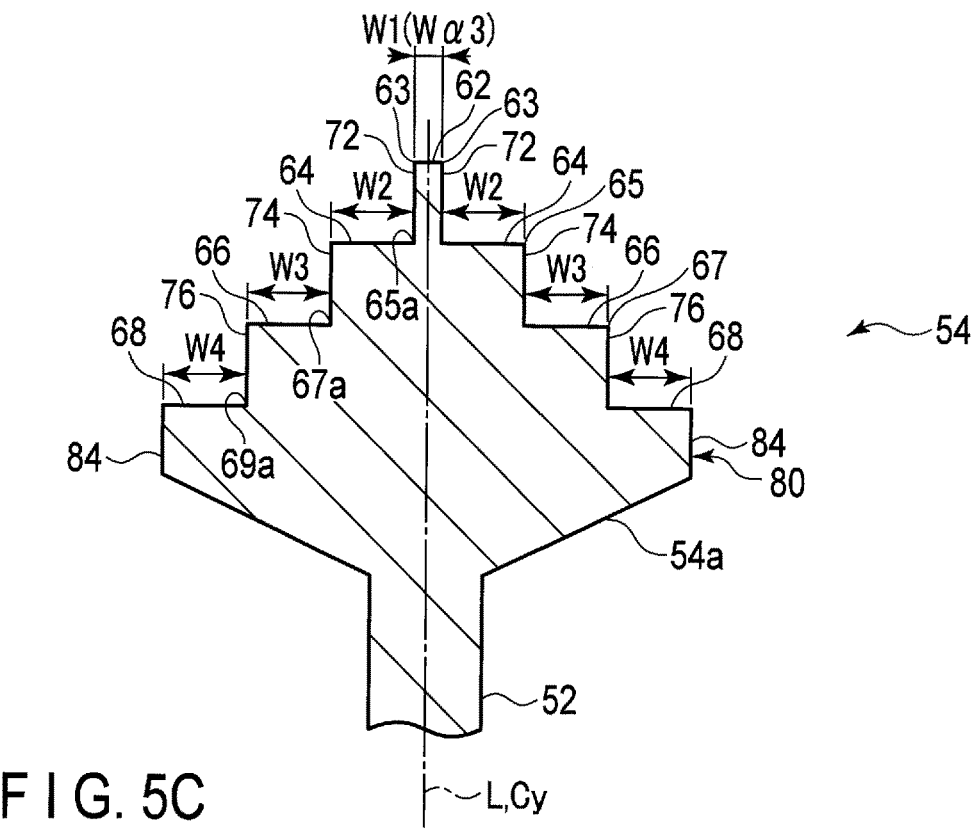
F I G. 5C
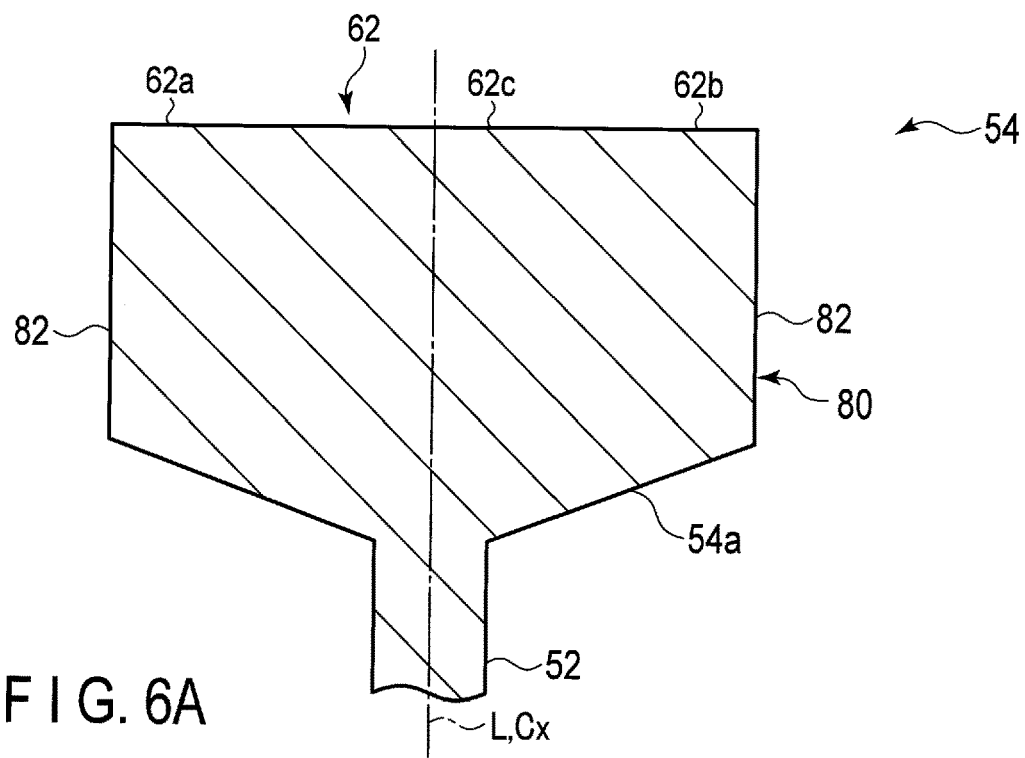
F I G. 6A

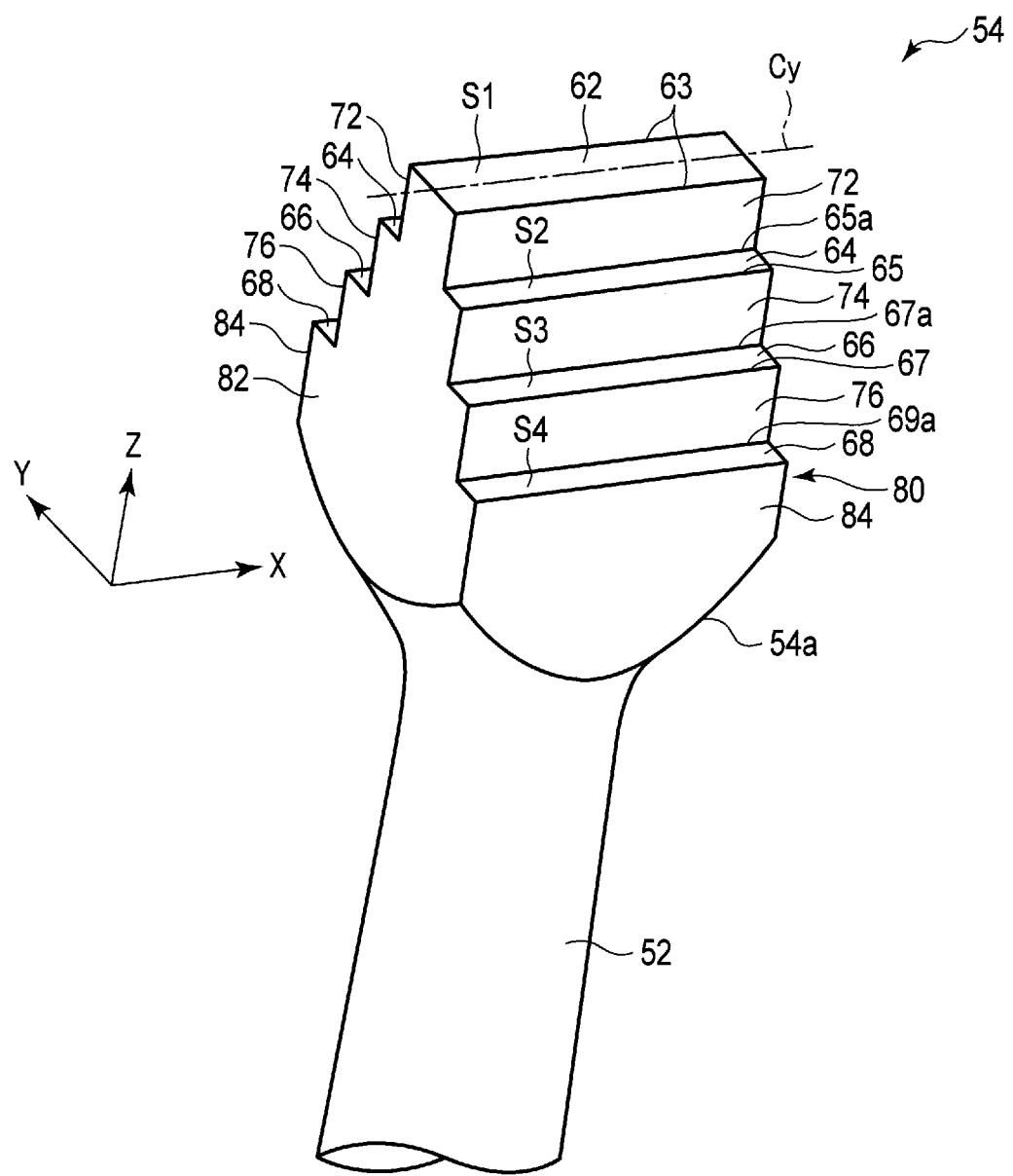
F I G. 10A

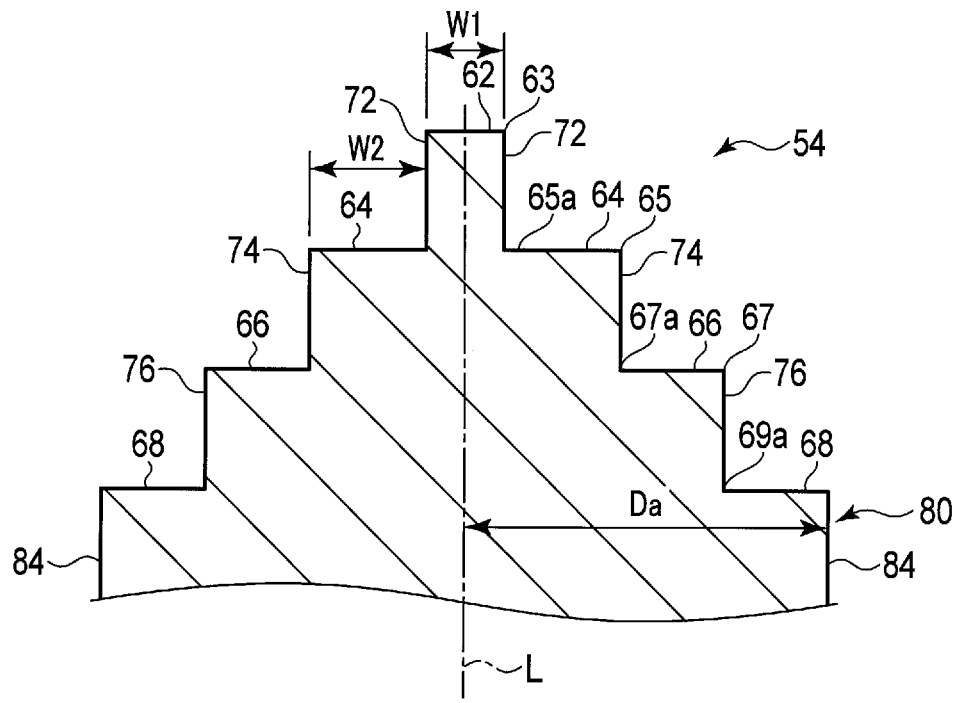
F I G. 11A
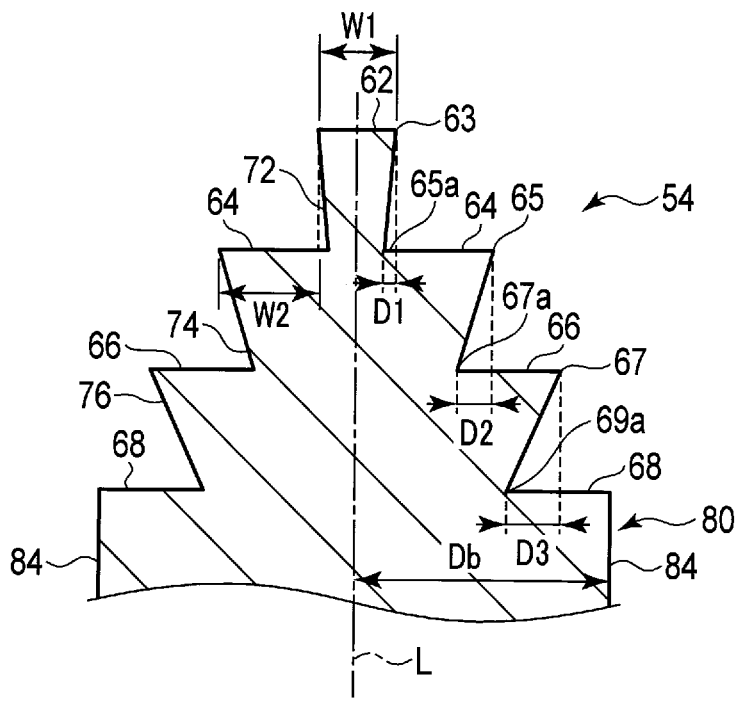
F I G. 11B

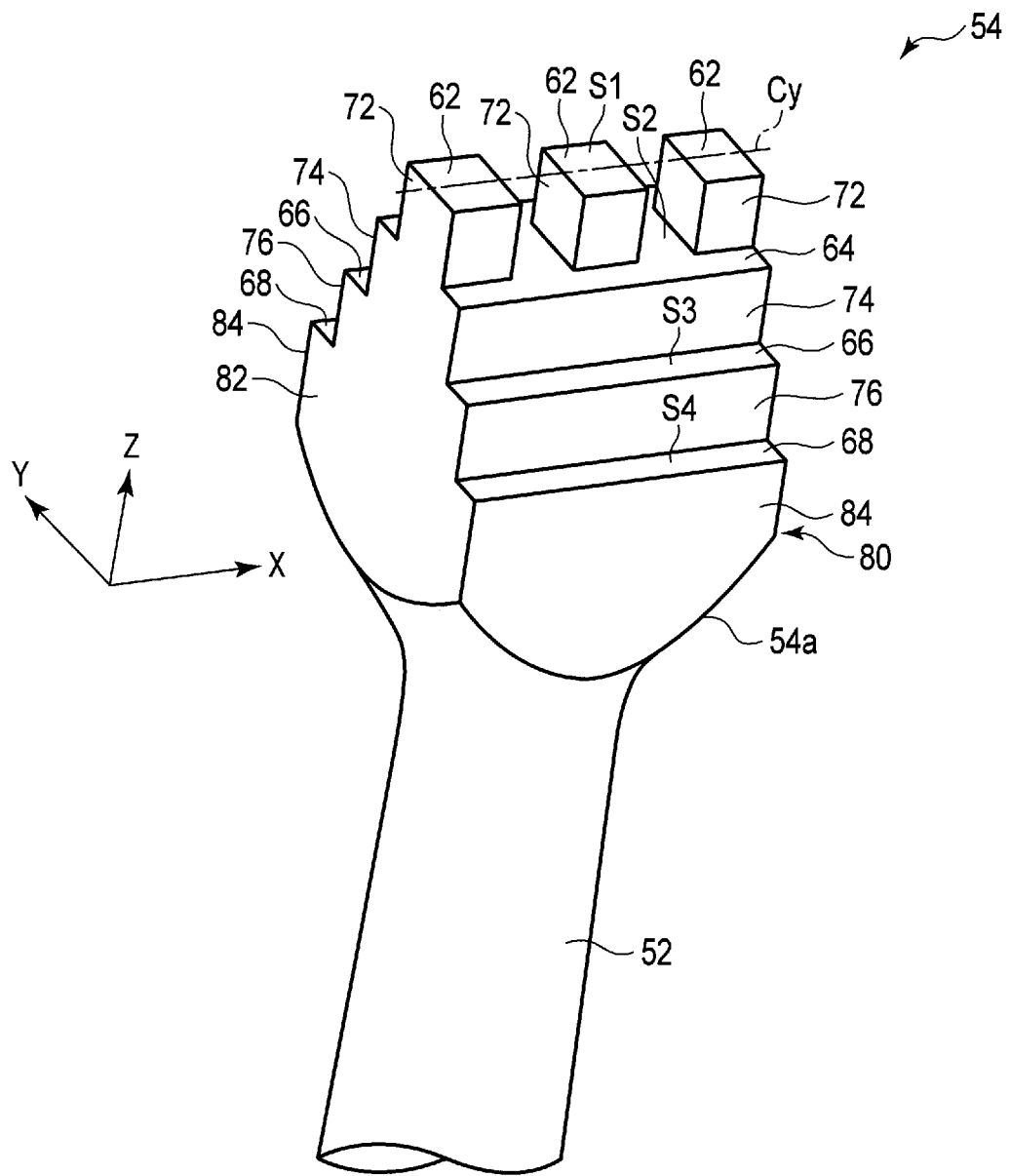
F I G. 13A

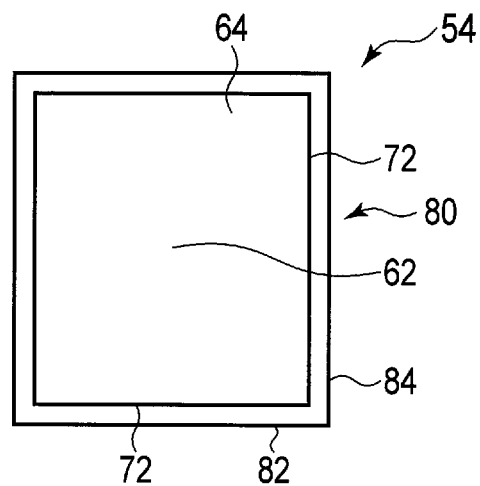
F I G. 16B
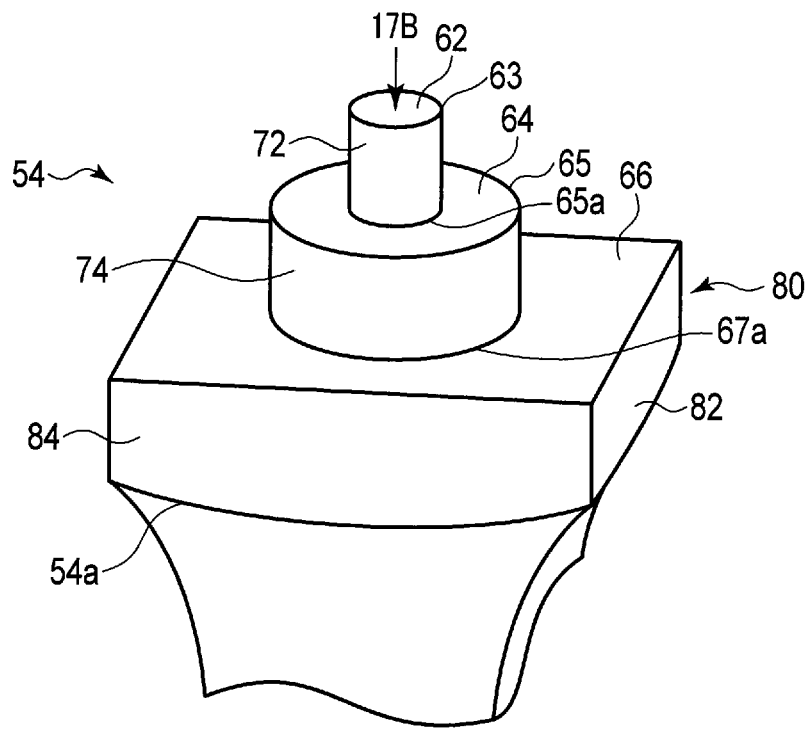
F I G. 17A

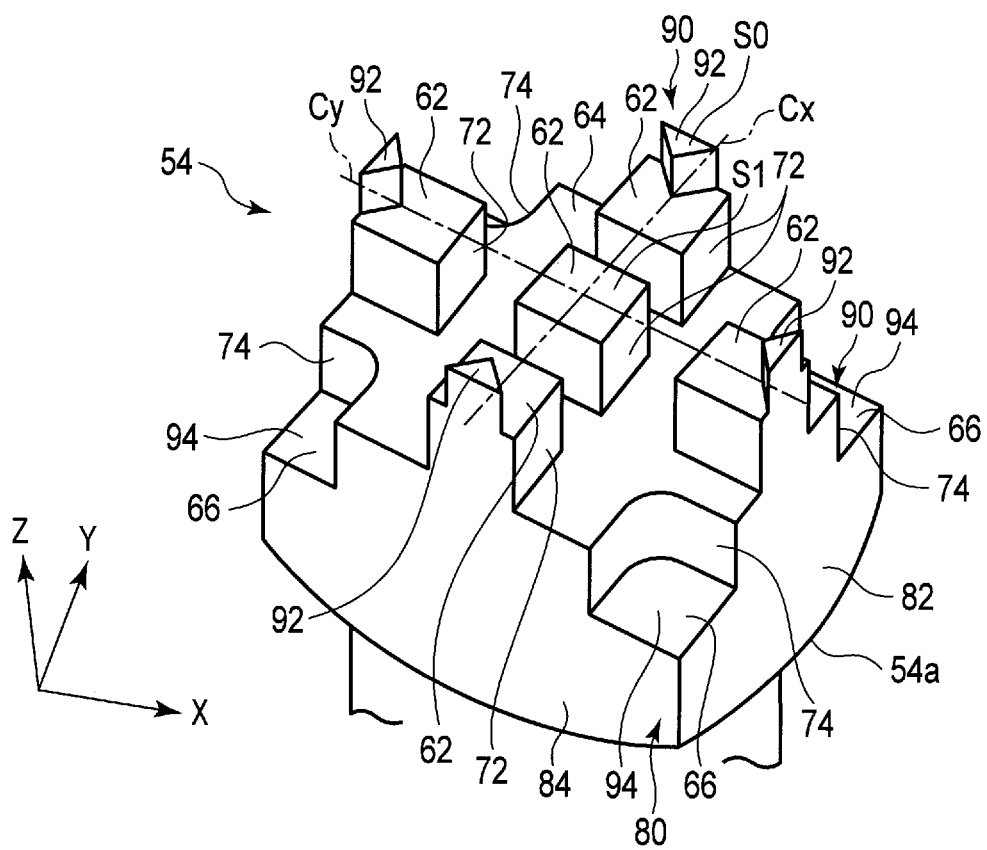
F I G. 19A

ULTRASONIC VIBRATION TRANSMITTABLE PROBE AND ULTRASONIC TREATMENT ASSEMBLY

CROSS-REFERENCE TO RELATED APPLICATIONS

This application is a Continuation Application of PCT Application No. PCT/JP2017/024734, filed Jul. 5, 2017, the entire contents of which are incorporated herein by reference.

BACKGROUND

The present disclosure relates to an ultrasonic vibration transmittable probe and an ultrasonic treatment assembly.

An ultrasonic vibration transmittable probe can be used to form a hole in bone with a distal end when ultrasonic vibration is transmitted. With the ultrasonic vibration transmittable probe, a hole in a shape of a distal end portion is formed.

SUMMARY

According to one aspect of the present disclosure, an ultrasonic vibration transmittable probe includes a probe body that is configured to transmit ultrasonic vibration generated by an ultrasonic transducer. A treatment section is provided on a distal end side of the probe body along its longitudinal axis and configured to cut a treatment object with the ultrasonic vibration. The treatment section includes first to third cutting surfaces disposed at progressively proximal positions. A portion of the first cutting surface has a dimension along a first orthogonal direction orthogonal to the longitudinal axis that is smaller than a dimension of the second cutting surface along the first orthogonal direction.

Advantages will be set forth in the description that follows, and in part will be obvious from the description, or may be learned by practice of the disclosed subject matter. The advantages may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate exemplary embodiments, and together with the general description given above and the detailed description of the embodiments given below, serve to explain the principles of the disclosed subject matter.

FIG. 1 is a schematic view illustrating a treatment system according to exemplary embodiments.

FIG. 5C is a schematic sectional view of a part along line 5C-5C in FIG. 3 and shown by a virtual surface $\alpha 3$ in FIG. 4.

FIG. 6A is a schematic sectional view of a part along line 6A-6A in FIG. 3 and shown by a virtual surface $\beta 1$ in FIG. 4.

FIG. 10A is a schematic perspective view illustrating a treatment section and a vicinity of the treatment section of an ultrasonic vibration transmittable probe according to an exemplary embodiment.

FIG. 11A is an example illustrating a section on an appropriate YX plane in a vicinity of the distal end portion of the treatment section illustrated in FIG. 10A.

FIG. 11B is an example illustrating a section on an appropriate YX plane in the vicinity of the distal end portion of the treatment section illustrated in FIG. 10A, and different from FIG. 11A.

FIG. 13A is a schematic perspective view illustrating a treatment section and a vicinity of the treatment section of an ultrasonic vibration transmittable probe according to an exemplary embodiment.

FIG. 16B is a schematic view of the treatment section of the ultrasonic vibration transmittable probe seen from a direction shown by an arrow 16B in FIG. 16A.

FIG. 17A is a schematic perspective view illustrating a treatment section and a vicinity of the treatment section of an ultrasonic vibration transmittable probe according to an exemplary embodiment.

FIG. 19A is a schematic perspective view illustrating a treatment section and a vicinity of the treatment section of an ultrasonic vibration transmittable probe according to an exemplary embodiment.

DETAILED DESCRIPTION

Figure 2:
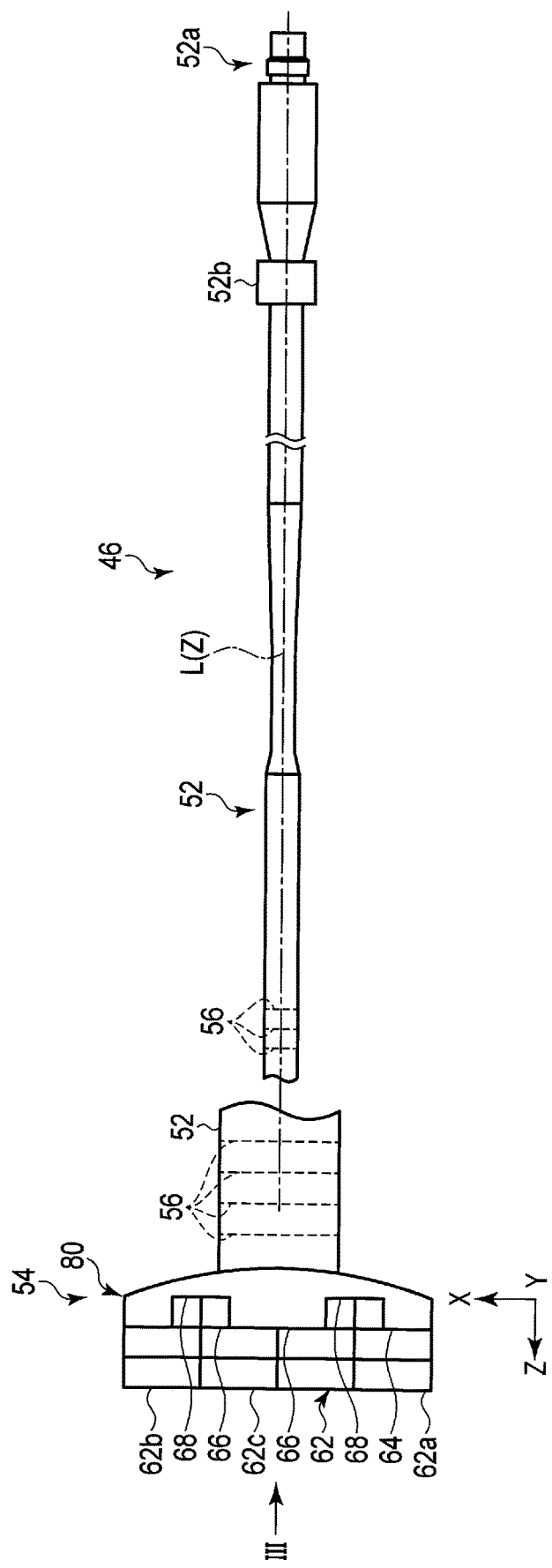
FIG. 2 is a schematic view illustrating an ultrasonic vibration transmittable probe of the treatment system according to an exemplary embodiment, and particularly enlarging and illustrating a treatment section and a vicinity of the treatment section.

Hereinafter, modes for carrying out the disclosed subject matter will be described with reference to the drawings.

An exemplary embodiment will be described with reference to FIG. 1 to FIG. 9E.

As illustrated in FIG. 1, a treatment system 10 according to the embodiment includes an ultrasonic treatment assembly 12, a power supply (first controller) 14, an arthroscope (endoscope) 16, a controller (second controller) 18, and a display 20. The treatment system 10 is preferably used with an irrigation device not illustrated. Accordingly, when treatment using the treatment system 10 is performed, it is possible to circulate irrigating fluid while charging the irrigating fluid inside a joint cavity 110a of a knee joint 110, for example. The ultrasonic treatment assembly 12 and the arthroscope 16 of the treatment system 10 can be used in treatment in the joint cavity 110a filled with the perfusate.

The arthroscope 16 observes, for example, an inside of the knee joint 110, that is, an inside of the joint cavity 110a of a patient. The controller 18 takes in an image obtained by the arthroscope 16, and performs image processing. The display 20 shows video generated by the image processing in the controller 18. Note that in a so-called open surgery such as a case of performing treatment while directly observing a treatment object part visually, for example, the arthroscope (endoscope) 16 in the treatment system 10 is not always necessary.

The ultrasonic treatment assembly 12 includes a treatment instrument 22, and an ultrasonic transducer 24. The treatment instrument 22 and the ultrasonic transducer 24 are placed on a common longitudinal axis (center axis) L. In particular, an ultrasonic vibration transmittable probe 46 and a vibrating body 34 that will be described later are placed on the common longitudinal axis (center axis) L.

The ultrasonic transducer 24 includes a housing (transducer case) 32, and the vibrating body 34 placed inside of the housing 32. The vibrating body 34 includes a bolt-clamped Langevin-type ultrasonic transducer 34a, and a connection section 34b with a proximal end of the ultrasonic vibration transmittable probe 46 that will be described later. The connection section 34b is formed at a distal end of the transducer 34*a*. The connection section 34*b* preferably protrudes to a distal end side of the housing 32 along the longitudinal axis (center axis) L of the ultrasonic transducer 24. From a proximal end of the housing 32 of the ultrasonic transducer 24, a cable 36 having one end connected to the transducer 34*a*, and the other end connected to the power supply 14 is extended.

When power from the power supply 14 is supplied to the transducer 34*a* of the ultrasonic transducer 24, the transducer 34*a* generates longitudinal vibration of an appropriate amplitude along the longitudinal axis L. The ultrasonic transducer 24 appropriately enlarges the amplitude of the ultrasonic vibration generated by the ultrasonic transducer 34*a* by a shape (horn shape) of the connection section 34*b* on a distal end side along the longitudinal axis L. The ultrasonic transducer 24 inputs the ultrasonic vibration to the proximal end of the ultrasonic vibration transmittable probe 46 along the longitudinal axis L and transmits the ultrasonic vibration to a treatment section 54 that will be described later.

A switch 14*a* is connected to the power supply 14. The power supply 14 supplies appropriate energy (power) to the ultrasonic transducer 24 in response to an operation of the switch 14*a*, and causes the ultrasonic transducer 34*a* to generate ultrasonic vibration. For example, the switch 14*a* keeps a state where the ultrasonic transducer 34*a* is driven when the switch 14*a* is in a state of being pressed and operated, and the state where the ultrasonic transducer 34*a* is driven is released when pressure is released. Note that the switch 14*a* is also preferably provided at a handle 42 described later.

The treatment instrument 22 includes the handle 42, a sheath 44 and the ultrasonic vibration transmittable probe 46. As illustrated in FIG. 2, the ultrasonic vibration transmittable probe 46 integrally includes a probe body 52 and the block-shaped treatment section 54. In FIG. 2, the treatment section 54 and a vicinity of the treatment section 54 are enlarged. The treatment section 54 includes, at a proximal end of the treatment section 54, an inclined surface 54*a* that is more gradual than being orthogonal to the longitudinal axis L. The inclined surface 54*a* is formed at a proximal end portion closer to a proximal end side than an outermost edge 80 of the treatment section 54. Accordingly, the proximal end portion of the treatment section 54 forms a sectional area of a cross section orthogonal to the longitudinal axis L to be smaller toward the proximal end side along the longitudinal axis L. Accordingly, the inclined surface 54*a* decreases in diameter toward the proximal end side from the distal end side along the longitudinal axis L. The inclined surface 54*a* smoothly connects a distal end of the probe body 52 and the treatment section 54. Existence of the inclined surface 54*a* shortens lengths along the longitudinal axis L, of end surfaces 82 and 84 forming the outermost edge 80 which will be described later of the treatment section 54, and makes it easy for crushed debris of bone B or the like to be discharged to the proximal end side along the longitudinal axis L.

A scale 56 indicating a distance from the distal end of the treatment section 54 is formed in a vicinity of a distal end portion of the probe body 52. The scale 56 is observable with the arthroscope 16.

The ultrasonic vibration transmittable probe 46 is formed from a material capable of transmitting ultrasonic vibration from the proximal end to the distal end along the longitudinal axis L, such as a metal material like a titanium alloy, for example. The ultrasonic vibration transmittable probe 46 is preferably formed straight. The proximal end of the probe body 52 includes a connection section (ultrasonic transducer connection section) 52*a* that is connected to the connection section 34*b* of the vibrating body 34 of the ultrasonic transducer 24. Consequently, the connection section 34*b* of the ultrasonic transducer 24 fixed to the housing 32 is fixed to the connection section 52*a* at the proximal end of the probe body 52. Accordingly, the ultrasonic transducer 24 is provided on the proximal end side along the longitudinal axis L, of the probe 46.

The probe body 52 transmits the ultrasonic vibration of longitudinal vibration generated by the ultrasonic transducer 24 from the proximal end side to the distal end side along the longitudinal axis L. The ultrasonic vibration generated by the ultrasonic transducer 34*a* is transmitted to the treatment section 54 via the connection section 34*b* and the probe body 52. The treatment section 54 is provided on the distal end side of the probe body 52 along the longitudinal axis L, and cuts a treatment object with the transmitted ultrasonic vibration. The treatment section 54 is capable of forming a hole in bone that is a treatment object with the ultrasonic vibration. The ultrasonic transducer 34*a* to the distal end of the treatment section 54 is on the straight longitudinal axis L (center axis). Consequently, longitudinal vibration is transmitted to the treatment section 54.

A total length of the probe 46 is preferably an integral multiple of one-half wavelength based on a resonance frequency of the transducer 34*a*, for example. The total length of the probe 46 is not limited to an integral multiple of one-half wavelength based on the resonance frequency of the transducer 34*a*, but is appropriately adjusted according to a material, an amplitude magnification and the like. Accordingly, the total length of the probe 46 may be a substantially integral multiple of a one-half wavelength based on the resonance frequency of the transducer 34*a*. The vibrating body 34 and the probe 46 have materials, and shapes including lengths and diameters set appropriately so as to vibrate with a frequency in the resonance frequency of the transducer 34*a* and an output of the power supply 14, as a whole.

The connection section 34*b* at the distal end of the vibrating body 34 and the proximal end of the vibrating body 34 are at anti-nodes of the vibration. Of the ultrasonic vibration transmittable probe 46, a proximal end which is connected to the connection section 34*b* of the vibrating body 34 is at an anti-node of the vibration, and the treatment section 54 is at an anti-node of the vibration. On an outer circumferential surface of the probe body 52 of the probe 46, a spacer not illustrated is provided between the outer circumferential surface and an inner circumferential surface of the sheath 44. The spacer is provided on an outer periphery in a position of a node of the vibration that does not move along the longitudinal axis L. Further, with respect to the handle 42, the probe body 52 is supported on an outer periphery in a position of a node of the vibration denoted by reference sign 52*b*.

Figure 3:
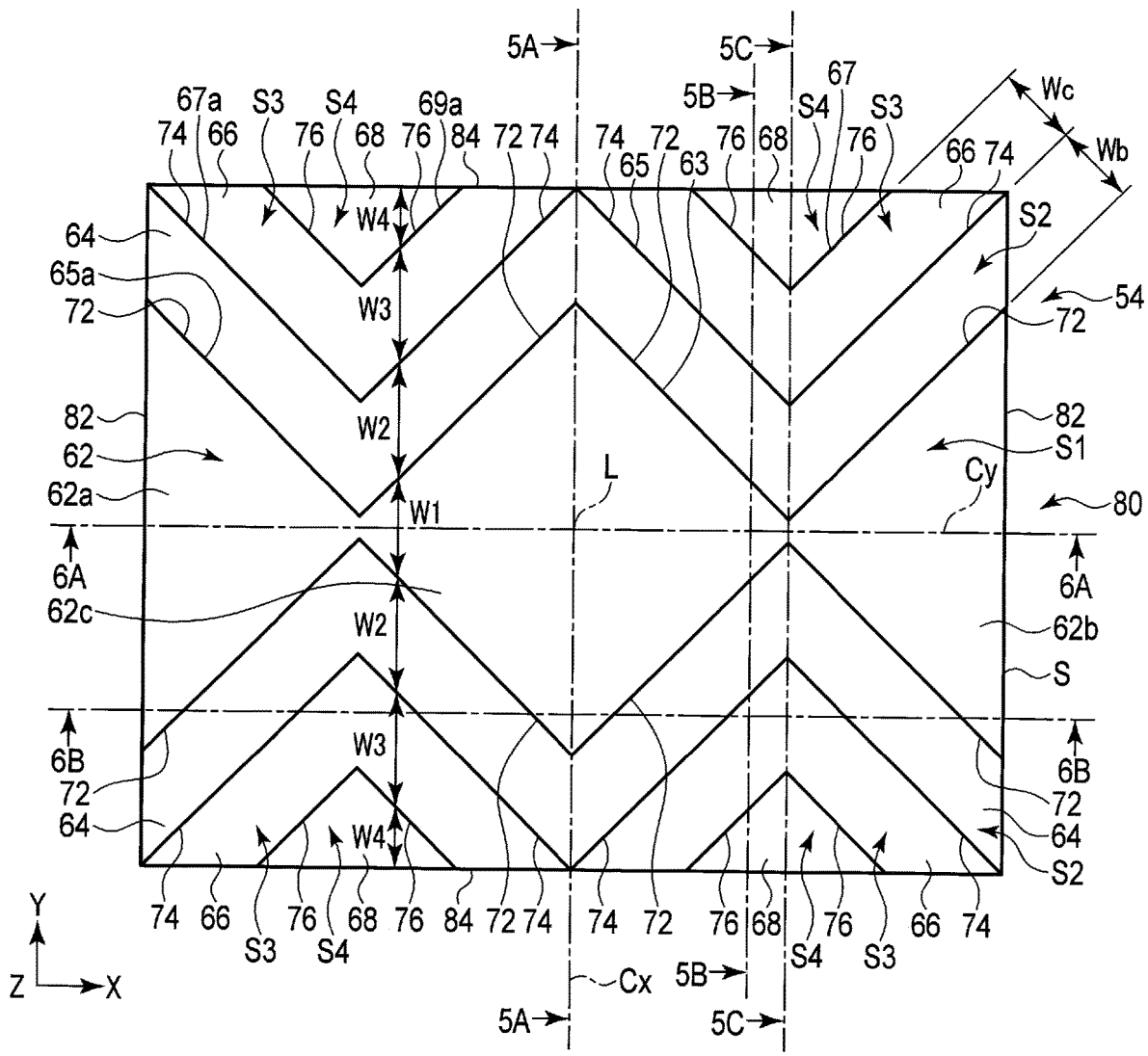
FIG. 3 is a schematic view of the treatment section of the ultrasonic vibration transmittable probe seen from a direction of an arrow III in FIG. 2.

In the treatment section 54, a projection shape (outermost edge) 80 at a time of the proximal end side being seen from the distal end side along the longitudinal axis L of the treatment section 54 is formed into a multangular shape such as a rectangular shape illustrated in FIG. 3. In the treatment section 54 of the treatment instrument 22 according to the present embodiment, the outermost edge 80 is formed into a rectangular shape (oblong shape) when the proximal end side is seen from the distal end side along the longitudinal axis L. The outermost edge 80 of the treatment section 54 defines an outer shape of a bone hole (tunnel) 100 that will be described later. The outermost edge 80 includes a pair of end surfaces 82 that form short sides, and a pair of end surfaces 84 that form long sides. The outermost edge 80 has a short side of 4 mm and a long side of 5 mm, as an example. Note that as described later with respect to FIG. 15A, the outermost edge 80 may be in a regular polygon. A shape of the outermost edge 80 can be appropriately formed according to a shape of a hole desired to be formed by one or a plurality of treatments.

Here, a direction (long side direction) along the long side of the outermost edge 80 is set as an X-axis, and a direction (short side direction) along the short side is set as a Y-axis. The X-axis is in a first orthogonal direction to the longitudinal axis L. The Y-axis is in a second orthogonal direction to the longitudinal axis L. The first orthogonal direction and the second orthogonal direction are orthogonal to each other. Note that a direction along the longitudinal axis L is set as a Z-axis. In other words, an XYZ coordinates system to the probe 46 is defined as described above.

A central line Cx is taken in a center of a pair of end surfaces 82 that form the short sides, and a central line Cy is taken in a center of a pair of end surfaces 84 that form the long sides. The central line Cx is parallel to the Y-axis. The central line Cy is parallel to the X-axis. The treatment section 54 according to the present embodiment is formed symmetrically about the central line Cx, and is formed symmetrically about the central line Cy. In the present embodiment, a first surface (first cutting surface) 62, a second surface (second cutting surface) 64, a third surface (third cutting surface) 66 and a fourth surface (fourth cutting surface) 68 are formed symmetrically with respect to a virtual surface (ZX plane) formed by the longitudinal axis L and the central line Cx. In the present embodiment, the first surface 62, the second surface 64, the third surface 66 and the fourth surface 68 are formed symmetrically with respect to a virtual surface (YZ plane) including the longitudinal axis L and the central line Cy.

The outermost edge 80 is preferably formed symmetrically with respect to the virtual surface (YZ plane) formed by the longitudinal axis L and the central line Cx. The outermost edge 80 is preferably formed symmetrically with respect to the virtual surface (ZX plane) formed by the longitudinal axis L and the central line Cy.

Figure 4:
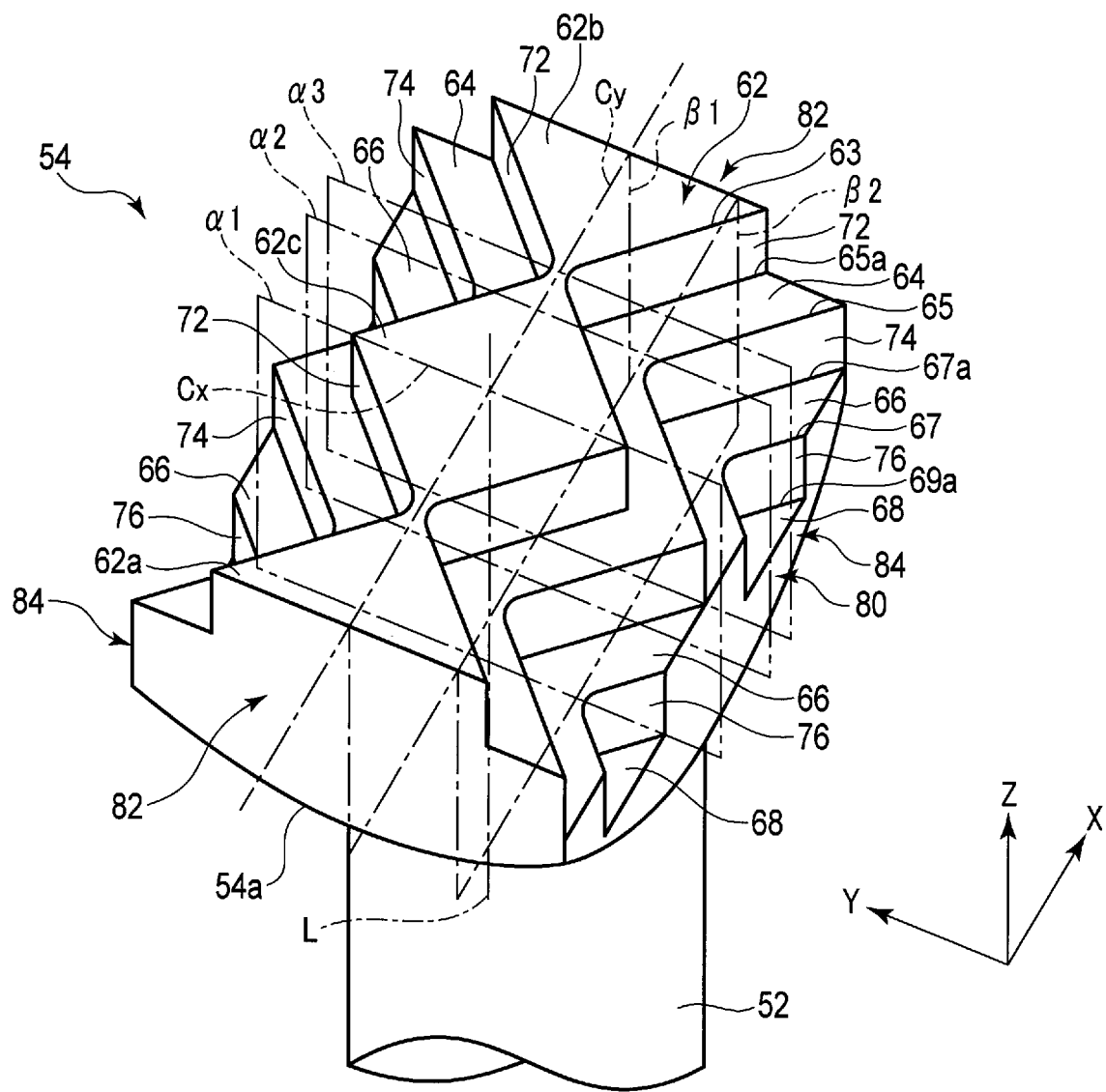
FIG. 4 is a schematic perspective view of the treatment section of the ultrasonic vibration transmittable probe illustrated in FIG. 2.

As illustrated in FIG. 3 and FIG. 4, the treatment section 54 is formed in a step shape. The treatment section 54 protrudes to the distal end side from the proximal end side along the longitudinal axis L. The treatment section 54 includes the first surface 62, a pair of second surfaces 64, two pairs of third surfaces 66, and two pairs of fourth surfaces 68, in an order from the distal end side to the proximal end side along the longitudinal axis L. The first surface 62, the pair of second surfaces 64, the two pairs of third surfaces 66, and the two pairs of fourth surfaces 68 are provided closer to the distal end side along the longitudinal axis L than a portion forming the outermost edge 80. In the treatment section 54, the fourth surfaces 68, the third surfaces 66, the second surfaces 64 and the first surface 62 are formed in the step shape that rises toward the distal end side from the proximal end side along the longitudinal axis L. The first surface 62 is formed as a distal end surface of the treatment section 54. The first surface 62, the second surfaces 64, the third surfaces 66 and the fourth surfaces 68 are preferably formed as planes orthogonal to the longitudinal axis L respectively. In other words, the first surface 62, the second surfaces 64, the third surfaces 66 and the fourth surfaces 68 are preferably parallel to the XY plane formed by the X-axis and the Y-axis, respectively.

Note that the first surface 62, the second surfaces 64, the third surfaces 66 and the fourth surfaces 68 are described as parallel to the XY plane respectively, but may be approximately parallel with a slight inclination, in a range of several degrees 0, for example, with respect to the XY plane. In other words, the first surface 62, the second surfaces 64, the third surfaces 66 and the fourth surfaces 68 are allowed to be in a state of being approximately orthogonal without being orthogonal to the longitudinal axis L.

The first surface 62, the second surface 64, the third surface 66 and the fourth surface 68 are all preferably formed as planes. In the first surface 62, a concave portion and/or a convex portion may be formed in a vicinity of a region shown by the central line Cy described later, for example, as long as a region including a first edge portion (outer edge) 63 is formed as a plane. Likewise, in the second surface 64, a concave portion and/or a convex portion may be formed in a vicinity of a region close to a first side surface 72 that will be described later, as long as a region including a second edge portion (outer edge) 65 and an inner edge 65a is formed as a plane. Further, in the third surface 66, a concave and a convexity may be formed in a vicinity of a region close to a second side surface 74 described later as long as a region including a third edge portion (outer edge) 67 and an inner edge 67a is formed as a plane. In the fourth surface 68, a concave portion and/or a convex portion may be formed in a vicinity of a region close to a third side surface 76 that will be described later as long as a region including a fourth edge portion (outer edge) 69 and an inner edge 69a is formed as a plane. In particular, the region including the first edge portion (outer edge) 63 of the first surface 62, the region including the second edge portion (outer edge) 65 of the second surface 64, the region including the third edge portion (outer edge) 67 of the third surface 66, and the region including the fourth edge portion (outer edge) 69 of the fourth surface 68 are preferably formed as planes orthogonal to the longitudinal axis L.

Note that a projection shape (inside of the outer edge 63 of the first surface 62) at a time of the first surface 62 being seen from a distal end side to a proximal end side along the longitudinal axis L is smaller than a projection shape (inside of the outer edge 65 of the second surface 64) at a time of the second surface 64 being seen from the distal end side to the proximal end side along the longitudinal axis L. Consequently, the projection shape of the first surface 62 is inside of the outer edge 65 of the second surface 64, is inside of the outer edge 67 of the third surface 66, and is inside of the outer edge (outermost edge 80) of the fourth surface 68.

The first surface 62 includes right-angled isosceles triangular surfaces 62a and 62b adjacent to the end surface 82 in the X-axis direction, and a substantially square surface 62c between the surfaces 62a and 62b. In the first surface 62, the surface 62a, the surface 62c and the surface 62b continue along the X-axis direction. The first surface 62 is formed on the central line Cy in a substantially center between one end and the other end in the Y-axis direction. A virtual longitudinal axis (center axis) L penetrates through the surface 62c in the substantially square shape.

The pair of second surfaces 64 are formed in positions deviated toward both end sides (end surfaces 84) in the Y-axis direction from the central line Cy. The second surfaces 64 are respectively formed in positions close to both end sides in the Y-axis direction with respect to the first surface 62, and in positions close to the probe body 52 along the Z-axis direction with respect to the first surface 62. The second surfaces 64 are each formed in a substantially M-shape or in a substantially W-shape.

The four first side surfaces 72 each in a substantially rectangular shape are formed between the outer edge (first edge portion) 63 of the first surface 62 and one of the pair of second surfaces 64, and the four first side surfaces 72 are formed between the outer edge 63 of the first surface 62 and the other one of the pair of second surfaces 64, respectively. The first side surfaces 72 are each parallel to the Z-axis. The first side surface (step) 72 continues to the first surface 62 and the second surface 64.

Of the outermost edge 80 in the substantially rectangular shape that defines an outer shape of the bone socket 100, a pair of end surfaces 82 that form short sides are formed as end surfaces of the first surface 62 and the second surface 64 with the first side surfaces 72.

The third surfaces 66 are formed in positions that are more deviated toward both end sides (end surfaces 84) in the Y-axis direction from the central line Cy than the second surfaces 64. The third surfaces 66 are respectively formed in positions close to both the end sides in the Y-axis direction with respect to the second surfaces 64, and in positions close to the probe body 52 along the Z-axis direction with respect to the second surfaces 64. The third surfaces 66 are each formed in a substantially V-shape.

Four second side surfaces 74 each in a substantially rectangular shape are formed between the outer edge (second edge portion) 65 of one of the second surfaces 64 and a pair of third surfaces 66. The four second side surfaces 74 each in a substantially rectangular shape are formed between the other second surface 64 and a pair of third surfaces 66. The second side surfaces 74 are respectively parallel to the Z-axis.

The fourth surfaces 68 are formed in positions more deviated toward both the end sides (end surfaces 84) in the Y-axis direction from the central line Cy than the third surfaces 66. The fourth surfaces 68 are respectively formed in positions close to both the end sides in the Y-axis direction with respect to the third surface 66, and in positions close to the probe body 52 along the Z-axis direction with respect to the third surfaces 66. The fourth surfaces 68 are each formed in a substantially triangular shape.

Note that of the outermost edge 80 in the substantially rectangular shape that defines the outer shape of the bone socket 100, the long sides are formed by the third surfaces 66 and the fourth surfaces 68.

Between one of the four third surfaces 66 and one of the fourth surfaces 68, two third side surfaces 76 each in a substantially rectangular shape are formed. The third side surfaces 76 are respectively parallel to the Z-axis.

Accordingly, when the treatment section 54 is seen from the distal end side to the proximal end side along the longitudinal axis L, not only the first surface 62, but also all surfaces of the second surfaces 64, the third surfaces 66 and the fourth surfaces 68 are exposed to be recognized.

Figure 5A:
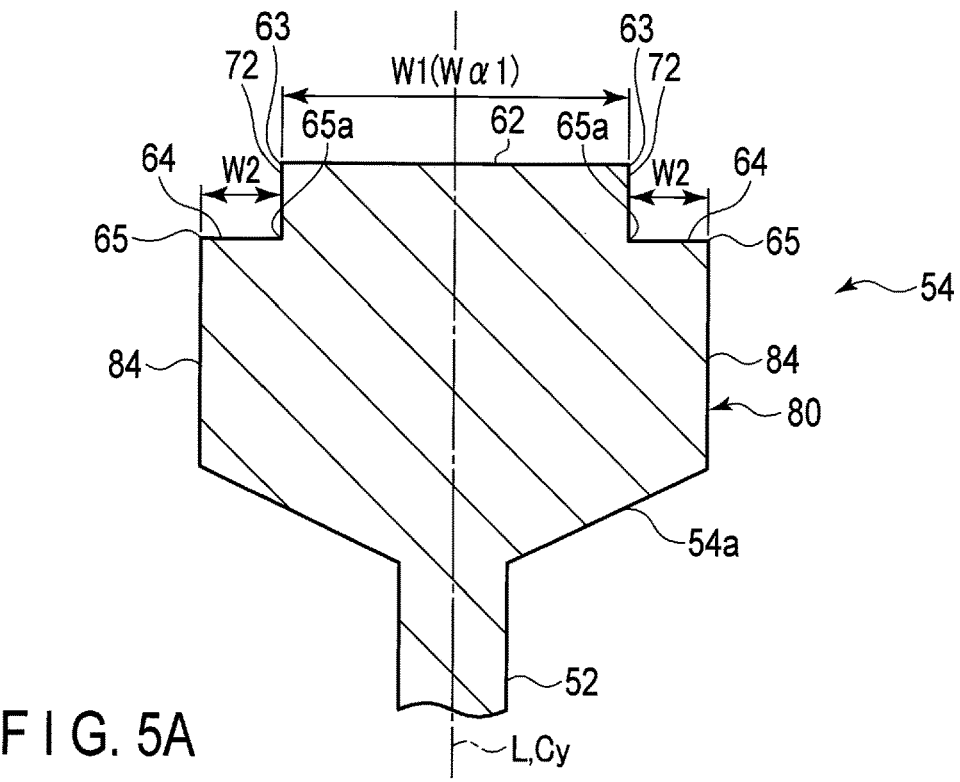
FIG. 5A is a schematic sectional view of a part along line 5A-5A in FIG. 3 and shown by a virtual surface $\alpha 1$ in FIG. 4.
Figure 5B:
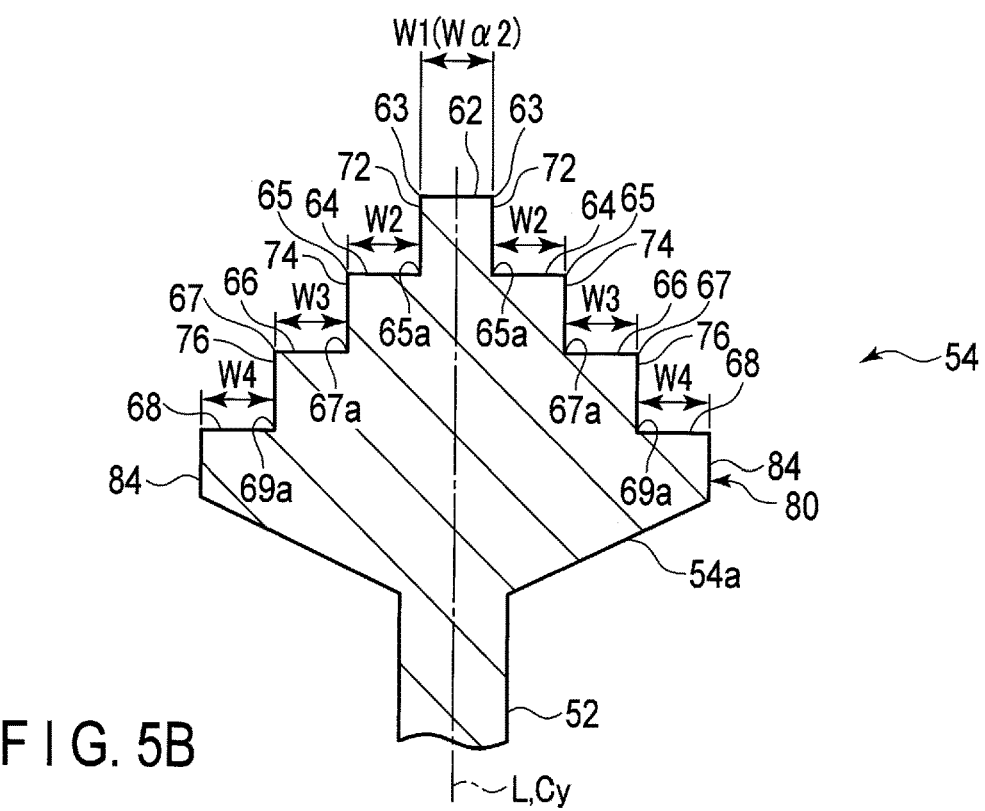
FIG. 5B is a schematic sectional view of a part along line 5B-5B in FIG. 3 and shown by a virtual surface $\alpha 2$ in FIG. 4.
Figure 6B:
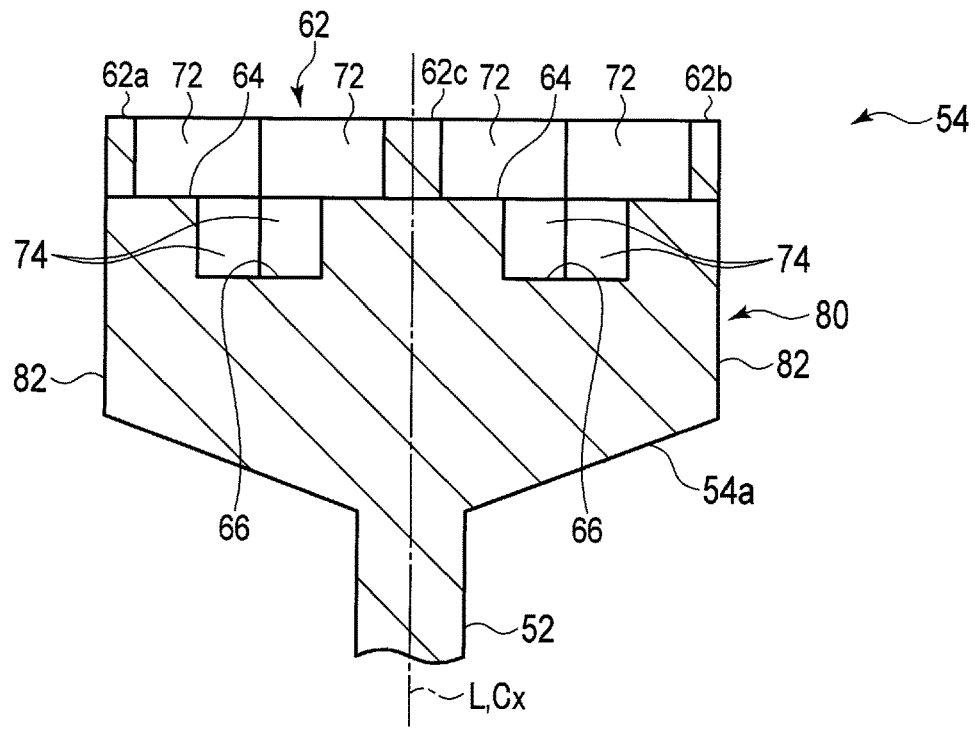
FIG. 6B is a schematic sectional view of a part along line 6B-6B in FIG. 3 and shown by a virtual surface $\beta 2$ in FIG. 4.

FIG. 5A to FIG. 5C illustrate sections of surfaces that are parallel to the central line Cx in FIG. 3 and FIG. 4 and orthogonal to the central line Cy, that is, parallel to the YZ plane. FIG. 6A and FIG. 6B illustrate sections of surfaces that are orthogonal to the central line Cx in FIG. 3 and FIG. 4, and parallel to the central line Cy, that is, parallel to the ZX plane.

An edge between the first edge portion 63 of the first surface 62 and the first side surface 72 is preferably formed as sharp as possible at a right angle. In this case, the concave bone socket 100 of an outer shape of the first surface 62 is easily formed. An edge between the second edge portion 65 of the second surface 64 and the second side surface 74 is preferably formed as sharp as possible at a right angle. In this case, the concave bone socket 100 in the outer shape of the second surface 64 is easily formed. Likewise, an edge between the third edge portion 67 of the third surface 66 and the third side surface 76, and an edge between the fourth edge portion 69 of the fourth surface 68 and the outermost edge 80 are as sharp as possible at a right angle. In these cases, the concave bone socket 100 in the outer shape of the third surface 66 is easily formed, and the concave bone socket 100 in the outer shape of the fourth surface 68 is easily formed.

Of the outermost edge 80 in the substantially rectangular shape that defines the outer shape of the bone socket 100, the pair of end surfaces 84 that form the long sides are formed as end surfaces of the third surfaces 66 and the fourth surfaces 68 with the second side surfaces 74 and the third side surfaces 76. An edge between the third surface 66 and the outermost edge 80 of the treatment section 54 is preferably formed as sharp as possible at a right angle. In this case, the concave bone socket 100 or a through-hole (tunnel) in the outer shape of the third surfaces 66 is easily formed. An edge between the fourth surface 68 and the outermost edge 80 of the treatment section 54 is preferably as sharp as possible at a right angle. In this case, the concave bone socket 100 or a through-hole in the outer shape of the fourth surfaces 68 is easily formed.

An area S1 of the first surface 62 of the treatment section 54 according to the present embodiment is larger than an area S2 of each of the two second surfaces 64. The area S2 of each of the second surfaces 64 is larger than an area S3 of each of the four third surfaces 66. The area S3 of each of the third surfaces 66 is larger than an area S4 of each of the four fourth surfaces 68.

FIG. 5A illustrates a section that is parallel to the YZ plane formed by the Y-axis and the Z-axis, and is along a first virtual surface α1 (line 5A-5A in FIG. 3) passing through the central line Cx. The first virtual surface α1 is defined as a region including the longitudinal axis L (Z-axis) and the first orthogonal direction (Y-axis) orthogonal to the longitudinal axis L.

FIG. 5B illustrates a section along a second virtual surface α2 (line 5B-5B in FIG. 3). The virtual surface α2 is parallel to the first virtual surface α1, and is in a position deviated toward the end surface 82 in the X-axis direction from the central line Cx.

FIG. 5C illustrates a section along a third virtual surface α3 (line 5C-5C in FIG. 3). The third virtual surface α3 is parallel to the first virtual surface α1 and the second virtual surface α2, and is in a position deviated toward the end surface 82 in the X-axis direction from the second virtual surface α2.

In examples illustrated in FIG. 5A to FIG. 5C, the first surface 62 at a distal end has a first width (dimension) W1 in the first orthogonal direction (Y-axis direction) orthogonal to the longitudinal axis L. The pair of second surfaces 64 which are on the proximal end side one step from the first surface 62 via the first side surfaces 72 have a second width (dimension) W2 toward the end surfaces 84 of the long sides from the central line Cy. The two pairs of third surfaces 66 that are on the proximal end side one step from the second surfaces 64 have a third width (dimension) W3 toward the end surfaces 84 of the long sides from the second surfaces 64. The fourth surfaces 68 on the proximal end side one step from the third surfaces 66 have a fourth width (dimension) W4 toward the end surfaces 84 of the long sides from the third surfaces 66.

Hereinafter, the width W1 in the first surface 62, and the width W2 in the second surface 64 will be compared.

In the example illustrated in FIG. 5A, the first width W1 (Wα1) of the first surface 62 is larger than each of second widths W2 of the pair of second surfaces 64. The first width W1 illustrated in FIG. 5A is a maximum width along the Y-axis direction of the first surface 62.

In the example illustrated in FIG. 5B, the first width W1 (Wα2) of the first surface 62 is equal to each of the second widths W2 of a pair of second surfaces 64.

In the example illustrated in FIG. 5C, the first width W1 (Wα3) of the first surface 62 is smaller than each of the second widths W2 of the pair of second surfaces 64. The first width W1 illustrated in FIG. 5C is a minimum width along the Y-axis direction of the first surface 62.

In this way, in the present embodiment, the width W1 in the Y-axis direction in the first surface 62 of the treatment section 54 varies according to positions in the X-axis direction.

FIG. 6A illustrates a section that is parallel to the ZX plane formed by the Z-axis and the X-axis, and is along a first virtual surface β1 (line 6A-6A in FIG. 3) passing through the central line Cx. The first virtual surface β1 is defined as a region including the longitudinal axis L (Z-axis) and the second orthogonal direction (X-axis) orthogonal to the longitudinal axis L.

FIG. 6B illustrates a section along a second virtual surface β2 (line 6B-6B in FIG. 3). The second virtual surface β2 is parallel to the first virtual surface β1, and is in a position deviated toward the end surface 84 in the Y-axis direction from the central line Cy.

Note that in the present embodiment, a width Wb between the inner edge 65a and the outer edge 65 of the second surface 64 and a width We between the inner edge 67a and the outer edge 67 of the third surface 66 illustrated in FIG. 3 are preferably formed to be the same partially. Accordingly, the widths W2 and W3 in the Y-axis direction of the second surface 64 and the third surface 66 in an appropriate position in the X-axis direction are the same.

Next, an operation of the treatment system 10 according to the present embodiment will be described.

A joint has a cartilage, cortical bone and cancellous bone. The ultrasonic treatment instrument 22 according to the present embodiment can be used in treatment of cartilage and/or bone (cortical bone and cancellous bone). Here, a case of forming the bone socket 100 in bone B will be taken as an example and described. Note that a series of treatments at the time of performing surgery of reconstructing an anterior cruciate ligament in a knee joint 110 will be briefly described later.

The sheath 44 and the handle 42 are mounted to the probe 46, and the ultrasonic treatment instrument 22 is formed. The treatment section 54 of the probe 46 protrudes to a distal end side along the longitudinal axis L from the distal end of the sheath 44. The ultrasonic transducer 24 is mounted to the ultrasonic treatment instrument 22 and the ultrasonic treatment assembly 12 is formed. At this time, the connection section 52a at the proximal end of the ultrasonic vibration transmittable probe 46 and the connection section 34b of the vibrating body 34 of the ultrasonic transducer 24 are connected.

A surgeon disposes the arthroscope 16 in a positional relation as illustrated in FIG. 1, with respect to the treatment section 54 of the ultrasonic vibration transmittable probe 46 that will be described later of the ultrasonic treatment assembly 12. The treatment section 54 is disposed in a field of view of the arthroscope (endoscope) 16 at a time of seeing the distal end side from the proximal end side near the longitudinal axis L. In other words, from an image that is obtained by using the arthroscope 16 and is displayed on the display 20, the treatment section 54 of the ultrasonic vibration transmittable probe 46 is observed from a rear side. The surgeon observes a state of a part of the bone B where the concave bone socket 100 is desired to be formed, on the display 20, and brings the distal end (first surface 62) of the treatment section 54 of the treatment instrument 22 into contact with the part where the concave bone socket 100 is desired to be formed. The surgeon matches a direction in which the concave bone socket 100 is desired to be formed (desired bone socket direction) with the longitudinal axis L of the treatment instrument 22. Accordingly, the first surface 62 is pressed to a formation position of the bone socket in a state of being orthogonal to or approximately orthogonal to the direction of a desired bone socket that is formed in the bone B as a treatment object. The bone socket 100 is formed in a state where irrigating fluid is irrigated into the joint cavity 110a.

In the treatment section 54 of the treatment instrument 22 according to the present embodiment, the projection shape (outermost edge) 80 at a time of the proximal end side being seen from the distal end side along the longitudinal axis L of the treatment section 54 is not circular. Therefore, when the treatment section 54 is rotated around the longitudinal axis L, the outer shape of the hole which is formed becomes different. Accordingly, it can be said that the treatment section 54 has an orientation. Accordingly, the surgeon rotates the probe 46 around the longitudinal axis L while confirming the image by the arthroscope 16, and determines the shape of the bone socket 100 which is desired to be formed.

In this state, the surgeon operates the switch 14a. When the switch 14a is pressed and operated, energy is supplied from the power supply 14 to the ultrasonic transducer 34a of the vibrating body 34 which is fixed to the proximal end of the ultrasonic vibration transmittable probe 46, and ultrasonic vibration is generated in the ultrasonic transducer 34a. Accordingly, the ultrasonic vibration is transmitted to the ultrasonic vibration transmittable probe 46 via the vibrating body 34. The ultrasonic vibration is transmitted toward the distal end side from the proximal end of the ultrasonic vibration transmittable probe 46. For example, the first surface 62 of the treatment section 54 or a vicinity of the first surface 62 is at an anti-node of the vibration. Here, an example where the anti-node of the vibration is formed on the first surface 62 is described, but the anti-node of the vibration may be formed in any position of the second surface 64, the third surface 66 and the fourth surface 68.

The first surface 62 of the treatment section 54 displaces with an appropriate amplitude along the longitudinal axis L at a velocity (for example, several m/s to several thousands m/s) based on the resonance frequency of the transducer 34a. Therefore, when the treatment section 54 is pressed against the bone B by moving the treatment instrument 22 to the distal end side along the longitudinal axis L in a state where vibration is transmitted, a part of the bone B, which the treatment section 54 contacts, is crushed with transmission of the ultrasonic vibration to the treatment section 54. Accordingly, as the treatment instrument 22, that is, the probe 46 is moved toward the distal end side along the longitudinal axis L (center axis C), the concave bone socket 100 is formed in the bone B along the longitudinal axis L (desired bone socket direction) of the treatment section 54 of the ultrasonic vibration transmittable probe 46. Consequently, when the ultrasonic vibration is transmitted to the first surface 62, the ultrasonic vibration transmittable probe 46 is capable of forming the concave bone socket (bone hole) 100 to the longitudinal axis L (desired direction).

When the bone B is under cartilage, and the treatment section 54 of the ultrasonic vibration transmittable probe 46 is pressed against the cartilage toward the distal end side along the longitudinal axis L, a part of the cartilage, which the treatment section 54 contacts, is removed with the transmission of the ultrasonic vibration to the treatment section 54, and a concave bone socket is formed in the cartilage.

The surgeon keeps the state where the surgeon presses and operates the switch 14a, that is, keeps the state where the ultrasonic transducer 34a is vibrated, and moves the treatment section 54 of the probe 46 to a distal side (direction along the Z-axis) along the longitudinal axis L. In the bone B, the concave bone socket 100 in which an opening edge 100a has a size and a shape of the outer edge 63 of the first surface 62 is formed. In other words, in the first surface 62, cutting with the ultrasonic vibration to the treatment section 54 is performed uniformly in such a manner as to copy the shape of the first surface 62 in a depth direction (Z-axis direction). The opening edge 100a of the concave bone socket 100 at this time is smaller than the outermost edge 80 of the treatment section 54. Note that the outer edge 63 of the first surface 62 forms part of the pair of end surfaces 82 that form the short sides of the outermost edge 80 of the treatment section 54.

At this time, an example of a cutting mechanism that forms the concave bone socket (bone hole) 100 in the bone B is considered to be a hammering effect to the bone B by the first surface 62 of the treatment section 54 of the treatment instrument 22 to which the ultrasonic vibration is transmitted along the longitudinal axis L. By the hammering effect, the bone B in a position where the first surface 62 that is the distal end surface abuts is crushed and is cut along the longitudinal axis L.

Crushed debris (cut powder) of the bone B moves toward the outer edge 63 of the first surface 62 along the XY plane from the first surface 62. At this time, the crushed debris moves toward the outer edge 63 of the first surface 62 along the XY plane while being crushed more finely between the first surface 62 and a part of the bone B that faces the first surface 62. The crushed debris that is crushed finely in this way is discharged toward the second surface 64 through a gap between the first side surface (first step) 72 and the bone B from the outer edge 63 of the first surface 62. At this time, the second surface 64 does not contact the bone B, and therefore the crushed debris of the bone B is discharged to the proximal end side of the treatment section 54 through a space between the bone B and the second surface 64. Further, the crushed debris of the bone B is discharged to the proximal end side of the treatment section 54 through the gap between the end surface 82 and the bone B from the first surface 62.

The treatment section 54 according to the present embodiment advances cutting by crushing the bone B with the first surface 62 of the small area S1 instead of advancing cutting by crushing the bone B with the distal end surface of the area S of the outermost edge 80. Consequently, energy that crushes the bone B can be more concentrated on the first surface 62. Accordingly, the concave bone socket 100 in the shape of the first surface 62 smaller than the shape of the outermost edge 80 is more easily formed than a concave bone socket in the shape of the outermost edge 80 being directly formed. Further, when the bone B is cut with the first surface 62, a cutting volume in a case of moving the probe 46 equidistantly in the depth direction is made smaller as compared with a case of cutting the bone B with the distal end surface of the area S of the outermost edge 80 of the treatment section 54. Consequently, as compared with the case of cutting the bone B with the distal end surface of the area S of the outermost edge 80 from the beginning, a cutting velocity in the case of forming the concave bone socket 100 to a same depth with the treatment section 54 of the probe 46 can be improved.

When the concave bone socket 100 is deepened with the first surface 62 to which the ultrasonic vibration is transmitted, the second surface 64 in the position closer to the proximal end side along the longitudinal axis L than the first surface 62 is butted to the bone B. Subsequently, by the hammering effect, the bone B in a position where the first surface 62 abuts, and in a position where the second surface 64 abuts is crushed and is cut along the longitudinal axis L.

Crushed debris (cut powder) of the bone B moves along the XY plane from the first surface 62, and is discharged toward the second surface 64 through a gap between the first side surface (first step) 72 and the bone B from the outer edge 63 of the first surface 62. Likewise, the crushed debris of the bone B moves along the XY plane from the second surface 64, and is discharged toward the third surface 66 through a gap between the second side surface (second step) 74 and the bone B from the outer edge 65 of the second surface 64. At this time, the third surface 66 does not contact the bone B, and therefore the crushed debris of the bone B is discharged to the proximal end side of the treatment section 54 through a space between the bone B and the third surface 66. Further, the crushed debris of the bone B is discharged to the proximal end side of the treatment section 54 through the gap between the end surface 82 and the bone B from the first surface 62 and the second surface 64.

Here, with respect to the X-axis direction, the outer edges 65 of the second surfaces 64 are parts of the pair of end surfaces 82 that form the short sides of the outermost edge 80 of the treatment section 54. Accordingly, with respect to the X-axis direction, the size of the opening edge 100a formed by the outer edges 65 of the second surfaces 64 is the same as the opening edge 100a formed by the outer edge 63 of the first surface 62, and does not change.

With respect to the Y-axis direction, the second surfaces 64 are in positions deviated toward the end surfaces 84 that form the long sides of the outermost edge 80 from the central line Cy of the first surface 62. Accordingly, the opening edge 100a formed by the outer edges 65 of the second surfaces 64 is larger in the Y-axis direction as compared with the opening edge 100a formed by the outer edge 63 of the first surface 62.

In this way, with the treatment section 54, the concave bone socket 100 having the opening edge 100a in the shape of the outer edges 65 of the second surfaces 64 is formed. In other words, when the treatment section 54 of the probe 46 is moved to the distal side along the longitudinal axis L, in the bone B, the concave bone socket 100 is formed, which is smaller than the outermost edge 80 of the treatment section 54, but has the opening edge 100a in a same shape as the shape of the outer edge 65 of the second surface 64. In the second surfaces 64, cutting with the ultrasonic vibration to the treatment section 54 is performed uniformly in such a manner as to copy the shapes of the second surfaces 64 in the depth direction (Z-axis direction). An inner area of the opening edge 100a of the concave bone socket 100 at this time is larger as compared with an inner area of the opening edge 100a of the concave bone socket 100 formed with only the first surface 62. The concave bone socket 100 at this time has the first side surfaces (first steps) 72 parallel to the longitudinal axis L between the first surface 62 and the second surfaces 64, and therefore is formed as a stepped hole.

Further, when the bone B is cut with both the first surface 62 and the second surfaces 64, a cutting volume in the case of moving the probe 46 equidistantly in the depth direction is decreased as compared with the case of cutting the bone B with the distal end surface with the area S of the outermost edge 80 of the treatment section 54. Accordingly, a cutting velocity in the case of forming the concave bone socket 100 at the same depth with the treatment section 54 of the probe 46 can be improved as compared with the case of cutting the bone B with the distal end surface with the area S of the outermost edge 80 from the beginning.

Subsequently, the third surfaces 66 are butted to the bone B while the concave bone socket 100 is deepened with the first surface 62 and the second surfaces 64, and the concave bone socket 100 having the opening edge 100a in a shape of the outer edges 67 of the third surfaces 66 is formed. In other words, when the treatment section 54 of the probe 46 is moved to the distal side along the longitudinal axis L, the concave bone socket 100 that is smaller than the outermost edge 80 of the treatment section 54 but has the opening edge 100a in a same shape as the shape of the outer edges 67 of the third surfaces 66 is formed in the bone B. With the third surfaces 66, cutting with ultrasonic vibration to the treatment section 54 is uniformly performed so as to copy the shapes of the third surfaces 66 in the depth direction (Z-axis direction). An area inside of the opening edge 100a of the concave bone socket 100 at this time is larger as compared with the area inside of the opening edge 100a of the concave bone socket 100 which is formed with the second surfaces 64.

With respect to the Y-axis direction, the opening edge 100a formed with the outer edges 67 of the third surfaces 66 becomes larger in the Y-axis direction as compared with the opening edge 100a formed with the outer edges 65 of the second surfaces 64. The outer edges of the third surfaces 66 correspond to part of the long sides (end surfaces 84) of the outermost edge 80 of the treatment section 54. Crushed debris of the bone B is discharged to the fourth surfaces 68 through the first surface 62, the first side surfaces 72, the second surfaces 64, the second side surfaces 74, the third surfaces 66 and the third side surfaces (third steps) 76. In other words, the crushed debris formed by the third surfaces 66 is discharged toward the fourth surfaces 68 with the crushed debris formed by the first surface 62 and the second surfaces 64. Further, part of the crushed debris of the bone B is discharged to the end surfaces 84 of the outermost edge 80 through the third side surfaces 76.

With respect to the X-axis direction, the outer edges of the third surfaces 66 are same as the short sides (end surfaces 82) of the outermost edge 80 of the treatment section 54. Accordingly, with respect to the X-axis direction, a size of the opening edge 100a formed with the outer edges 65 of the second surfaces 64 is same as the opening edge 100a formed with the outer edges 63 of the first surfaces 62. Further, crushed debris of the bone B is discharged to the end surfaces 82 from the first surface 62 and the second surfaces 64.

Subsequently, the fourth surfaces 68 are butted to the bone B while the concave bone socket 100 is deepened with the first surface 62, the second surfaces 64 and the third surfaces 66, and the concave bone socket 100 (refer to FIG. 7) having the opening edge 100a in a shape of the outer edges of the fourth surfaces 68 is formed. In other words, when the treatment section 54 of the probe 46 is moved to the distal side along the longitudinal axis L, the concave bone socket 100 having the opening edge 100a in a same shape as the shape of the outermost edge 80 of the treatment section 54 including the fourth surfaces 68 is formed in the bone B. With the fourth surfaces 68, cutting with ultrasonic vibration to the treatment section 54 is performed uniformly in such a manner as to copy the shapes of the fourth surfaces 68 and the outermost edge 80 of the treatment section 54 in the depth direction (Z-axis direction). An area of an inside of the opening edge 100a of the concave bone socket 100 at this time is larger as compared with the area of an inside of the opening edge 100a of the concave bone socket 100 which is formed with the third surfaces 66. The concave bone socket 100 is formed at an appropriate depth relative to the opening edge 100a.

With respect to the Y-axis direction, the opening edge 100a formed with the outer edges of the fourth surfaces 68 is larger in the Y-axis direction as compared with the opening edge 100a formed with the outer edges of the third surfaces 66. Further, the opening edge 100a at this time has a same shape as the long sides (end surfaces 84) of the outermost edge 80 of the treatment section 54. Crushed debris of the bone B is discharged to the end surfaces 82 and 84 of the outermost edge 80 of the treatment section 54. In other words, the crushed debris formed by the fourth surfaces 68 is discharged toward the end surfaces 84 with the crushed debris formed by the first surface 62, the second surfaces 64 and the third surfaces 66.

Figure 7:
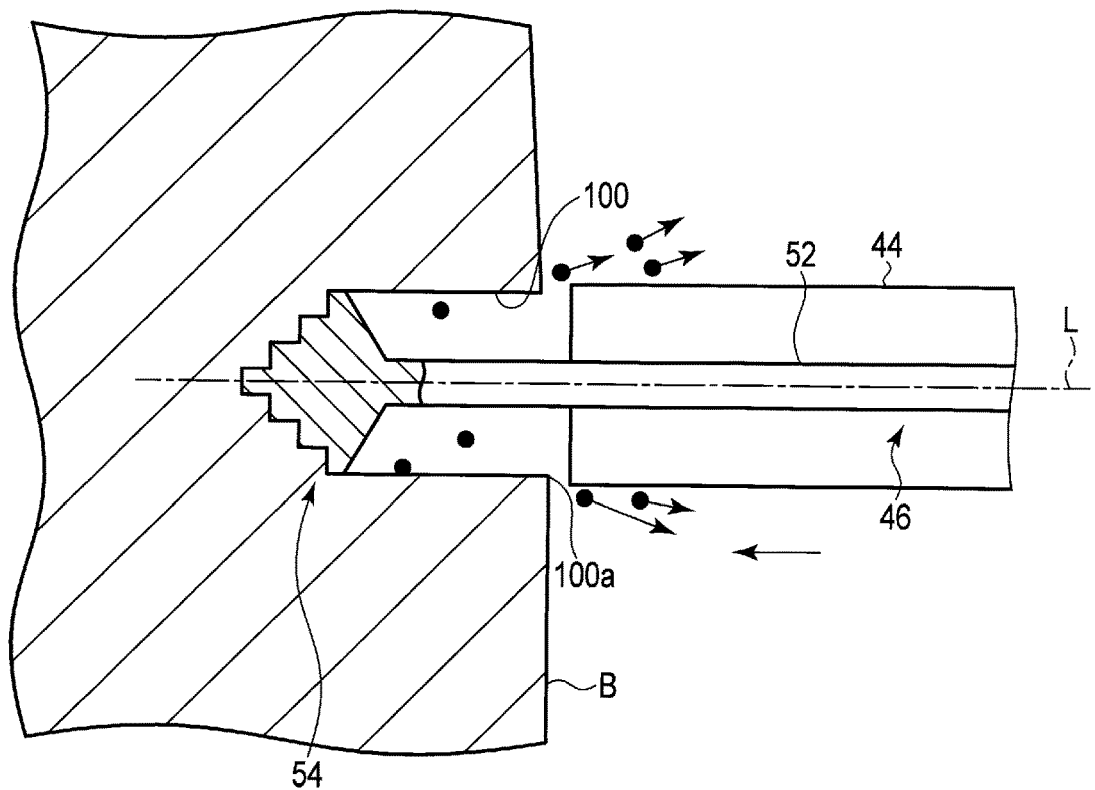
FIG. 7 is a schematic view illustrating a state of forming a concave bone socket in bone with a treatment instrument having an ultrasonic vibration transmittable probe having the treatment section having a section illustrated in FIG. 5B.

Accordingly, as illustrated in FIG. 7, the concave bone socket 100 having the opening edge 100a in the same shape as the outermost edge 80 of the treatment section 54 is formed in the bone B.

In an image by the arthroscope 16, the scale 56 at the distal end portion of the probe body 52 can be observed. The surgeon determines the scale 56 of the image by the arthroscope 16, and estimates a depth of the concave bone socket 100. When the concave bone socket 100 with a desired depth is formed, the pressure on the switch 14a is released. Transmission of the ultrasonic vibration to the probe 46 is released.

When observation of the treatment section 54 is hindered by crushed debris or the like even though the concave bone socket 100 with a necessary depth is not formed, pressure on the switch 14a is released once, and transmission of the ultrasonic vibration to the treatment section 54 is stopped. After the treatment section 54 becomes observable again, the switch 14a is pressed again, and ultrasonic vibration is transmitted to the treatment section 54.

When the area of the opening edge 100a is sequentially increased with the first surface 62, the second surfaces 64, the third surfaces 66 and the fourth surfaces 68, the crushed debris generated by the transmission of ultrasonic vibration transmitted to the respective surfaces (first surface 62, for example) decreases as compared with the case of cutting the bone B with the distal end surface having a same area as the area S of the outermost edge 80 of the treatment section 54. There is a difference (first step) along the longitudinal axis L (Z-axis direction) between the first surface 62 and the second surfaces 64, and therefore, even when the bone B is simultaneously cut with the first surface 62 and the second surfaces 64, a difference occurs to the discharge timing of the crushed debris correspondingly to a length along the longitudinal axis L of the first side surface 72. Further, since the crushed debris that is cut with the first surface 62, for example, moves toward the proximal end side of the treatment section 54 along the longitudinal axis L, the crushed debris is crushed with the second surfaces 64 more finely, is crushed more finely with the third surfaces 66, and can be crushed more finely with the fourth surfaces 68. Likewise, for example, the crushed debris cut with the second surfaces 64 is crushed more finely with the third surfaces 66, and can be crushed more finely with the fourth surfaces 68. Accordingly, friction is prevented as much as possible from occurring between the treatment section 54 and the bone B by the crushed debris being caught between the first side surfaces 72 and the bone B, between the second side surfaces 74 and the bone B, and the like. Further, when the bone socket 100 is formed by the treatment section 54 according to the present embodiment, one surface is prevented from being compacted by a large area. Accordingly, discharge of the crushed debris on the first surface 62, the second surfaces 64, the third surfaces 66 and the fourth surfaces 68 is smoothly performed respectively, and the velocity at which the concave bone socket 100 with the desired depth is formed can be increased as compared with the case of cutting the bone B with the distal end surface of the area S of the outermost edge 80 of the treatment section 54.

The crushed debris generated by the transmission of the ultrasonic vibration transmitted to the first surface 62 is crushed by the transmission of the ultrasonic vibration transmitted to the second surfaces 64, is crushed by the transmission of the ultrasonic vibration transmitted to the third surfaces 66, and is crushed by the transmission of the ultrasonic vibration transmitted to the fourth surfaces 68 as described above. Consequently, a finished surface of the bone socket 100 that is formed by the edge portions 65 of the second surfaces 64 can be smoother than a finished surface of the bone socket 100 formed by the edge portions 63 of the first surface 62. Likewise, a finished surface of the bone socket 100 formed by the edge portions 67 of the third surfaces 66 can be smoother than the finished surface of the bone socket 100 formed by the edge portions 65 of the second surfaces 64. A finished surface of the bone socket 100 formed by the edge portions 69 of the fourth surfaces 68 can be smoother than the finished surface of the bone socket 100 formed by the edge portions 67 of the third surfaces 66. Accordingly, by using the treatment section 54 in the stepped shape according to the present embodiment, the finished surface can be smoother when the bone socket 100 is formed, as the finished surface is away from the central line Cy to the Y-axis direction.

Further, with reference to FIG. 5A to FIG. 5C, cutting performances based on a difference in width W on sections along the Y-axis direction, of the first surface 62 and the second surface 64 of the treatment section 54 are compared. Here, a relationship between the first surface 62 and one of the pair of second surfaces 64 will be described.

Here, when ultrasonic vibration is transmitted to the probe 46, the distal end (first surface 62) of the treatment section 54 or a vicinity of the distal end is at an anti-node position of the vibration. In the distal end (first surface 62) of the treatment section 54 and the vicinity of the distal end of the treatment section 54, amplitude by transmission of ultrasonic vibration becomes largest along the longitudinal axis L. A length along the longitudinal axis L from the first surface 62 to the fourth surface 68 is several millimeters. A part where the first surface 62 to the fourth surfaces 68 are formed is apart from a node of the vibration to the distal end side along the longitudinal axis L. Note that a first vibration node position from the distal end of the treatment section 54 is at a position about several centimeters away from the first surface 62, and is in a position closer to the proximal end side than the inclined surface 54a of the treatment section 54, for example. When the first surface 62 is at the anti-node position of the vibration, largest amplitude of vibration (longitudinal vibration) in a direction along the longitudinal axis L is obtained on the first surface 62. At this time, the amplitude of the longitudinal vibration at the fourth surface 68 is substantially at a same level as in the anti-node position. Therefore, in a state where ultrasonic vibration is transmitted, cutting performance of the bone B per unit area of the fourth surface 68 hardly changes as compared with the first surface 62, and is substantially at a same level. In other words, cutting performances of the bone B per unit area with the second surfaces 64 and the third surfaces 66 that are located closer to the distal end side along the longitudinal axis L than the fourth surfaces 68 also hardly change relative to the first surface 62, and are substantially at a same level.

In a section illustrated in FIG. 5A on a surface α1 in FIG. 4 of the treatment section 54, the width W1 in the Y-axis direction of the first surface 62 is larger as compared with the width W2 in the Y-axis direction of the second surface 64. A very small width in the X-axis direction of the first surface 62 and the second surface is assumed to be a unit width. At this time, a difference between a cutting amount (amount of crushed debris) of the bone B per unit time by a region by the unit width and the width W1 of the first surface 62, and a cutting amount (amount of crushed debris) of the bone B per unit time by a region by the unit width and the width W2 of the second surface 64 depends on dimensions of the widths W1 and W2. Here, the width W1 in the Y-axis direction of the first surface 62 is larger than the width W2 in the Y-axis direction of the second surface 64. A depth of the concave bone socket 100 advancing by the first surface 62, and a depth of the concave bone socket 100 advancing by the second surface 64 are same because a positional relationship between the first surface 62 and the second surface 64 does not change. Accordingly, when the concave bone socket 100 is deepened by advancing the treatment section 54 along the longitudinal axis L in the state where ultrasonic vibration is transmitted, an amount of the bone B cut by the second surface 64 is smaller than an amount of the bone B cut by the first surface 62. Accordingly, in the state where the ultrasonic vibration is transmitted, an amount of crushed debris generated by the transmission of the ultrasonic vibration to the second surface 64 is smaller than an amount of crushed debris generated by the transmission of the ultrasonic vibration to the first surface 62. When it is assumed that same energy is supplied to the first surface 62 and the second surface 64 along the longitudinal axis L at this time, fine work can be performed by the small region (second surface 64) rather than the large region (first surface 62). Accordingly, in the section illustrated by FIG. 5A of the treatment section 54, the finished surface of the cut surface becomes smoother by forming the surface (side surface) of the bone socket 100 with the second surface 64 than by forming the surface (side surface) of the bone socket 100 with the first surface 62.

In a section illustrated in FIG. 5C on a surface α3 in FIG. 4 of the treatment section 54, the width W1 in the Y-axis direction of the first surface 62 is smaller as compared with the width W2 in the Y-axis direction of the second surface 64. The width W2 in the Y-axis direction of the second surface 64 and the width W3 in the Y-axis direction of the third surface 66 are same. The width W4 in the Y-axis direction of the fourth surface 68 is smaller as compared with the widths W1, W2 and W3. It is easily understood by those who skilled in the art that as a contact area with the bone B is smaller (the width W1 is smaller), such as the distal end being pointed, a time until the concave bone socket 100 starts to be formed onto the bone B can be reduced more. Accordingly, when treatment is made with a small region (position having the first width W1) of the area S1 at the beginning of the treatment, it is possible to start forming the concave bone socket 100 by moving the treatment section 54 in the depth direction earlier in a state where an axis misalignment hardly occurs. Accordingly, when the bone socket 100 is formed by using the treatment section 54 having a portion with the small width W1, a misalignment of the treatment section 54 with respect to a desired position hardly occurs. When treatment to form the concave bone socket 100 in hard tissue like the bone B is to be performed, the bone B and the treatment section 54 are slippery at the beginning because there is no catch between the bone B and the treatment section 54. However, by forming the part having the small width on the first surface (distal end surface) 62 as in the section illustrated in FIG. 5C, it is possible to start forming the concave bone socket 100 early. Since the concave bone socket 100 is formed in the shape of the first surface 62 of the treatment section 54, the positional relationship between the bone B and the treatment section 54 is kept easily.

In the section illustrated in FIG. 5B on a surface α2 in FIG. 4, of the treatment section 54, the width W1 in the Y-axis direction of the first surface 62 is same as the width W2 in the Y-axis direction of the second surface 64. At this time, it is possible to start forming the concave bone socket 100 earlier while preventing a misalignment of the treatment section 54 in the case of forming the bone socket 100, and the first surface 62 and the second surface 64 can make the finished surfaces of the cut surfaces substantially uniform when advancing formation of the concave bone socket 100. In other words, in the section illustrated in FIG. 5B, the action in the section illustrated in FIG. 5A is balanced with the action in the section illustrated in FIG. 5C, the concave bone socket 100 is formed earlier, and the finished surfaces of the cut surfaces are uniformized.

As described with use of FIG. 5A to FIG. 5C, when considering a range that is along the Y-axis direction, and is very narrow in the X-axis direction, the treatment section 54 according to the present embodiment has the portion in which the width W1 is small (refer to FIG. 5C), and therefore when the bone B is caused to abut on the first surface 62 of the treatment section 54 to which ultrasonic vibration is transmitted, the concave bone socket 100 starts to be formed earlier. Consequently, the concave bone socket 100 in the shape of the first surface 62 starts to be formed earlier with not only the portion in which the width W1 is small (refer to FIG. 5C) but also the portion in which the width W1 is large, which is formed continuously to the portion in which the width W1 is small (refer to FIG. 5A and FIG. 5B), in the first surface 62. Accordingly, a position where the concave bone socket 100 is formed hardly deviates from the desired position of the bone B. The area S1 of the first surface 62 is not circular, and has an appropriate dimension, so that the treatment section 54 can be restrained from rotating in a circumferential direction of the longitudinal axis L, and the concave bone socket 100 is formed straight along the longitudinal axis L.

As described above, cutting finish between the first surface 62 and the bone B, and cutting finish between the second surface 64 and the bone B depend on a discharge amount of crushed debris per unit time. In the present embodiment, in the first surface 62, the dimension of the width W1 varies along the X-axis direction. In reality, the crushed debris of the bone B which is cut is considered to be influenced by the vibration of the first surface 62, and go in a random direction. Consequently, the finished surface does not vary greatly according to the position along the X-axis direction, but is formed to be substantially uniform. Accordingly, from a microscopic viewpoint, in a part where the width W1 is larger than the width W2 along the Y-axis direction, cutting finish between the first surface 62 and the bone B becomes rougher than cutting finish between the second surface 64 and the bone B. However, since in the treatment section 54 according to the present embodiment, the width W varies along the X-axis direction, the cutting finish between the first surface 62 and the bone B hardly becomes rough with respect to the cutting finish between the second surface 64 and the bone B even in the part where the width W1 is larger than the width W2 along the Y-axis direction, from a macroscopic viewpoint.

When the bone B is cut, as compared with the case of cutting the bone B with the distal end surface with the sectional area S of the outermost edge 80 of the treatment section 54, the area S1 of the first surface 62 is smaller, and therefore the cutting volume of the bone B can be reduced when the probe 46 is moved equidistantly in the depth direction of the concave bone socket 100. Consequently, as compared with the case of cutting the bone B with the distal end surface of the area S of the outermost edge 80 from the beginning, the cutting velocity in the case of forming the concave bone socket 100 to a same depth with the treatment section 54 of the probe 46 can be improved.

Figure 8:
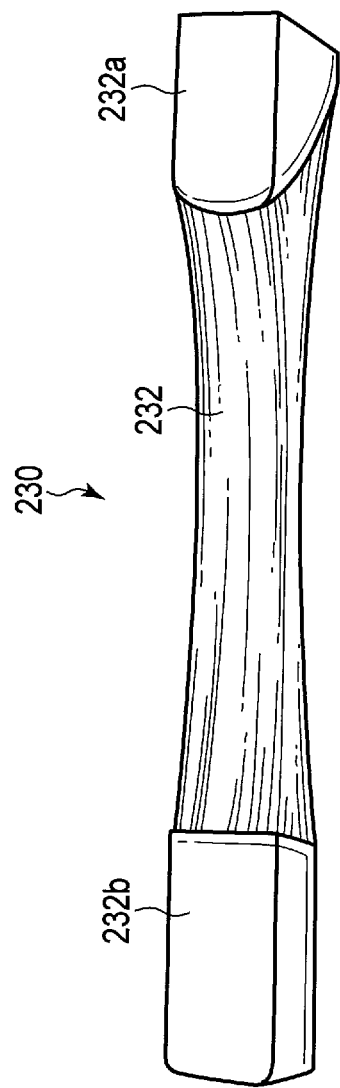
FIG. 8 is a schematic view illustrating a graft tendon extracted from a tendon between a patella and a tibia.

Next, an example of using a patella tendon 232 with bone plugs 232a and 232b attached to both ends illustrated in FIG. 8 as a graft tendon 230 will be described.

One bone plug 232a is a part of a patella (not illustrated). The bone plug 232a on a patella side is in a shape of a substantially triangular pole. The other bone plug 232b is a part of a tibia 114. The bone plug 232b on a tibia 114 side is in a shape of a rectangular parallelepiped. Outer shapes of the bone plugs 232a and 232b are each approximately 10 mm×5 mm, for example. More specifically, an outer shape of a section orthogonal to the longitudinal axis of the graft tendon is formed into a substantially rectangular shape, a substantially elliptic shape close to a rectangular shape, or the like. The graft tendon like this is referred to as a BTB tendon.

As schematically illustrated in FIG. 9A to FIG. 9E as an example, a technique in a case of forming concave bone sockets (bone holes) 100, 101, 102 and 103 in a femur 112 and the tibia 114 by using an inside-out method will be briefly described. Here, the outer shape of the outermost edge 80 of the treatment section 54 according to the present embodiment has a short side of 4 mm and a long side of 5 mm. Consequently, a plurality of concave bone sockets 100 and 101 are provided side by side in the femur 112, and a plurality of concave bone sockets 102 and 103 are provided side by side in the tibia 114. When the concave bone sockets 100 and 101 are provided side by side, opening edges 100a and 101a are formed into a rectangular shape of approximately 10 mm×5 mm, for example. Likewise, when the concave bone sockets 102 and 103 are provided side by side, opening edges 102a and 103a are formed into a rectangular shape of approximately 10 mm×5 mm, for example. Depending on sizes of the bone plugs 232a and 232b, continuous concave bone sockets may be formed by a plurality of times of treatments such as five times, for example. When the graft tendon 230 is fixed with a screw, the concave bone socket may be formed with a gap in which the screw is put taken into consideration.

The graft tendon 230 is preferably disposed in a same portion as a portion to which an injured anterior cruciate ligament is attached. Accordingly, the bone socket 100 is formed in a same part as a part where the anterior cruciate ligament is attached. The portion where the injured anterior cruciate ligament is attached is cleared up by using a treatment unit not illustrated, and footprints 116 and 118 to which the anterior cruciate ligament is attached are clarified. At this time, an appropriate ultrasonic treatment instrument, an abrader, a high-frequency treatment instrument and the like (none of them is illustrated) can be used.

In the bone socket 100, a position in which the bone plugs 232a and 232b of the graft tendon 230 are inserted preferably has a dimension and a shape corresponding to the outer shape of the graft tendon 230. Consequently, when the graft tendon 230 is taken, a dimension (outer shape) of the graft tendon 230 is measured.

Subsequently, positions where the bone sockets 100, 101, 102 and 103 are formed are decided by marking the positions or the like to the footprints 116 and 118. Though not illustrated, the footprint 116 is in an outer wall rear portion of an intercondylar fossa of the femur 112. Further, the footprint 118 is inside of an anterior intercondylar area of the tibia 114.

From an appropriate portal, the treatment section 54 of the ultrasonic treatment instrument 22 is inserted into the joint cavity 110a of the knee joint 110. Further, a distal end of the arthroscope 16 is inserted into the joint cavity 110a. At this time, the treatment section 54 and the arthroscope 16 are in the positional relationship as illustrated in FIG. 1. While an inside of the joint cavity 110a is confirmed with the arthroscope 16, the distal end (first surface 62) of the treatment section 54 is caused to abut on the footprint 116 of the femur 112.

Figure 9A:
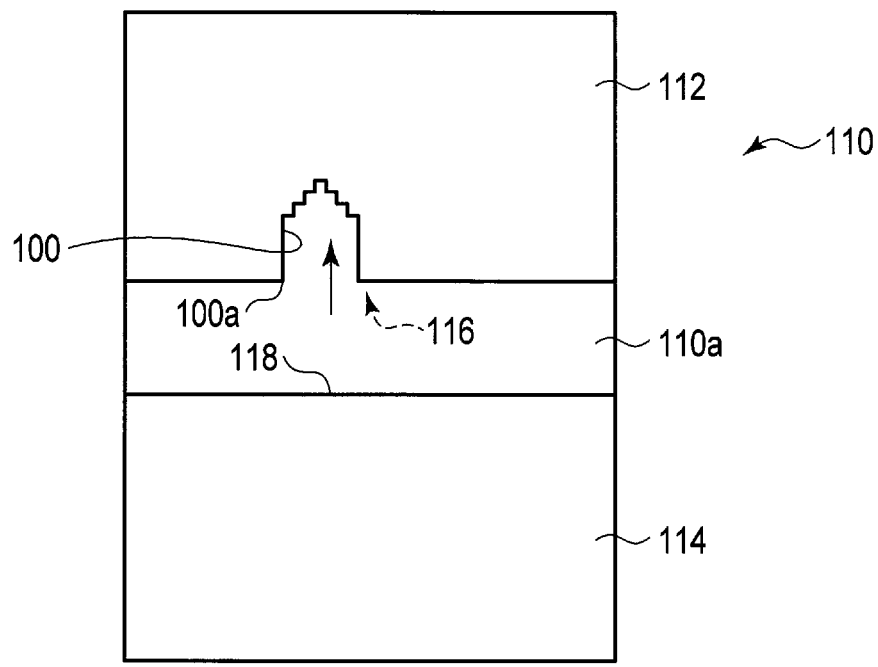
FIG. 9A is a schematic view illustrating a state where a bone socket is formed inside an area of a footprint of an anterior cruciate ligament on a femur to reconstruct the anterior cruciate ligament with the graft tendon illustrated in FIG. 8.
Figure 9B:
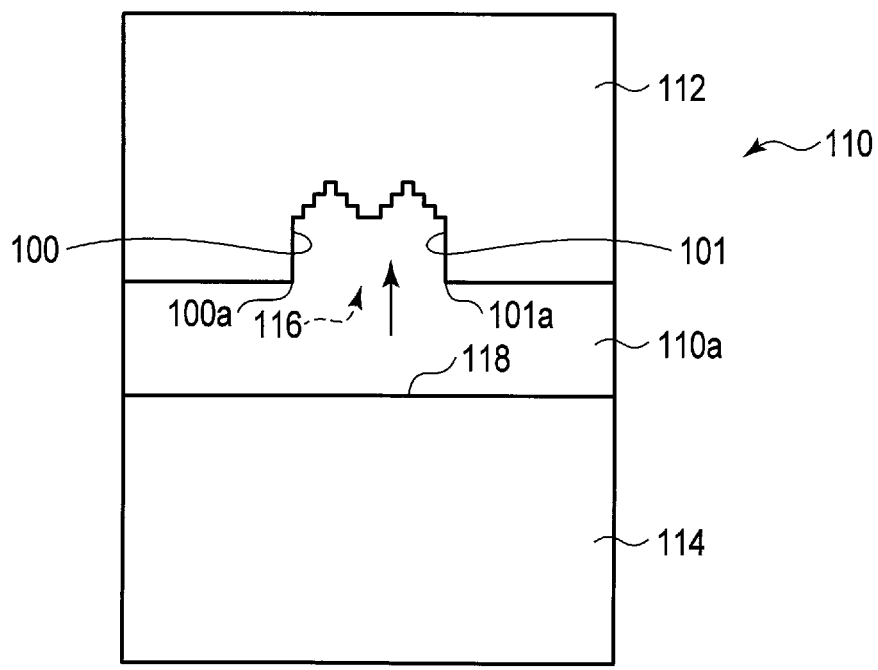
FIG. 9B is a schematic view illustrating a state where a bone socket is formed parallel to the bone socket illustrated in FIG. 9A, so as to be in an enough size for a bone plug of the graft tendon illustrated in FIG. 8 to fit therein.

Subsequently, as illustrated in FIG. 9A, the first bone socket (concave bone socket here) 100 is formed in the footprint 116 of the femur 112. As illustrated in FIG. 9B, the second bone socket 101 adjacent to the first bone socket 100 is formed in the footprint 116 of the femur 112. At this time, an opening edge in a substantially rectangular shape is formed by the opening edge 100a of the first bone socket 100 and the opening edge 101a of the second bone socket 101. At this time, a formation velocity of the concave bone sockets 100 and 101 is improved, and finished surfaces of the concave bone sockets 100 and 101 are made as smooth as possible.

Figure 9C:
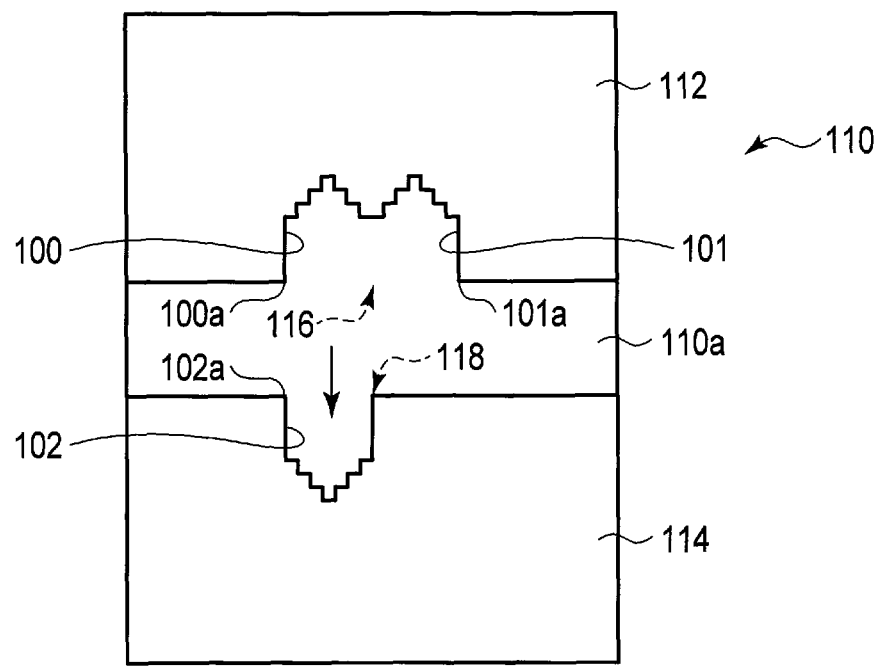
FIG. 9C is a schematic view illustrating a state where a bone socket is formed inside an area of a footprint of an anterior cruciate ligament on a tibia to reconstruct the anterior cruciate ligament with the graft tendon illustrated in FIG. 8.
Figure 9D:
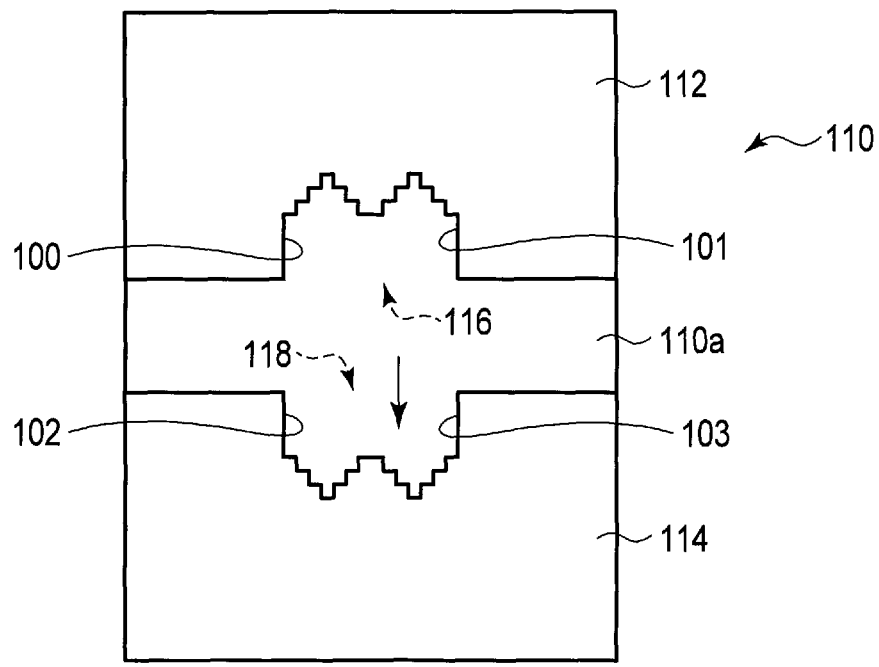
FIG. 9D is a schematic view illustrating a state where a bone socket is formed parallel to the bone socket illustrated in FIG. 9C, so as to be in an enough size for a bone plug of the graft tendon illustrated in FIG. 8 to fit therein.

Likewise, as illustrated in FIG. 9C, the third bone socket (concave bone socket here) 102 is formed in the footprint 118 of the tibia 114. As illustrated in FIG. 9D, the fourth bone socket 103 adjacent to the third bone socket 102 is formed in the footprint 118 of the tibia 114. At this time, an opening edge in a substantially rectangular shape is formed by the opening edge 102a of the third bone socket 102 and the opening edge 103a of the fourth bone socket 103. At this time, a formation velocity of the concave bone sockets 102 and 103 is improved, and finished surfaces of the concave bone sockets 102 and 103 are made as smooth as possible.

Figure 9E:
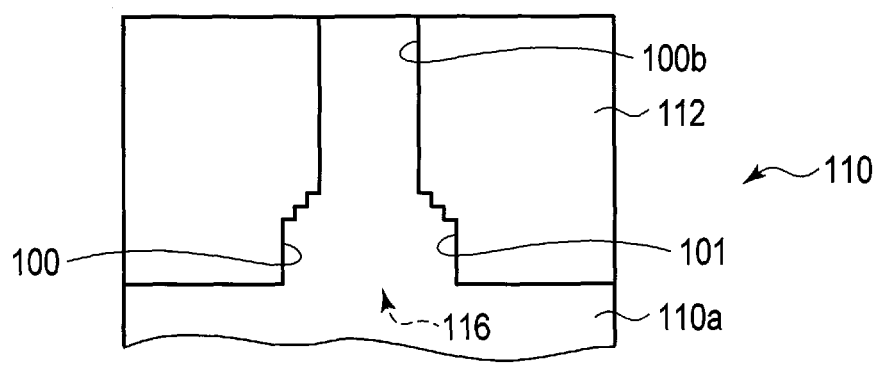
FIG. 9E is a schematic view illustrating a state where a through-hole is formed in the bone socket on the femur illustrated in FIG. 9D.

As illustrated in FIG. 9E, a bone tunnel 101b is formed in the femur 112, for example, by using a drill or the like.

With an orientation of the graft tendon 230 taken into consideration, the graft tendon 230 is disposed in the bone sockets 100 and 101 on a femur 112 side, and is disposed in the bone sockets 102 and 103 on a tibia 114 side. A conventionally known method can be appropriately used in fixation of the femur 112 and the graft tendon 230, and fixation of the tibia 114 and the graft tendon 230.

When inner circumferential surfaces of the bone sockets 100 and 101 are smooth at this time, it becomes easier to dispose the bone plug 232a than in a rough state. Further, when inner circumferential surfaces of the bone sockets 102 and 103 are smooth, it becomes easier to dispose the bone plug 232b than in a rough state. In the present embodiment, the inner circumferential surfaces of the bone sockets 100, 101, 102 and 103 can be formed to be as smooth as possible, so that the bone plugs 232a and 232b of the graft tendon 230 are easily put into the bone sockets 100, 101, 102 and 103, and treatment efficiency is improved.

By forming the bone sockets 100 and 101 on the femur 112 side and the bone sockets 102 and 103 on the tibia 114 side in accordance with the shape of the graft tendon 230, a gap formed between the graft tendon 230 and the bone sockets 100 and 101, and a gap formed between the graft tendon 230 and the bone sockets 102 and 103 can be decreased as much as possible. Since a gap between the graft tendon 230 and the bone is small, a volume to be reproduced as bone is decreased, and ligamentization of the graft tendon 230 can be easily advanced.

Further, by forming the bone sockets 100, 101, 102 and 103 by using the ultrasonic vibration transmittable probe 46 having the treatment section 54 described in the present embodiment, the holes are not forced to open by a dilator. Accordingly, bone fractures can be suppressed for patients with low bone densities, for example, and therefore, the technique using the graft tendon 203 can be easily performed.

Further, in the joint cavity 110a, floating soft tissue such as an excised anterior cruciate ligament can exist. When an appropriate treatment instrument rotates around the longitudinal axis L, the floating soft tissue is likely to be wound on the treatment instrument. Since the probe 46 of the treatment instrument 22 according to the present embodiment only moves in a very small range along the longitudinal axis L, and therefore the floating soft tissue can be prevented from interfering with treatment, such as wrapping around the probe 46.

Here, the example of forming the concave bone sockets 100, 101, 102 and 103 as the bone sockets is described, but a through-hole may be formed by using the ultrasonic vibration transmittable probe 46 having the aforementioned treatment section 54. Further, after the concave bone sockets 100, 101, 102 and 103 are formed, through-holes may be formed respectively in the femur 112 and the tibia 114 by using a drill or the like.

Further, the BTB tendon is described by being taken as an example, but if the bone tunnel that is a through-hole is formed, for example, an STG tendon may be used as a part of the graft tendon. An outer shape of the STG tendon does not have a circular section but often has a rectangular shape close to a substantially elliptical shape, for example, because the tendon is folded back. In this case, the bone sockets 100, 101, 102 and 103 are formed by using the ultrasonic treatment instrument 22 in accordance with the outer shape of the graft tendon.

As described above, according to the present embodiment, the ultrasonic vibration transmittable probe 46 and the ultrasonic treatment assembly 12 can be provided, which are capable of improving the treatment efficiency such as improving the formation velocity of the holes and/or making the finished surfaces of the holes as smooth as possible when forming the holes in bone, for example.

In the treatment section 54 of the aforementioned embodiment, the widths W1 and W2 vary along the X-axis direction. FIG. 10A shows an exemplary treatment section 54 in which the widths W1 and W2 are respectively constant and do not vary along an X-axis direction. The treatment section illustrated in FIG. 10 is formed in a shape of steps with a first surface 62 at a top. Specifically, the treatment section 54 is formed in a shape of steps in which fourth surfaces 68, third surfaces 66, second surfaces 64 and the first surface 62 rise toward a distal end side from a proximal end side along a longitudinal axis L. Shapes of the first surface 62, a pair of second surfaces 64, a pair of third surfaces 66, and a pair of fourth surfaces 68 are each in a same rectangular shape. As mentioned above, the treatment section 54 of a probe 46 in this embodiment shows a case where widths W1 and W2 are respectively constant and do not vary along an X-axis direction. Likewise, in the treatment section 54 of the probe 46 of this embodiment, widths W3 and W4 are respectively same and do not vary along the X-axis direction. The treatment section 54 is formed in the shape of steps in which the fourth surfaces 68, the third surfaces 66, the second surfaces 64 and the first surface 62 rise toward the distal end side from the proximal end side along the longitudinal axis L. The width W1 of the first surface 62 is smaller than the width W2 of the second surface 64. Consequently, an area S2 of the second surface 64 is larger than an area S1 of the first surface 62. Further, areas S2, S3 and S4 of the second surface 64, the third surface 66 and the fourth surface 68 are same. A projection shape of an outermost edge 80 when the treatment section 54 is seen from the distal end side to the proximal end side along the longitudinal axis L is a rectangular shape. The fourth surface 68 is adjacent to the outermost edge 80 on the distal end side along the longitudinal axis L.

In an example of the treatment section 54 having a section illustrated in FIG. 11A, first side surfaces 72, second side surfaces 74 and third side surfaces 76 are parallel to the longitudinal axis L. The first side surfaces (steps) 72 continue to the first surface 62 and the second surfaces 64. The second side surfaces (steps) 74 continue to the second surfaces 64 and the third surfaces 66. The third side surfaces (steps) 76 continue to the third surfaces 66 and the fourth surfaces 68. Consequently, when the treatment section 54 is seen from the distal end side to the proximal end side along the longitudinal axis L, not only the first surface 62, but also the second surfaces 64, the third surfaces 66 and the fourth surfaces 68 are totally recognizable, and exposed. For example, in the second surface 64, an inner edge 65a is not hidden by the first surface 62. Likewise, an inner edge 67a of the third surface 66 is not hidden by the second surface 64, an inner edge 69a of the fourth surface 68 is not hidden by the third surface 66. Accordingly, when a concave bone socket 100 is formed, the first surface 62, the pair of second surfaces 64, the pair of third surfaces 66 and the pair of fourth surfaces 68 are in contact with a bone B on entire surfaces of the respective surfaces 62, 64, 66 and 68 respectively.

A projection shape (inside of an outer edge 63 of the first surface 62) at a time of the first surface 62 being seen from the distal end side to the proximal end side along the longitudinal axis L is smaller than a projection shape (inside of an outer edge 65 of the second surface 64) at a time of the second surface 64 being seen from the distal end side to the proximal end side along the longitudinal axis L. Consequently, the projection shape of the first surface 62 is inside of the outer edge 65 of the second surface 64, is inside of an outer edge 67 of the third surface 66, and is inside of the outer edge (outermost edge 80) of the fourth surface 68. This applies similarly to treatment sections 54 illustrated in FIG. 11B to FIG. 12C.

Figure 10B:
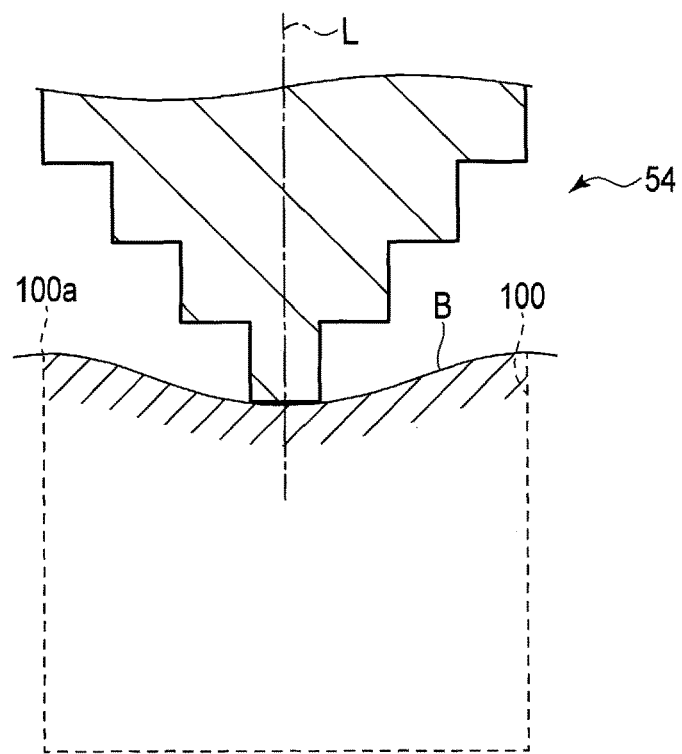
FIG. 10B is a schematic view illustrating a state where a distal end of the treatment section of the ultrasonic vibration transmittable probe according to an exemplary embodiment is caused to abut on a bone in which a hole is to be formed.

Here, when a distal end of the treatment section 54 is caused to abut on the bone B having a complicated curved surface, for example, the treatment section 54 having the distal end of a smaller dimension more easily abut on a desired position reliably. In the treatment section 54 of the present embodiment, as described above, the treatment section 54 illustrated in FIG. 11A has the width (dimension) W1 in the Y-axis direction of the first surface 62 smaller as compared with the width (dimension) W2 in the Y-axis direction of the second surface 64, as illustrated in FIG. 10B. Consequently, the first surface 62 is easily brought into contact with the bone B having the complicated curved surface.

Figure 10C:
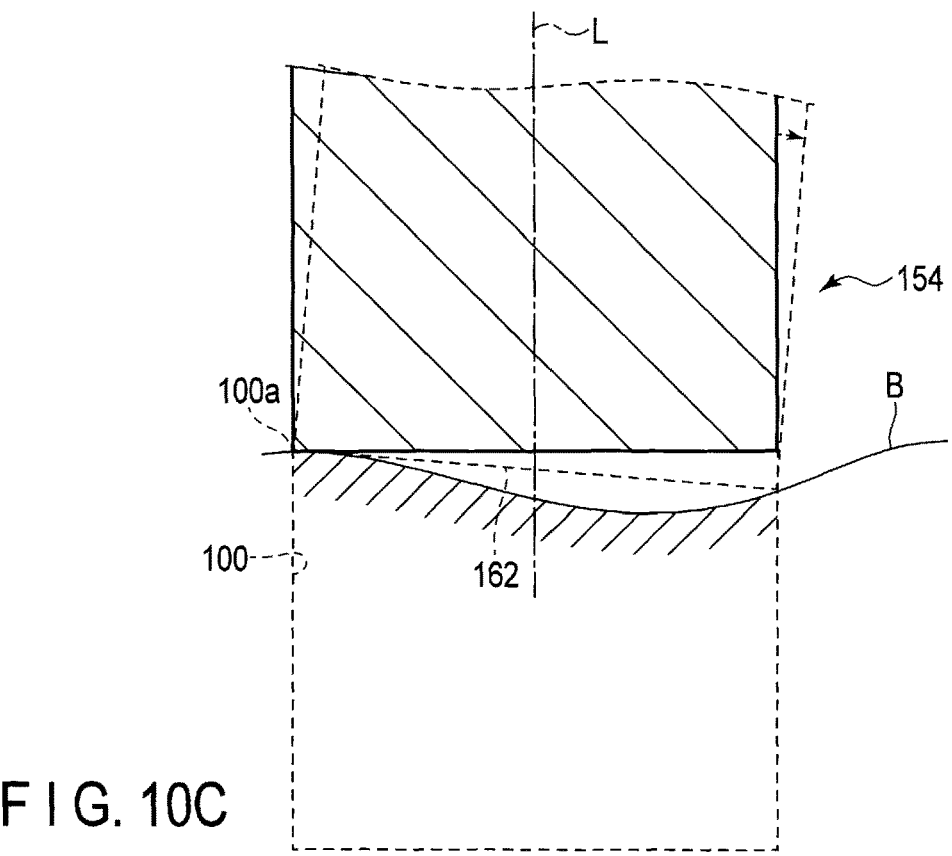
FIG. 10C is a schematic view illustrating a state where a distal end of a treatment section of an ultrasonic vibration transmittable probe according to a reference example is caused to abut on a bone in which a hole is to be formed.

For reference, comparison is made with a case of using an ultrasonic vibration transmittable probe having a treatment section 154 in which an outermost edge 180 and a distal end surface 162 have a same outer shape, illustrated in FIG. 10C.

In the case of using the treatment section 54 of the present example illustrated in FIG. 10B, a ratio of a contact area with the bone B to the first surface 62 is easily made larger as compared with the case of using the treatment section 154 as the reference illustrated in FIG. 10C. Consequently, more energy by ultrasonic vibration transmitted to the first surface 62 is easily transmitted to the bone B. Consequently, in the case of using the treatment section 54 of the present example, it is possible to start forming the concave bone socket 100 earlier. By the edge portion 63 in a planar shape of the first surface 62, an initial hole in a desired shape can be formed.

Consequently, by decreasing the contact area of the first surface 62 of the treatment section 54 and the bone B as much as possible as in the present example, the initial hole is easily formed in the bone B in a desired position in a desired orientation. Following the first surface 62, the bone B is cut with the second surfaces 64, and the concave bone socket 100 can be formed in the desired position in the desired orientation.

In the case of using the treatment section 154 of the example shown as the reference illustrated in FIG. 10C, the ratio of the contact area of the bone B to the distal end surface can be small. When cutting of the bone B is difficult to start even though the treatment section 54 is moved along the longitudinal axis L, there is a fear that a position of the treatment section 154 deviates from the desired position where the hole is desired to be formed, such as the treatment section 154 easily slipping as shown by a broken line, for example.

In an example of the treatment section 54 having a section illustrated in FIG. 11B, a first side surface 72, second side surfaces 74 and third side surfaces 76 incline to a longitudinal axis L. Between a first edge portion 63 of a first surface 62 and a second surface 64, a surface (first side surface 72) inclining to the longitudinal axis L is included. The first side surface 72 to the second surface 64 from the first surface 62 is closer to the longitudinal axis L toward the second surface 64. A second side surface 74 to a third surface 66 from the second surface 64 is closer to the longitudinal axis L toward the third surface 66. A third side surface 76 to a fourth surface 68 from the third surface 66 is closer to the longitudinal axis L toward the fourth surface 68. Further, in the second surface 64, a region in a distance D1 in a Y-axis direction from an inner edge 65a hardly contacts a bone B when a concave bone socket 100 is formed. The region is used as a region where crushed debris is discharged. Likewise, a region in a distance D2 in the Y-axis direction from an inner edge 67a inside of a third surface 66 hardly contacts the bone B when the concave bone socket 100 is formed. The region is used as a region where crushed debris is discharged. A region in a distance D3 in the Y-axis direction from an inner edge 69a inside of a fourth surface 68 hardly contacts the bone B when the concave bone socket 100 is formed. The region is used as a region where crushed debris is discharged. Consequently, the contact area with the bone B at the time of forming the concave bone socket 100 becomes largest on the first surface 62. Each of contact areas with the bone B of a pair of second surfaces 64, a pair of third surfaces 66 and a pair of fourth surfaces 68 is smaller than the contact area of the first surface 62.

When the treatment section 54 is seen from the distal end side to the proximal end side along the longitudinal axis L, not only the first surface 62, but also part of the second surfaces 64, part of the third surfaces 66 and part of the fourth surfaces 68 are also recognizable, and exposed. A part (inside) of the second surface 64 is hidden by the first surface 62, but the part of the second surface 64 is exposed with respect to the first surface 62. A part (inside) of the third surface 66 is hidden by the second surface 64, but the part of the third surface 66 is exposed with respect to the second surface 64. A part (inside) of the fourth surface 68 is hidden by the third surface 66, but the part of the fourth surface 68 is exposed with respect to the third surface 66.

The region in the distance D1 from the inner edge 65a inside of the second surface 64 in FIG. 11B hardly contacts the bone B when the concave bone socket 100 is formed. The region is used as the region where the crushed debris is discharged. Likewise, the region in the distance D2 from the inner edge 67a inside of the third surface 66 hardly contacts the bone B when the concave bone socket 100 is formed. The region is used as the region where the crushed debris is discharged. The region in the distance D3 from the inner edge 69a inside of the fourth surface 68 hardly contacts the bone B when the concave bone socket 100 is formed. The region is used as the region where the crushed debris is discharged.

When the treatment section 54 is moved along the longitudinal axis L while ultrasonic vibration is transmitted, in this case, a vicinity of a boundary between the first side surface 72 and the second surface 64 does not contact the bone B. Consequently, in the vicinity of the boundary between the first side surface 72 and the second surface 64, friction with the bone B does not occur, and irrigating fluid touches the vicinity of the boundary. Accordingly, an ability required at a time of processing the bone socket 100 with use of the ultrasonic vibration transmittable probe 46 can be minimized. Further, at a time of treatment using the ultrasonic vibration transmittable probe 46, a drag received from the bone B can be reduced. Further, the vicinity of the boundary between the first side surface 72 and the second surface 64 is used as a discharge passage for crushed debris. Consequently, the velocity at which the concave bone socket 100 is formed can be increased.

Further, as for a width (width between the end surfaces 84) along the Y-axis direction of the treatment section 54, a width Db in the example illustrated in FIG. 11B is smaller than a width Da in the example illustrated in FIG. 11A. Consequently, when the areas S1, S2, S3 and S4 of the first surface 62 to the fourth surface 68 are respectively same with respect to the examples illustrated in FIG. 11A and FIG. 11B, a length between the end surfaces 84 of the treatment section 54 can be smaller in the example illustrated in FIG. 11B than in the example illustrated in FIG. 11A.

A cutting amount (amount of crushed debris) of the bone B per unit time in a section along the Y-axis direction (first orthogonal direction) orthogonal to the longitudinal axis illustrated in FIG. 11B depends on a width (dimension) of a part contributing to cutting of the bone B, of each of the surfaces 62, 64, 66 and 68. Here, in the first surface 62, the entire surface is used as the part contributing to cutting of the bone B. In the second surface 64, a part contributing to cutting of the bone B depends on a dimension obtained by subtracting the width D2 from the width W2. In the third surface 66, a part contributing to cutting of the bone B depends on a dimension obtained by subtracting the width D3 from the width W3. In the fourth surface 68, a part contributing to cutting of the bone B depends on a dimension obtained by subtracting a width D4 from the width W4.

In the first surface 62, the part contributing to cutting of the bone B is formed to have a smaller dimension than the second surface 64 along the Y-axis direction (first orthogonal direction) orthogonal to the longitudinal axis L. Consequently, as in the example of the treatment section 54 illustrated in FIG. 11A, an initial hole is easily formed in the bone B in a desired position in a desired orientation by using the treatment section 54 illustrated in FIG. 11B. Following the first surface 62, the bone B is cut with the second surfaces 64, and the concave bone socket 100 can be formed in a desired position in a desired orientation.

Here, a depth of the concave bone socket 100 advancing by the second surfaces 64, and a depth of the concave bone socket 100 advancing by the third surfaces 66 are same because a positional relationship between the second surfaces 64 and the third surfaces 66 does not change. Likewise, the depth of the concave bone socket 100 advancing by the second surfaces 64 corresponds to a depth of the concave bone socket 100 advancing by the fourth surfaces 68. Consequently, when the concave bone socket 100 is deepened by advancing the treatment section 54 along the longitudinal axis L in the state where ultrasonic vibration is transmitted, an amount of the bone B cut with the third surfaces 66 is smaller than an amount of the bone B cut with the second surfaces 64. Accordingly, in the state where the ultrasonic vibration is transmitted, the amount of crushed debris generated by transmission of the ultrasonic vibration to the third surfaces 66 is smaller than the amount of crushed debris generated by the transmission of the ultrasonic vibration to the second surfaces 64. When it is assumed that same energy is supplied to the second surfaces 64 and the third surfaces 66 along the longitudinal axis L at this time, a region (part of the third surface 66) with a smaller dimension exhibits cutting performance more easily than a region (second surface 64) with a large dimension. Accordingly, the treatment section 54 illustrated in FIG. 11B makes smoother finish of the cut surface by forming the surface (side surface) of the bone socket 100 with the outer edges 67 of the third surfaces 66 than by forming the surface (side surface) of the bone socket 100 with the outer edges 65 of the second surfaces 64.

This applies similarly to the relationship between the surfaces (fourth surfaces) 68 forming the outermost edge 80 and the surfaces (third surfaces) 66 one step above the surfaces 68. In other words, by making the part contributing to cutting of the bone B, of the fourth surface 68 smaller than the part contributing to cutting of the bone B, of the third surface 66, a wall surface of the concave bone socket 100 can be made smoother when the opening edge 100a of a same dimension as the outermost edge 80 is formed.

Accordingly, the areas of the parts contributing to cutting of the bone B of the respective surfaces 64, 66 and 68 to the proximal end side from the distal end side along the longitudinal axis L (Z-axis direction) and along the Y-axis direction are gradually decreased. Consequently, in the treatment section 54 of the example illustrated in FIG. 11B, the edge portions 65, 67 and 80 of the surfaces 64, 66 and 68 that are closer to the outermost edge 80 from the longitudinal axis L can make the wall surface of the concave bone socket 100 smoother when the opening edge 100a is formed by cutting the bone B.

In FIG. 11B, the width D1 is drawn to be smaller than the width D2, and the width D2 is drawn to be smaller than the width D3. Dimensions of the widths D1, D2 and D3 are appropriately settable. The widths D1, D2 and D3 may be made the same, or the width D1 is made larger than the width D2, and the width D2 may be made larger than the width D3, for example.

Figure 11C:
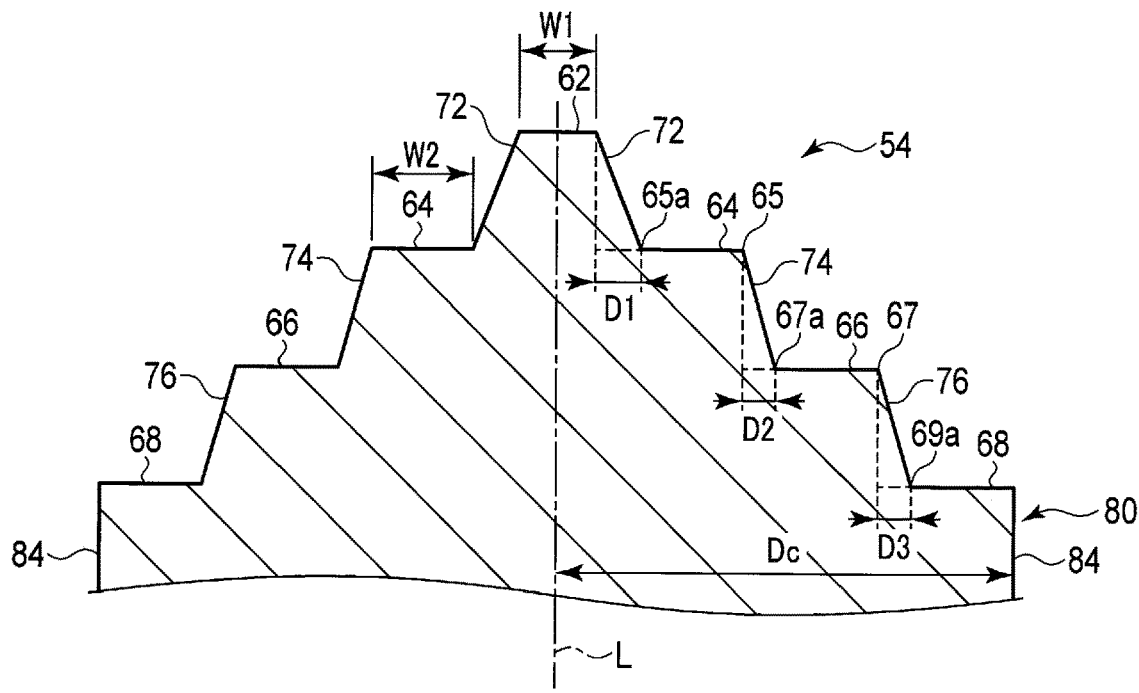
FIG. 11C is an example illustrating a section on an appropriate YX plane in the vicinity of the distal end portion of the treatment section illustrated in FIG. 10A, and different from FIG. 11A and FIG. 11B.

In an example of the treatment section 54 having a section illustrated in FIG. 11C, first side surfaces 72, second side surfaces 74 and third side surfaces 76 incline to an longitudinal axis L. In other words, between a first edge portion 63 of a first surface 62 and a second surface 64, the surface (first side surface 72) that inclines to the longitudinal axis L is included. The first side surface 72 to the second surface 64 from the first surface 62 is farther away from the longitudinal axis L toward the second surface 64. The second side surface 74 to a third surface 66 from the second surface 64 is farther away from the longitudinal axis L toward the third surface 66. The third side surface 76 to a fourth surface 68 from the third surface 66 is farther away from the longitudinal axis L toward the fourth surface 68. Consequently, when the treatment section 54 is seen from the distal end side to the proximal end side along the longitudinal axis L, not only the first surface 62, but also the second surface 64, the third surface 66 and the fourth surface 68 are recognizable and exposed.

Consequently, when the first side surface 72, the second side surface 74 and the third side surface 76 function as the cutting surfaces of a bone B, when forming a concave bone socket 100. In particular, in the first side surface 72, the second side surface 74 and the third side surface 76, vibration components in a direction along the longitudinal axis L contribute to cutting of the bone B. The first side surface 72, the second side surface 74 and the third side surface 76 are more easily processed than in the examples illustrated in FIG. 11A and FIG. 11B, and can prevent stress concentration. The treatment section 54 illustrated in FIG. 11C has a large amount of solid portion (amount removed by processing is small when the treatment section 54 is formed) even when being formed into a state having the same outermost edge 80, and therefore durability can be improved more than the treatment sections 54 illustrated in FIG. 11A and FIG. 11B.

In the first surface 62, the part contributing to cutting of the bone B is formed to be in a smaller dimension than in the second surface 64 along the Y-axis direction (first orthogonal direction) orthogonal to the longitudinal axis L. Consequently, by using the treatment section 54 illustrated in FIG. 11C, an initial hole is easily formed in the bone B in a desired position in a desired orientation, as in the example of the treatment section 54 illustrated in FIG. 11A. Following the first surface 62, the bone B is cut with the second surfaces 64, and the concave bone socket 100 can be formed in a desired position in a desired orientation.

A distance in the Y-axis direction from an outer edge 63 on an outside of the first surface 62 in FIG. 11C to an inner edge 65a inside of the second surface 64 is set as D1. A distance in the Y-axis direction from an outer edge 65 on an outside of the second surface 64 to an inner edge 67a inside of the third surface 66 is set as D2. A distance in the Y-axis direction from an outer edge 67 on an outside of the third surface 66 to an inner edge 69a inside of the fourth surface 68 is set as D3.

There may be cases where it is desired to form the concave bone socket 100 having an opening edge 100a with a larger area by movement of as short a distance as possible along the longitudinal axis L. When areas S1, S2, S3 and S4 of the respective surfaces 62, 64, 66 and 68 are desired to be made the same, in a case where the respective side surfaces 72, 74 and 75 are parallel illustrated in FIG. 11A, or in the case illustrated in FIG. 11B, it is necessary to increase the number (number of steps) of surfaces (planes) in the Y-axis direction.

As described above, when ultrasonic vibration is transmitted to the probe 46, an anti-node position of vibration is on the first surface 62, for example, along the longitudinal axis L in the treatment section 54. At this time, an $n^{th}$ surface (n is a natural number of 2 or more) is in a position closer to the proximal end side along the longitudinal axis L than the first surface 62, and is out of the anti-node position of vibration. Consequently, in theory, the amplitude in the direction along the longitudinal axis L on the $n^{th}$ surface becomes smaller than amplitude in the direction along the longitudinal axis L in the first surface 62. Accordingly, a cutting ability on the $n^{th}$ surface can be reduced with respect to a cutting ability on the first surface 62. Accordingly, when the number of steps (value of n) is excessively increased, there is a fear that a difference occurs in cutting ability between the first surface 62 and the $n^{th}$ surface.

In this example, the first side surface 72 is formed as a plane from the outer edge 63 of the first surface 62 to the inner edge 65a of the second surface 64. The inner edge 65a of the second surface 64 more separates with respect to the longitudinal axis L than the outer edge 63 of the first surface 62. Here, when the proximal end side is seen from the distal end side along the longitudinal axis L, the first side surfaces 72 between the outer edge 63 of the first surface 62, and the inner edges 65a of the second surfaces 64 are recognized.

A distance Dc between a position of a center (longitudinal axis L) of the first surface 62 and an end surface 84 of the fourth surface 68 is larger than a distance Da of the example illustrated in FIG. 11A, and is larger than a distance Db of the example illustrated in FIG. 11B. Even when the respective surfaces 62, 64, 66 and 68 have a same area, an area S of the outermost edge 80 can be made large. Consequently, in the case of using the probe 46 having the treatment section 54 according to the example illustrated in FIG. 11C, it is not necessary to adjust a length in the direction along the longitudinal axis L, and it is possible to form the concave bone socket 100 having a larger opening edge 100a by one operation along the longitudinal axis L.

Note that in the treatment section 54 according to the example illustrated in FIG. 11C, the first side surfaces 72 also vibrate along the longitudinal axis L by transmission of ultrasonic vibration to the probe 46. Consequently, the bone B can also be cut with the first side surfaces 72.

Accordingly, by adjusting orientations of the side surfaces 72, 74 and the like of the treatment section 54, as illustrated in FIG. 11A to FIG. 11C, the width between the end surfaces 84 can be appropriately adjusted. Consequently, for example, the probes 46 having the treatment sections 54 with the widths Da, Db and Dc are lined up. Accordingly, the probe 46 is selected from the lineup in accordance with the dimension of the opening edge 100a of the bone socket 100 desired to be formed by one operation along the longitudinal axis L.

Figure 12A:
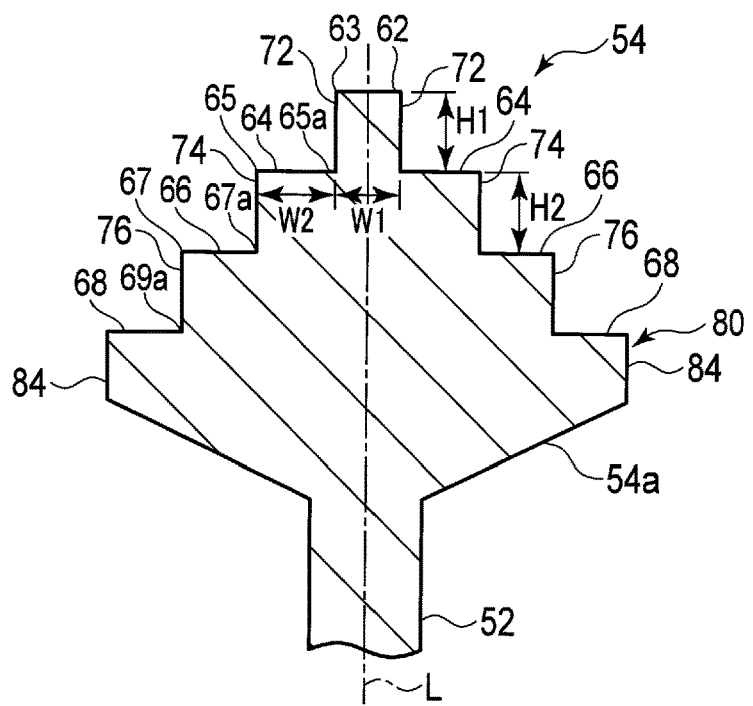
FIG. 12A is an example illustrating a section on an appropriate YX plane of the treatment section illustrated in FIG. 10A.
Figure 12B:
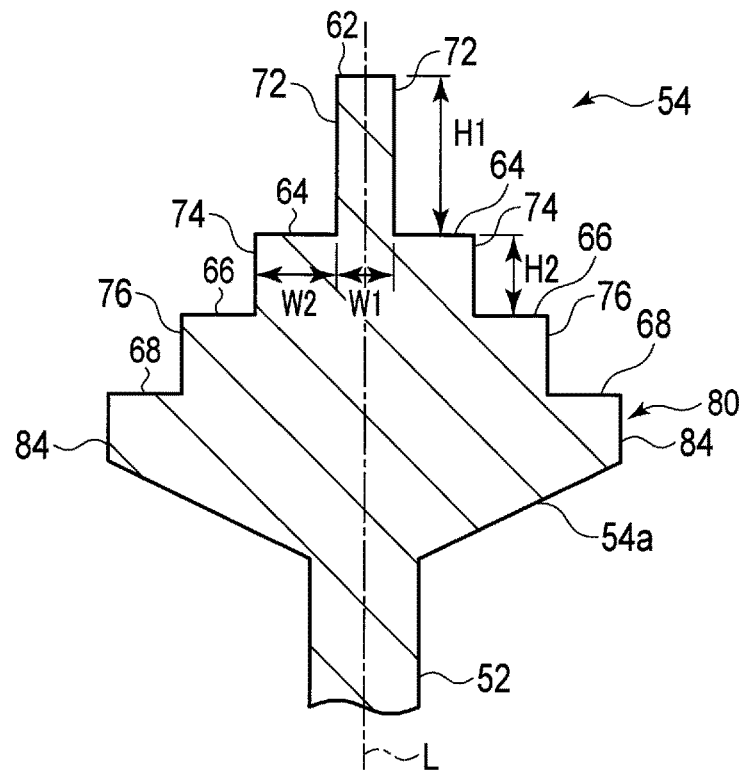
FIG. 12B is an example illustrating a section on an appropriate YX plane of the treatment section illustrated in FIG. 10A, and different from FIG. 12A.

An example of a treatment section 54 having a section illustrated in FIG. 12B shows a case where a first height H1 between a first surface 62 and a second surface 64 is larger than a second height H2 between the second surface 64 and a third surface 66. Consequently, the first height H1 along a longitudinal axis L of a first step (first side surface 72) between the first surface 62 and the second surface 64 is higher than the second height H2 along the longitudinal axis L of a second step (second side surface 74) between the second surface 64 and the third surface 66.

In this case, a distal end of the treatment section 54 is easily observed by observation with the arthroscope 16 from behind in the disposition illustrated in FIG. 1 to the treatment section 54 of a probe 46, though it depends on the positional relationship between the arthroscope 16 illustrated in FIG. 1 and the treatment section 54. When the distal end of the treatment section 54 is observed through the arthroscope 16 in this way, a position and an orientation of the first surface 62 of the treatment section 54 are easily stabilized when a concave bone socket 100 is created with the first surface 62.

A dimension (width) W1 in a Y-axis direction of the first surface 62 is made smaller as compared with a dimension (width) W2 in the Y-axis direction of the second surface 64. Consequently, an initial hole is easily formed in a bone B in a desired position and in a desired orientation by using the treatment section 54. Following the first surface 62, the bone B is cut with the second surfaces 64, and the concave bone socket 100 can be formed in a desired position in a desired direction.

Figure 12C:
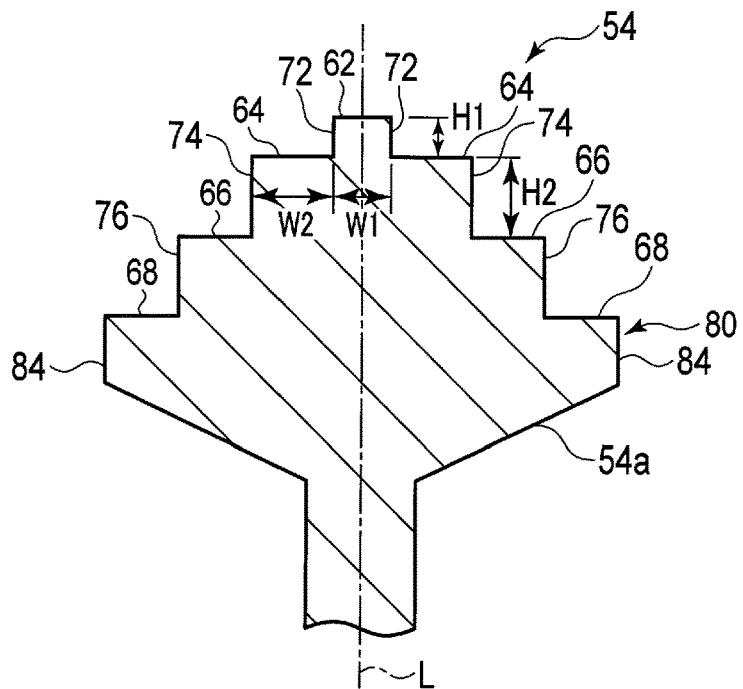
FIG. 12C is an example illustrating a section on an appropriate YX plane of the treatment section illustrated in FIG. 10A, and different from FIG. 12A and FIG. 12B.

An example of a treatment section 54 having a section illustrated in FIG. 12C shows a case where a first height H1 between a first surface 62 and a second surface 64 is smaller than a second height H2 between the second surface 64 and a third surface 66. Consequently, the first height H1 along a longitudinal axis L of a first step between the first surface 62 and the second surface 64 is lower than the second height H2 along the longitudinal axis L of a second step between the second surface 64 and a third surface 66.

Even when the height H1 is smaller as compared with the height H2 in this way, the concave bone socket 100 can be formed appropriately with the first surface 62. Since a protrusion height H1 along the longitudinal axis L of the first surface 62 relative to the second surface 64 is small, durability of the treatment section 54 can be increased.

A dimension (width) W1 in a Y-axis direction of the first surface 62 is made smaller as compared with a dimension (width) W2 in the Y-axis direction of the second surface 64. Consequently, an initial hole can be easily formed in a bone B in a desired position in a desired orientation. Following the first surface 62, the bone B is cut with the second surface 64, and a concave bone socket 100 can be formed in a desired position in a desired orientation.

An example of a treatment section 54 having a section illustrated in FIG. 12A shows a case where a first height H1 between a first surface 62 and a second surface 64, and a second height H2 between the second surface 64 and a third surface 66 are same. Consequently, the first height H1 along a longitudinal axis L of a first step between the first surface 62 and the second surface 64 corresponds to the second height H2 along the longitudinal axis L of a second step between the second surface 64 and the third surface 66.

In this case, by making the protrusion heights H1 and H2 the same, strength of a structure of the treatment section 54 can be kept higher as compared with the case where the height H1 is larger than the height H2. In other words, the treatment section 54 of the structure illustrated in FIG. 12A can keep durability high, even when a reaction force or the like from the bone B is added, for example. Further, in this case, depending on a positional relationship with an arthroscope 16, a distal end of the treatment section 54, that is, a distal end of the first surface 62 is observable through the arthroscope 16. When the distal end of the treatment section 54 is observed through the arthroscope 16 in this way, a position and an orientation of the first surface 62 of the treatment section 54 are easily stabilized when a concave bone socket 100 is created with the first surface 62.

A dimension (width) W1 in a Y-axis direction of the first surface 62 is made smaller as compared with a dimension (width) W2 in the Y-axis direction of the second surface 64. Consequently, an initial hole is easily formed in the bone B in a desired position in a desired orientation by using the treatment section 54. Following the first surface 62, the bone B is cut with the second surfaces 64, and the concave bone socket 100 can be formed in a desired position in a desired orientation.

The structures of the treatment sections 54 illustrated in FIG. 12A to FIG. 12C are appropriately selected depending on whether importance is placed on visibility of the distal end of the treatment section 54 with use of the arthroscope 16, or stability of the structure of the treatment section 54. Accordingly, for example, the probe 46 having the treatment sections 54 in which the height H1 is adjusted is lined up. Accordingly, when importance is placed on disposing the first surface 62 in a suitable orientation and position by using the arthroscope 16, the probe 46 having the treatment section 54 with the large height H1 is selected from the lineup. When importance is placed on stability of the structure of the treatment section 54 such as prevention of unsteadiness or the like of the treatment section 54, rather than disposing the first surface 62 in a suitable orientation and position by using the arthroscope 16, the probe 46 having the treatment section 54 with the small height H1 is selected from the lineup.

The treatment section 54 can be formed by appropriately adjusting the heights H1 and H2 as illustrated in FIG. 12A to FIG. 12C, and appropriately selecting whether or not to make the side surfaces 72, 74 and the like parallel to the longitudinal axis L as illustrated in FIG. 11A to 11C.

As illustrated in FIG. 13A, a first surface 62 is divided into a plurality of portions along an X-axis direction. In this case, an area S1 of the first surface 62 can be formed to be small. For example, a width (dimension) of the first surface 62 can be made small with respect to a width (dimension) of a second surface 64, along a Y-axis direction. Consequently, it is possible to start forming a concave bone socket 100 earlier with the first surface 62. Further, the first side surfaces 72 are formed along end surfaces 82 in the X-axis direction. Consequently, an orientation of the treatment section 54 is easily confirmed with an arthroscope 16 in the disposition illustrated in FIG. 1. Consequently, the first side surfaces 72 along the end surfaces 82 are used to recognize the orientation of the treatment section 54 to a bone B through the arthroscope 16.

A projection shape (inside of an outer edge 63 of the first surface 62) at a time of the first surface 62 being seen from a distal end side to a proximal end side along a longitudinal axis L is smaller than a projection shape (inside of an outer edge 65 of the second surface 64) at a time of the second surface 64 being seen from the distal end side to the proximal end side along the longitudinal axis L. Consequently, the projection shape of the first surface 62 is inside of the outer edge 65 of the second surface 64, is inside of an outer edge 67 of a third surface 66, and is inside of an outer edge (outermost edge 80) of a fourth surface 68. This applies similarly to treatment sections 54 illustrated in FIG. 13B to FIG. 17E.

Note that in an example illustrated in FIG. 13A, a height of the first side surface 72 between the first surface 62 and the second surface 64 is 1 mm, for example. The first surfaces 62 are each formed to be 1 mm×1 mm, for example. Further, the example of the treatment section 54 illustrated in FIG. 13A is formed in four steps having the first surfaces 62 to the fourth surfaces 68.

Figure 13B:
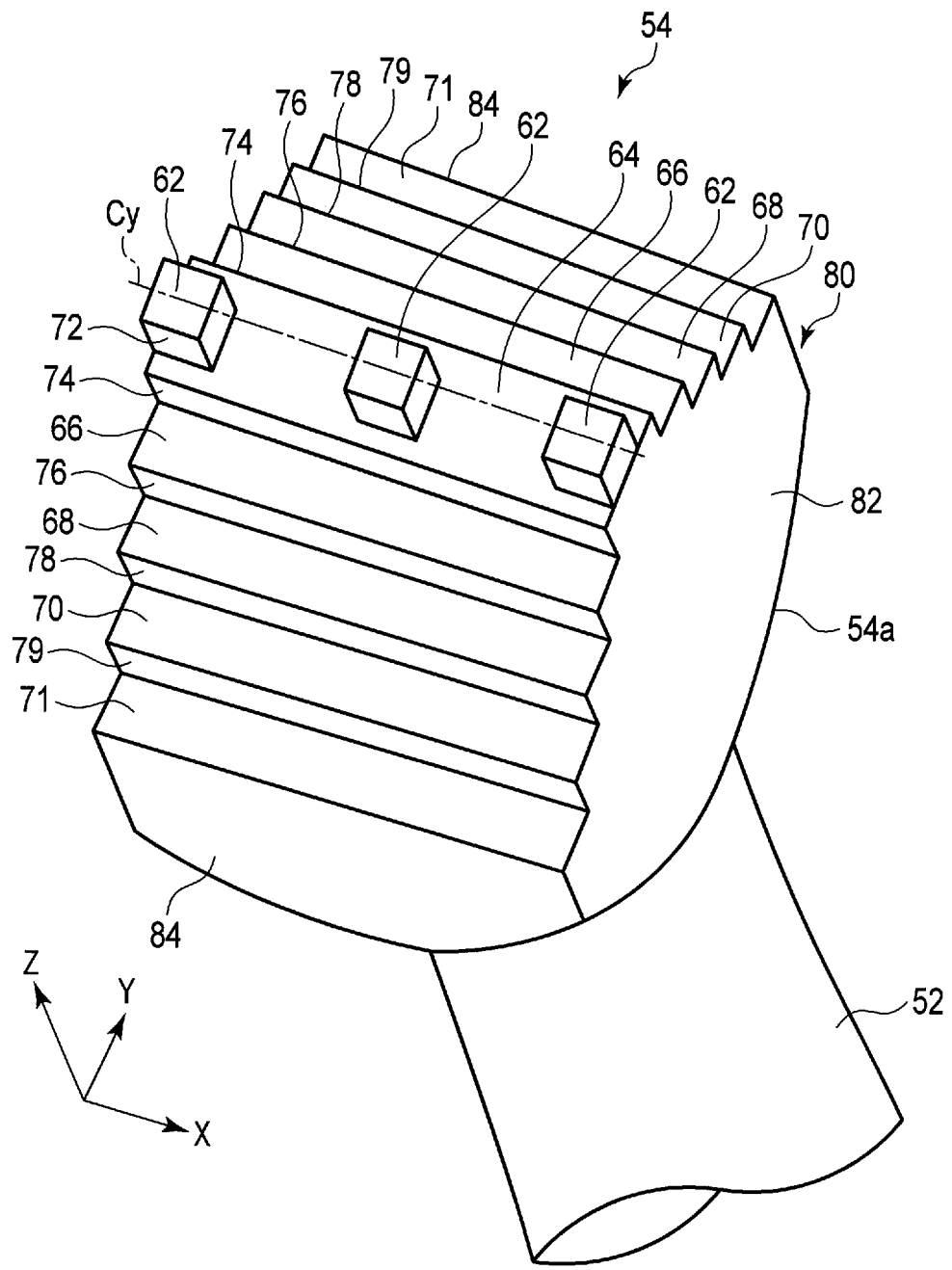
FIG. 13B is a schematic perspective view illustrating a treatment section and a vicinity of the treatment section of an ultrasonic vibration transmittable probe according to an exemplary embodiment.

A treatment section 54 in an example illustrated in FIG. 13B has a larger number of surfaces in the Y-axis direction, and has a larger number of surfaces in a Y-axis direction and a larger number of steps, with respect to the example illustrated in FIG. 13A. A height of the first side surface 72 between the first surface 62 and the second surface 64 is 0.5 mm, for example. The first surfaces 62 are each formed to be 0.5 mm×0.5 mm, for example. Further, the example of the treatment section 54 illustrated in FIG. 13B is formed to be in six steps having the first surfaces 62 to sixth surfaces 71. In a case of the example illustrated in FIG. 13B, heights of the second side surface 74 to a fifth side surface 79 are each formed to be 0.5 mm, for example. By adjusting the heights of the first side surface 72 to the fifth side surface 79, distances in a height direction along the longitudinal axis L such as a distance between the first surface 62 and the second surface 64, a distance between the second surface 64 and a third surface 66, and the like are not increased. Accordingly, it is possible to suppress occurrence of amplitude differences in a direction along the longitudinal axis L in the respective surfaces 62, 64, 66, and the like, not only in the example illustrated in FIG. 13A, but also in the example illustrated in FIG. 13B.

Figure 13C:
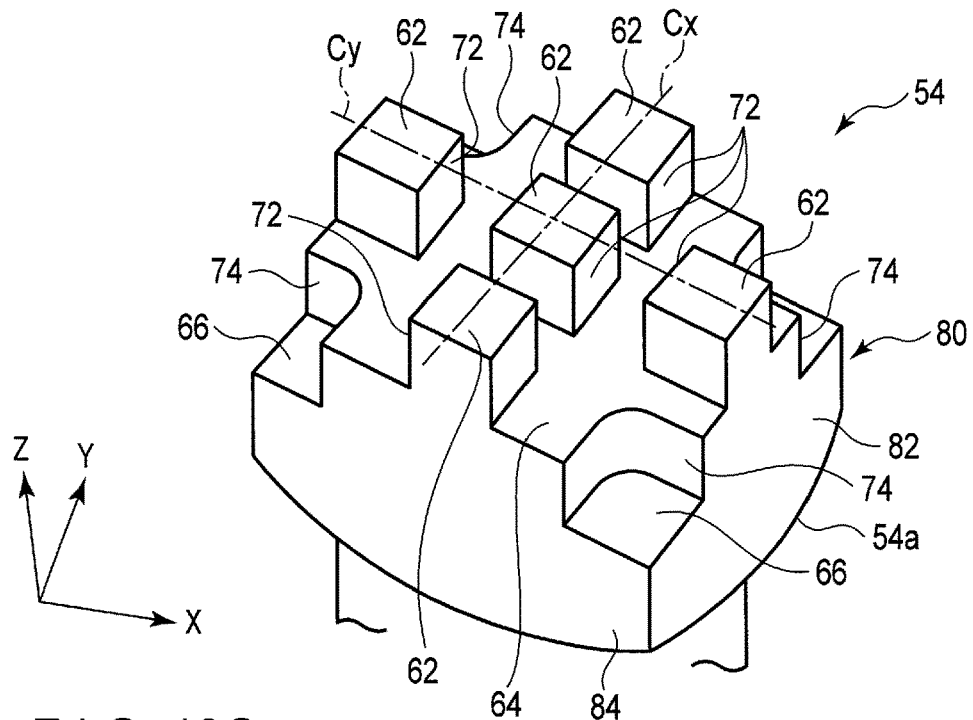
FIG. 13C is a schematic perspective view illustrating a treatment section of an ultrasonic vibration transmittable probe according to an exemplary embodiment.

Note that in the examples illustrated in FIG. 13A and FIG. 13B, the examples where the first surfaces 62 are provided side by side only in the X-direction are described. As illustrated in FIG. 13C, first surfaces 62 are also preferably provided side by side not only in an X-axis direction but also in a Y-axis direction. In FIG. 13C, distal end surfaces are formed as the first surfaces 62. On a second surface 64, first side surfaces 72 protrude to a distal end side with respect to a longitudinal axis L. An outermost edge 80 is formed into a substantially rectangular shape. Third surfaces 66 are formed respectively in corner portions between end surfaces 82 and 84. A treatment section 54 is also preferably formed in this way.

In each of the aforementioned examples, the example is described, in which the surfaces (planes) are formed in the shape of steps along the Y-axis direction, such as the treatment section 54 having the plurality of surfaces (planes) 62, 64, 66 and 68 along the Y-axis direction.

Figure 14A:
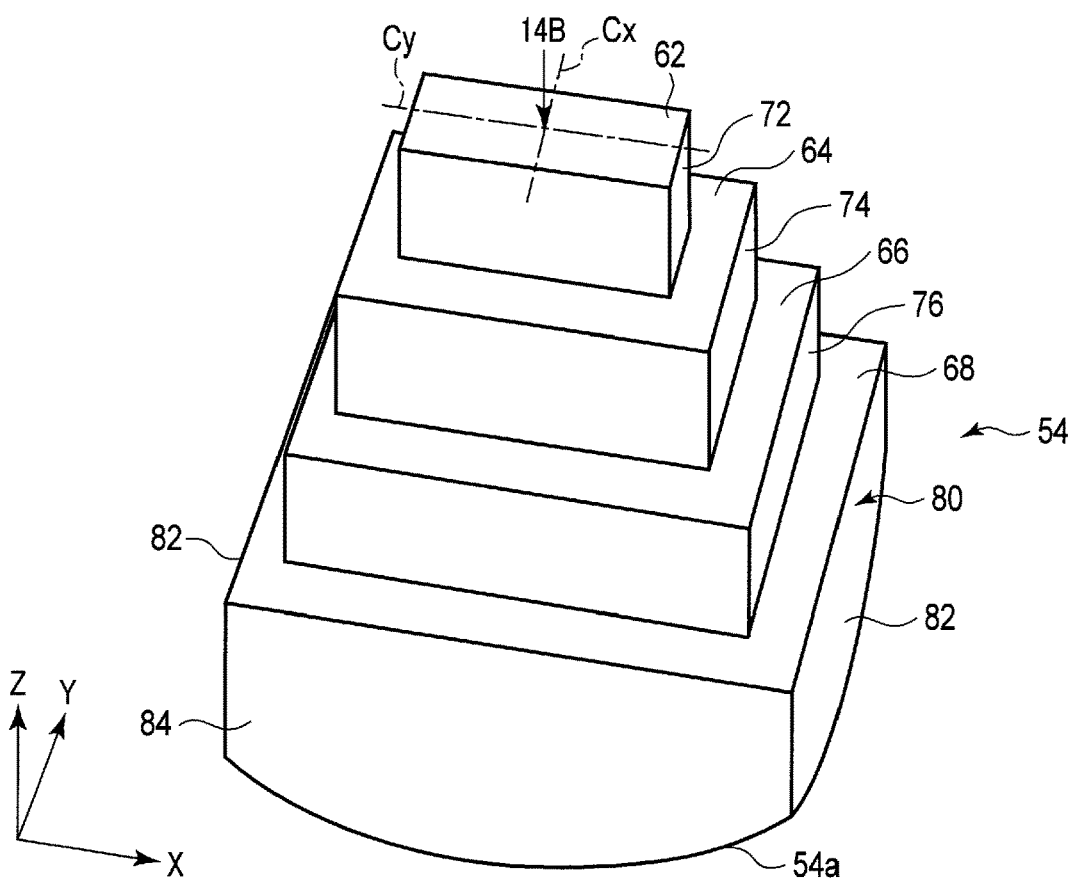
FIG. 14A is a schematic perspective view illustrating a treatment section and a vicinity of the treatment section of an ultrasonic vibration transmittable probe according to an exemplary embodiment.
Figure 14B:
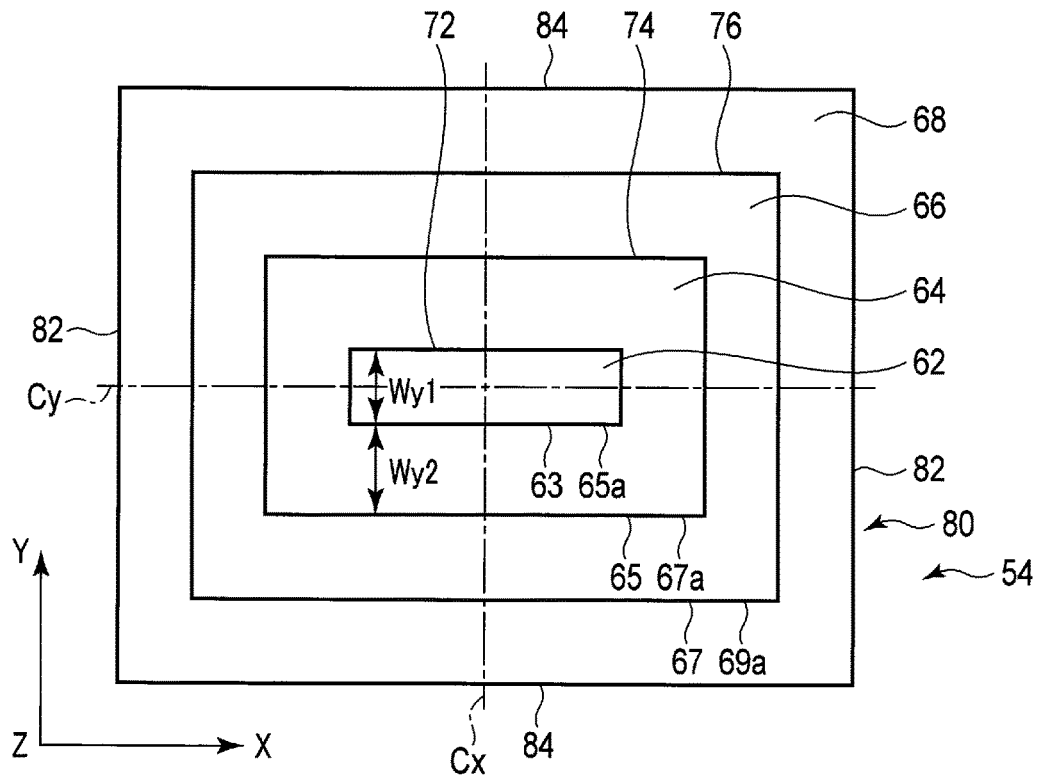
FIG. 14B is a schematic view of the treatment section of the ultrasonic vibration transmittable probe seen from a direction shown by an arrow 14B in FIG. 14A.

Here, as illustrated in FIG. 14A and FIG. 14B, in a treatment section 54, a plurality of surfaces (planes) 62, 64, 66 and 68 are formed in a shape of steps along not only a Y-axis direction but also an X-axis direction. The second surface 64 in the Y-axis direction and the second surface 64 in the X-axis direction continue to each other on a same surface (on an XY plane), and are formed into a loop-shape. Likewise, the third surface 66 in the Y-axis direction and the third surface 66 in the X-axis direction continue to each other on a same surface (on the XY plane), and are formed into a loop-shape. In other words, the treatment section 54 is also preferably formed into a shape of steps such as a substantially pyramid shape.

In the treatment section 54 illustrated in FIG. 14B, a width (dimension) Wy1 in the Y-axis direction of the first surface 62 is smaller as compared with a width (dimension) Wy2 in the Y-axis direction of the second surface 64. By decreasing a contact area of the first surface 62 of the treatment section 54 with a bone B as much as possible along the Y-axis direction, an initial hole is easily formed in the bone B in a desired position in a desired orientation. Following the first surface 62, the bone B is cut with the second surface 64, and a concave bone socket 100 can be formed in a desired position in a desired orientation. In this case, as described in the aforementioned embodiment, a cutting velocity can be improved when the concave bone socket 100 with a desired depth is formed with the treatment section 54 of a probe 46, as compared with the case of cutting the bone B with a distal end surface of an area S of an outermost edge 80 from the beginning.

In the above embodiment, the first surface 62 continues to end surfaces 82 of the outermost edge 80. The first surface 62 of the treatment section 54 of this embodiment does not continue to the end surfaces 82 of the outermost edge 80. Consequently, it is easy to decrease an area S1 of the first surface 62 as compared with the area S1 of the first surface 62 of the treatment section 54 described in the above embodiment. In addition, a velocity at a time of starting forming the concave bone socket 100 with the first surface 62 can be increased more than in the case described in the above embodiment. Consequently, the concave bone socket 100 onto which the first surface 62 is copied with the first surface 62 of the treatment section 54 can be formed earlier to the bone B.

As illustrated in each of FIG. 15A to FIG. 16B, a distal end portion of a treatment section 54 also preferably has only a first surface 62, first side surfaces 72 and a second surface 64. An outer edge of the second surface 64 is formed as an outermost edge 80 of the treatment section 54.

Figure 15A:
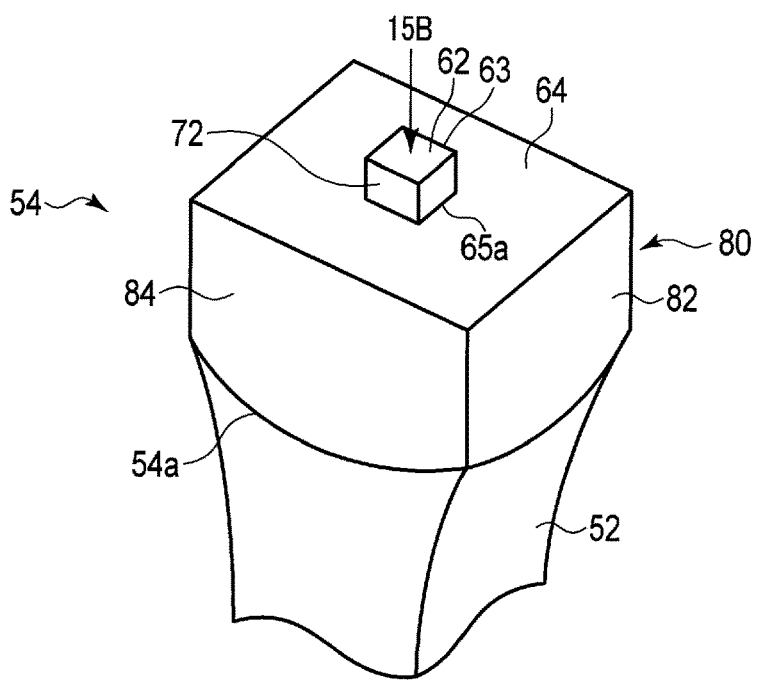
FIG. 15A is a schematic perspective view of a treatment section and a vicinity of the treatment section of an ultrasonic vibration transmittable probe according to an exemplary embodiment.
Figure 15B:
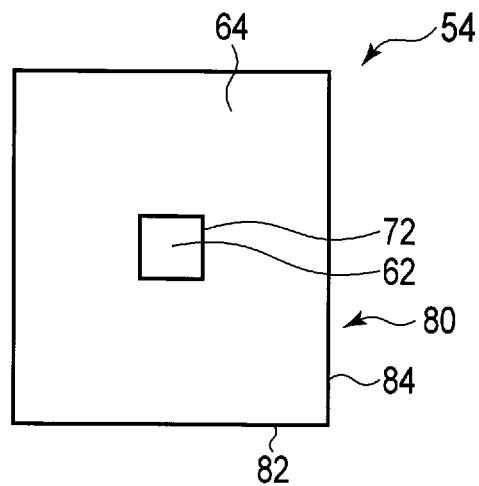
FIG. 15B is a schematic view of the treatment section of the ultrasonic vibration transmittable probe seen from a direction shown by an arrow 15B in FIG. 15A.

In the treatment section 54 illustrated in FIG. 15A and FIG. 15B, an area S1 of the first surface 62 is smaller as compared with an area S2 of the second surface 64. The outermost edge 80 is not limited to a rectangle, but may be a square. In other words, the outermost edge 80 may be in an equilateral polygon. Since the area S1 of the first surface 62 is smaller than the area S2 of the second surface 64, it is easy to start forming a concave bone socket 100. Consequently, the concave bone socket 100 can be formed in a bone B earlier with the first surface 62. A shape of an outer edge 65 of the second surface 64 can be copied as a shape of an opening edge 100a of the concave bone socket 100.

Consequently, in the treatment section 54, a number (number of steps) of surfaces (treatment surfaces) along a longitudinal axis L is not limited to four or six, but may be two.

Here, by decreasing a contact area of the first surface 62 of the treatment section 54 and a bone B respectively along a Y-axis direction and an X-axis direction as much as possible, an initial hole is easily formed in the bone B in a desired position in a desired orientation. Following the first surface 62, the bone B is cut with the second surface 64, and the concave bone socket 100 can be formed in a desired position in a desired orientation. In this case, as described in the aforementioned embodiment, a cutting velocity in a case of forming the concave bone socket 100 with a desired depth with the treatment section 54 of a probe 46 can be improved as compared with the case of cutting the bone B with the distal end surface of the area S, of the outermost edge 80, from the beginning.

Figure 16A:
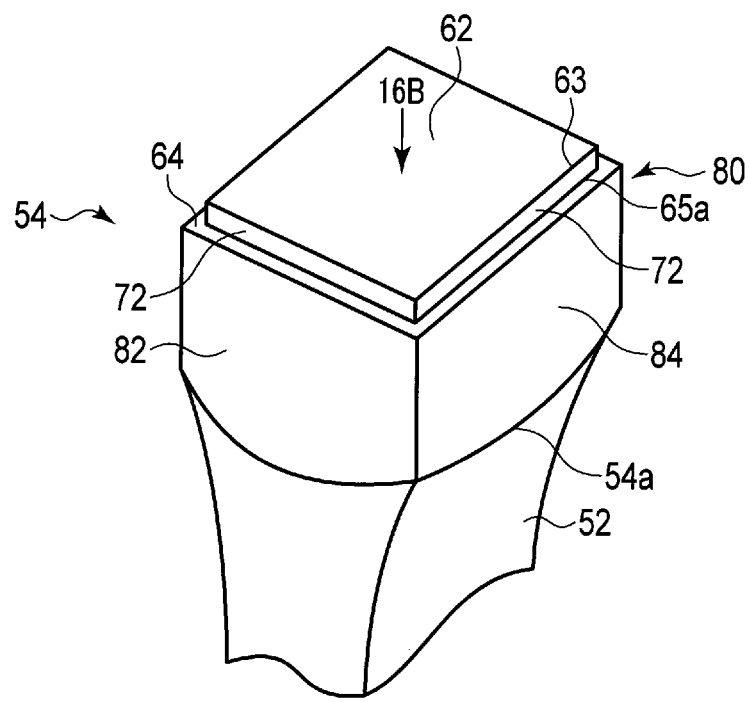
FIG. 16A is a schematic perspective view illustrating a treatment section of an ultrasonic vibration transmittable probe according to an exemplary embodiment and a vicinity of the treatment section.

In a treatment section 54 illustrated in FIG. 16A and FIG. 16B, an area S1 of a first surface 62 is larger as compared with an area S2 of a second surface 64. Although it is conceivable that a cutting velocity in a depth direction with the first surface 62 is lower than in the example illustrated in FIG. 15A and FIG. 15B, a concave bone socket 100 of a large area with a same depth can be formed. A shape of an outer edge 65 of the second surface 64 can be copied as a shape of an opening edge 100a of the concave bone socket 100. In addition, the area S2 of the second surface 64 is decreased, and therefore, a finished surface with the outer edge 65 of the second surface 64, that is, an outermost edge 80 can be made as smooth as possible.

Figure 17B:
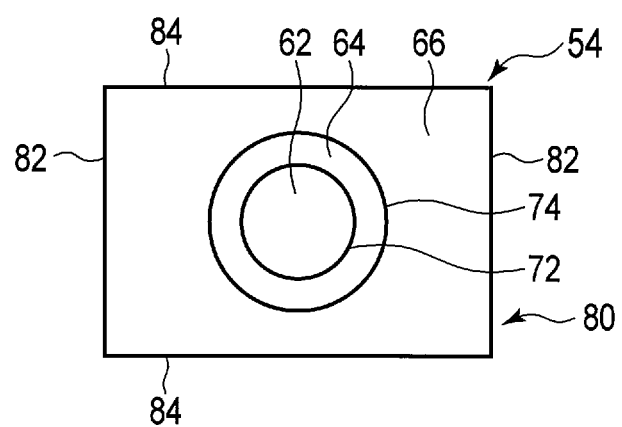
FIG. 17B is a schematic view of the treatment section of the ultrasonic vibration transmittable probe seen from a direction shown by an arrow 17B in FIG. 17A.

A treatment section 54 illustrated in FIG. 17A and FIG. 17B includes a first surface (plane) 62, a second surface (plane) 64, and a third surface (plane) 66. The treatment section 54 in this case includes the three planes 62, 64 and 66, unlike some of the embodiments described above.

In the treatment section 54 illustrated in FIG. 17A and FIG. 17B, the first surface 62 is formed into a circular shape, and the second surface 64 is formed into a ring-shape. An area S1 of the first surface 62 is same or approximately same as an area S2 of the second surface 64. The third surface 66 is formed into a substantially rectangular shape. An area S3 of the third surface 66 is larger than the area S2 of the second surface 64. A shape of an outer edge 67 of the third surface 66 can be copied as a shape of an opening edge 100a of a concave bone socket 100. Even when the treatment section 54 is formed in this way, a surgeon can form a desired concave bone socket 100 by adjusting an orientation of a probe 46 around a longitudinal axis L, based on an image observed through an arthroscope 16.

In the treatment section 54, a number (number of steps) of surfaces (treatment surfaces) along the longitudinal axis L is not limited to four, six or two, but may be three.

Figure 17C:
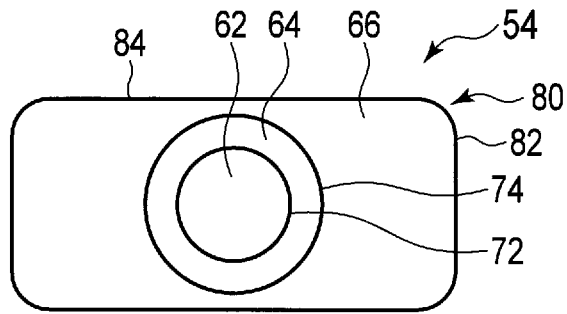
FIG. 17C is a schematic view illustrating a treatment section having an outermost edge different from FIG. 17B.

In a treatment section 54 illustrated in FIG. 17C, corner portions between end surfaces 82 and 84 are each formed as a quarter circle of an appropriate radius, with respect to a sharp state illustrated in FIG. 17B. On the other hand, edges between the third surface 66 and an outermost edge 80 are preferably formed as sharp as possible at right angles.

Figure 17D:
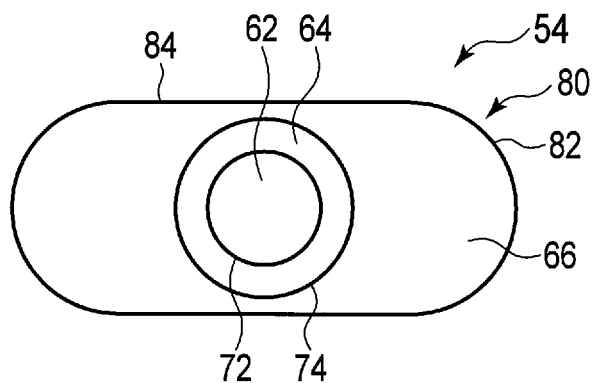
FIG. 17D is a schematic view illustrating a treatment section having an outermost edge different from FIG. 17B and FIG. 17C.
Figure 17E:
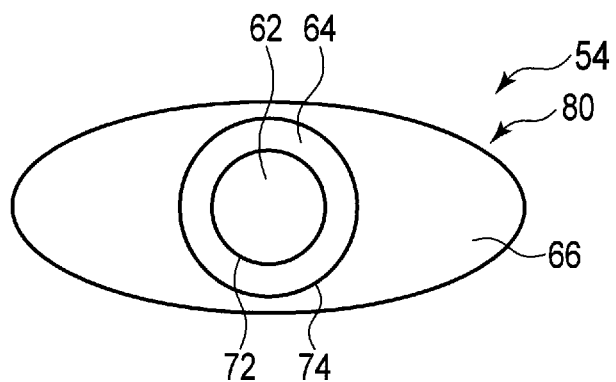
FIG. 17E is a schematic view illustrating a treatment section having an outermost edge different from FIG. 17B to FIG. 17D.

In a treatment section 54 illustrated in FIG. 17D, an outermost edge 80 of the treatment section 54 is schematically formed into a loop shape such as a running track shape in an athletic field that is formed by two long sides and two semicircles, when a proximal end side is seen from a distal end side along a longitudinal axis L. In a treatment section 54 illustrated in FIG. 17E, an outermost edge 80 of the treatment section 54 is formed into a substantially elliptical shape. That is, the outermost edge 80 of the treatment section 54 has an oval shape like an elliptical shape or a running track shape.

In the first surface 62, a part contributing to cutting of a bone B is preferably formed to have a smaller dimension than the second surface 64 along the Y-axis direction (first orthogonal direction) orthogonal to the longitudinal axis L. In this case, by using the treatment sections 54 illustrated in FIG. 17B to FIG. 17E, an initial hole is easily formed in the bone B in a desired position in a desired orientation. Following the first surface 62, the bone B is cut with the second surface 64 and the third surface 66, and a concave bone socket 100 can be formed in a desired position in a desired orientation.

The outermost edge 80 of the treatment section 54 is not limited to a quadrangle, but is formed in an appropriate shape such as a pentagon or a hexagon, or shapes close to these shapes.

The outermost edge (projection shape) 80 of the treatment section 54 of an ultrasonic treatment instrument 22 is formed in an appropriate shape such as a multangular shape, a substantially multangular shape, an elliptical shape, or a substantially elliptical shape. Consequently, when the concave bone sockets 100, 101, 102 and 103 are appropriately formed with the treatment section 54 in accordance with an outer shape of the graft tendon 230 as illustrated in FIG. 9A to FIG. 9E, a space amount between the concave bone sockets 100, 101, 102 and 103, and the graft tendon 230 can be decreased as much as possible, and cut amounts of the femur 112 and the tibia 114 can be decreased.

Figure 18A:
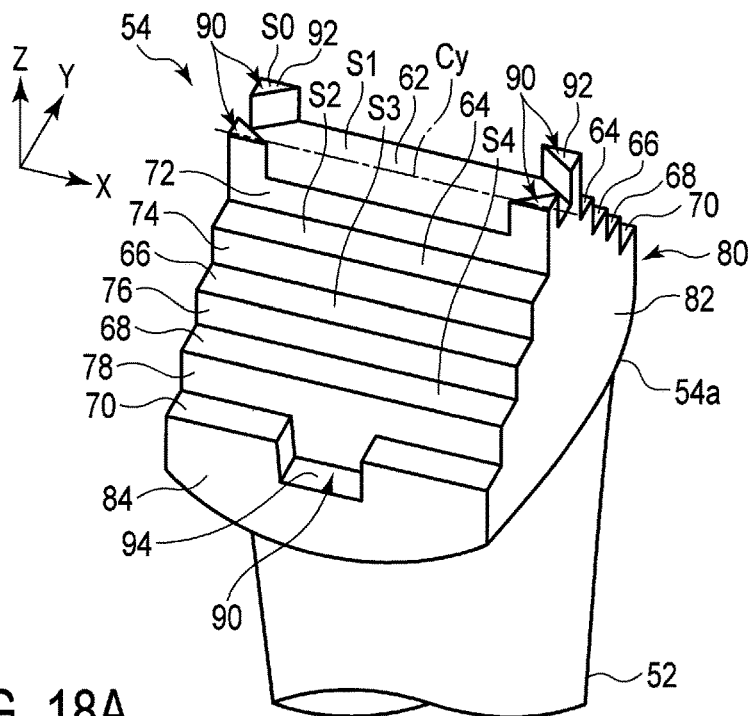
FIG. 18A is a schematic perspective view illustrating a treatment section and a vicinity of the treatment section of an ultrasonic vibration transmittable probe according to an exemplary embodiment.

Another exemplary embodiment will be described by using FIG. 18A and FIG. 18B. This embodiment includes a modified example of the above embodiments. Same members or members having same functions as the members described in the above embodiment are assigned with same reference sings as much as possible, and detailed explanation will be omitted.

The present embodiment can include a modified example of the treatment section 54 illustrated in FIG. 10A. In the present embodiment, as illustrated in FIG. 18A, an example is described, in which a first surface 62 includes indexes 90 that cause a positional relationship between a position where a concave bone socket 100 is to be formed and an orientation of the first surface 62 to be recognized directly before formation of the concave bone socket 100 in a desired position of a bone B.

A projection shape (inside of an outer edge 63 of the first surface 62) at a time of the first surface 62 being seen from a distal end side to a proximal end side along a longitudinal axis L is smaller than a projection shape (inside of an outer edge 65 of a second surface 64) at a time of the second surface 64 being seen from the distal end side to the proximal end side along the longitudinal axis L. Consequently, the projection shape of the first surface 62 is inside of the outer edge 65 of the second surface 64, and inside of an outer edge 67 of a third surface 66, and inside of an outer edge (outermost edge 80) of a fourth surface 68. This applies similarly in treatment sections 54 illustrated in FIG. 19A to FIG. 21B.

The treatment section 54 according to the present embodiment includes the first surface 62, first side surfaces 72, the second surfaces 64, second side surfaces 74, the third surfaces 66, third side surfaces 76, the fourth surfaces 68 and fourth side surfaces 78. The first surface 62, the second surfaces 64, the third surfaces 66 and the fourth surfaces 68 are each formed in a rectangle shape. Consequently, the treatment section 54 is formed in a shape of steps. Note that the first surface 62, the second surfaces 64, the third surfaces 66 and the fourth surfaces 68 extend along an X-axis direction. Widths in a Y-axis direction of the first surface 62, the second surfaces 64, the third surfaces 66 and the fourth surfaces 68 are smaller as compared with widths in the X-axis direction. An area S1 of the first surface 62 is larger than an area S2 of the second surface 64. The area S2 of the second surface 64 and an area S3 of the third surface 66 are same. The area S3 of the third surface 66 and an area S4 of the fourth surface 68 are same.

Note that here, by convex portions 92 described later, distal ends of the convex portions 92 are distal end surfaces, and the first surface 62 is a second surface from a distal end.

The treatment section 54 includes the indexes 90 that are recognized in a field of view of an arthroscope (endoscope) 16 when the distal end side is seen from the proximal end side near the longitudinal axis L. As the indexes 90, the convex portions 92 are formed on the first surface 62. The convex portions 92 protrude to the distal end side along the longitudinal axis L from the first surface 62 in a rectangular shape. The convex portions 92 are formed respectively at four corners in the present embodiment. A protrusion length along the longitudinal axis L, of the convex portion 92 may be approximately same as a height between the first surface 62 and the second surface 64 (refer to FIG. 12A), or the protrusion length of the convex portion 92 may be high or low with respect to the height between the first surface 62 and the second surface 64. A step (first step) exists between the distal end of the convex portion 92, and the first surface 62. The distal end of the convex portion 92 may be orthogonal or approximately orthogonal along the longitudinal axis L, or does not have to be orthogonal or approximately orthogonal. Consequently, the distal end of the convex portion 92 may be in a sharp state. Here, explanation is made, assuming that the distal end of the convex portion 92 has an area S0.

When the proximal end side is seen from the distal end side along the longitudinal axis L, a width (dimension) along the Y-axis direction (first orthogonal direction) orthogonal to the longitudinal axis L, of the convex portion 92 is smaller than a width (dimension) W1 along the Y-axis direction, of the first surface 62.

The index 90 includes a concave portion 94 formed in the fourth surface 68 and along the third side surface 76. Though not illustrated, the concave portion 94 may be formed in only one of the pair of end surfaces 84, or may be formed in both the end surfaces 84.

Figure 18B:
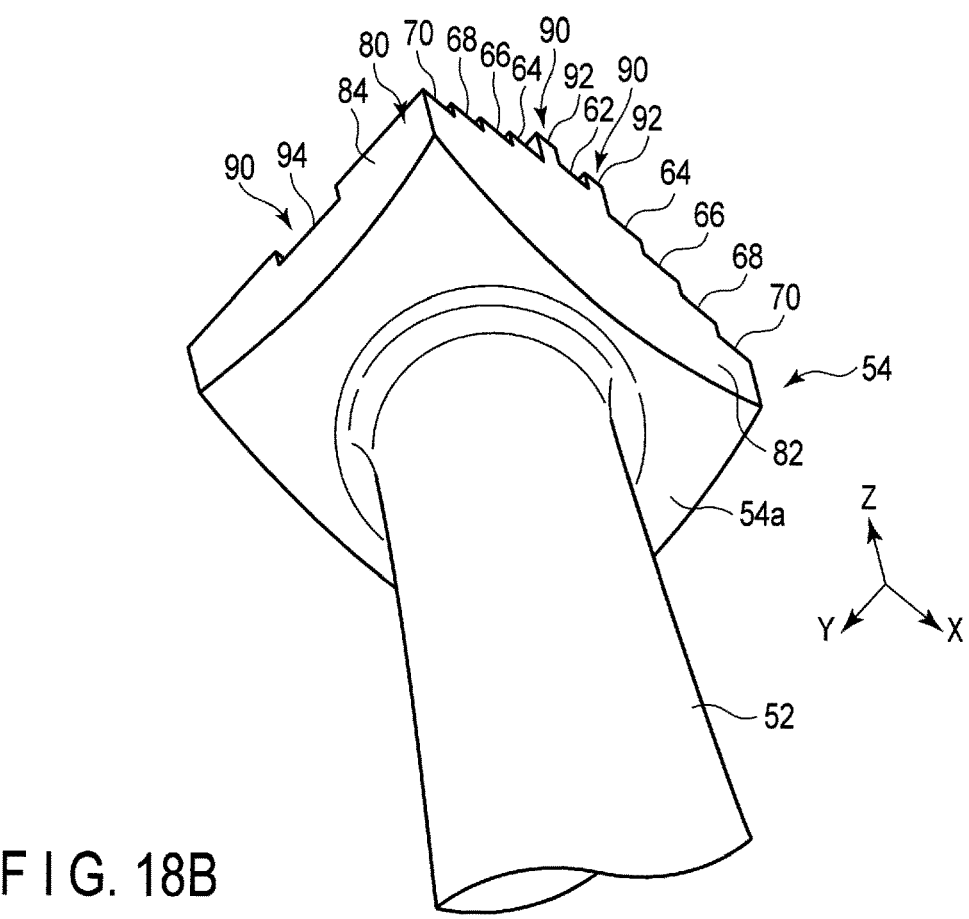
FIG. 18B is a schematic perspective view illustrating a state where the treatment section of the probe illustrated in FIG. 18A is observed by using an arthroscope in a state of a disposition illustrated in FIG. 1.

When an arthroscope 16 and the treatment section 54 of a treatment instrument 22 are disposed in the state illustrated in FIG. 1, the treatment section 54 is recognized by the arthroscope 16 as illustrated in FIG. 18B. Both or one of the convex portion 92 and the concave portion 94 of the index 90 are or is recognized.

At this time, a surgeon can easily recognize an orientation around the longitudinal axis L of the treatment section 54 of an ultrasonic vibration transmittable probe 46 to a bone B. The convex portions 92 are formed on a central line Cy, and therefore, a positional relationship between a center of a bone socket 100 and the central line Cy is easily recognized. Consequently, in a state where the treatment section 54 is disposed in a desired position to the bone B, a concave bone socket 100 can be formed by using ultrasonic vibration.

Further, when crushed debris is continued to be discharged by treatment of forming the concave bone socket 100, crushed debris becomes a hindrance more toward the distal end side of the treatment section 54, and it may be difficult to recognize the distal end side of the treatment section 54. Since the concave portions 94 are formed in the outermost edge 80, the orientation of the treatment section 54 to the bone B is easily recognized, even when the crushed debris is continued to be discharged by the treatment of forming the concave bone socket 100.

The area S0 of the distal end surface of each of the convex portions 92 is smaller than the area S1 of the first surface 62. The convex portions 92 are extended to a distal side along the longitudinal axis L from the four corners of the first surface 62. As in the present embodiment, the contact area of the first surface 62 of the treatment section 54 and the bone B is appropriately decreased, and the concave bone socket 100 is formed with the four convex portions 92, whereby an initial hole is easily formed in the bone B in a desired position in a desired orientation. Consequently, the concave bone socket 100 in the shape of the outer edge 63 of the first surface 62 is easily formed with the four convex portions 92, prior to the first surface 62. Since the four concave bone sockets are formed by the convex portions 92, the concave bone socket 100 can be started being formed by moving the treatment section 54 in the depth direction earlier, in a state where the treatment section 54 hardly causes a positional deviation in a rotation direction with respect to the longitudinal axis L. Accordingly, when the concave bone socket 100 is formed with a plurality of, such as four, convex portions 92, for example, the bone B is cut with the first surface 62 following the convex portions 92, and the concave bone socket 100 can be formed in a desired position in a desired orientation.

The distal end surface of the convex portion 92 is preferably formed as a plane orthogonal to the longitudinal axis L in order to load longitudinal vibration which is transmitted, onto the bone B efficiently. When the area of the distal end surface of the convex portion 92 is decreased as much as possible, the convex portion 92 is required to maintain strength that can cut the bone B (can form the concave bone socket 100) using ultrasonic vibration.

By starting cutting the bone B with the first surface 62, the second surfaces 64, and the third surfaces 66 in this order, the opening edge 100a of the concave bone socket 100 can be expanded into a desired shape.

Further, as described with use of FIG. 11A to FIG. 11C, by forming the surfaces 62, 64, 66 and the like, and the side surfaces 72, 74 and the like, the dimension of the treatment section 54 can be set in accordance with the dimension and the like of the bone socket 100 desired to be formed by one operation along the longitudinal axis L. Consequently, depending on setting of the dimension of the treatment section 54, visibility of the convex portions 92 can be improved.

Further, similarly to what is illustrated in FIG. 12A to FIG. 12C, the protruding amount of the convex portion 92 that protrudes from the first surface 62 is appropriately set. Consequently, depending on setting of the protruding amount of the convex portion 92, visibility of the convex portions 92 can be improved.

Note that in the treatment section 54 in the present embodiment, it is preferable that the first surface 62 to the fourth surfaces 68, and the first side surfaces 72 to the fourth side surfaces 78 are formed in the shapes illustrated, for example, in FIG. 11A to FIG. 12C, as a matter of course.

Another exemplary embodiment can include a modified example of the treatment section 54 illustrated in FIG. 13C. As illustrated in FIG. 19A, in the present embodiment, convex portions 92 are formed on central lines Cx and Cy, and continue to end surfaces 82 and 84. Third surfaces 66 are respectively formed at corner portions between the end surfaces 82 and 84 as concave portions 94 with respect to a second surface 64. In other words, the concave portions 94 are formed across the end surfaces 82 and 84 of an outermost edge 80.

Figure 19B:
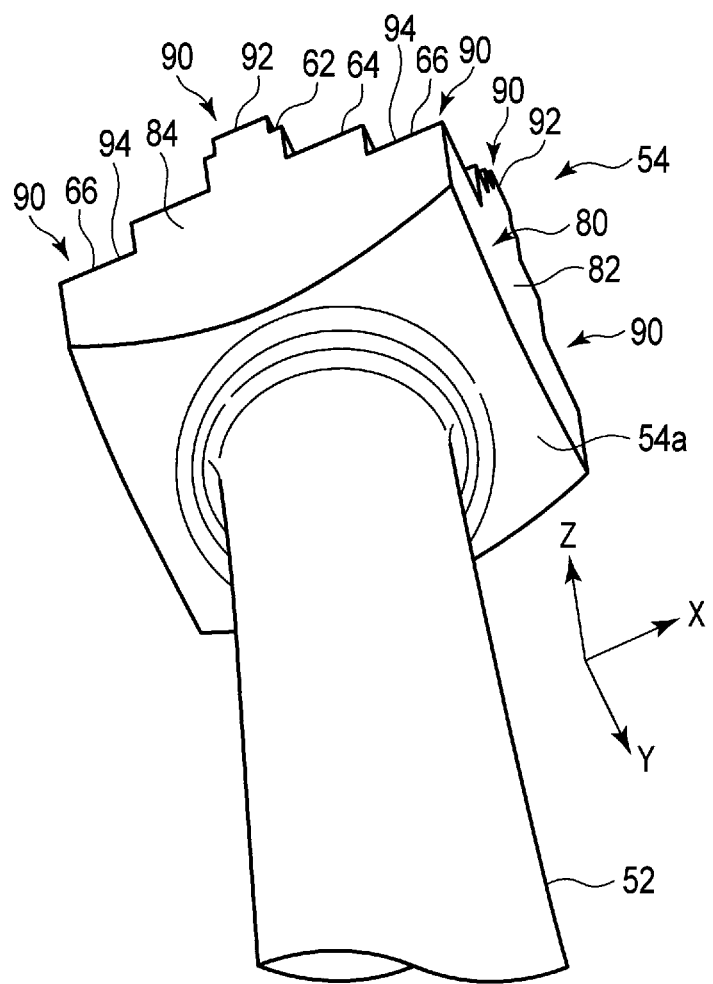
FIG. 19B is a schematic perspective view illustrating a state where the treatment section of the probe illustrated in FIG. 19A is observed by using an arthroscope in the state of the disposition illustrated in FIG. 1.

When an arthroscope 16 and the treatment section 54 of a treatment instrument 22 are disposed in the state illustrated in FIG. 1, the treatment section 54 is recognized by the arthroscope 16 as illustrated in FIG. 19B. Both or one of the convex portion 92 and the concave portion 94 of the index 90 are or is recognized.

At this time, a surgeon can easily recognize an orientation around a longitudinal axis L, of the treatment section 54 of an ultrasonic vibration transmittable probe 46 to a bone B. Since the convex portions 92 are formed on the central lines Cx and Cy, and continue to the end surfaces 82 and 84, a positional relationship of a center of the bone socket 100 and the central lines Cx and Cy is easily recognized. Consequently, a concave bone socket 100 can be formed with use of ultrasonic vibration in a state where the treatment section 54 relative to the bone B is disposed in a desired position.

Since the concave portions 94 are formed on the outermost edge 80, a position of the hole in the bone B which is to be formed, and the orientation of the treatment section 54 are easily recognized.

When the proximal end side is seen from the distal end side along the longitudinal axis L, a width (dimension) along a Y-axis direction (first orthogonal direction) orthogonal to the longitudinal axis L in the convex portion 92 is smaller than a width (dimension) along the Y-axis direction, of the first surface 62. Likewise, a width (dimension) along an X-axis direction (second orthogonal direction) is smaller than a width (dimension) along the X-axis direction, of the first surface 62. An area S0 of a distal end surface of each of the convex portions 92 is smaller than an area S1 of the first surface 62. The convex portions 92 are formed on the Cx and Cy. Four concave bone sockets are formed earlier by the convex portions 92. Consequently, it is possible to start forming the concave bone socket 100 by moving the treatment section 54 in a depth direction along the longitudinal axis L earlier in a state where the treatment section 54 hardly causes a positional deviation in a rotation direction with respect to the longitudinal axis L. Accordingly, when the concave bone socket 100 is formed with a plurality of, for example, four convex portions 92, the bone B is cut with the first surfaces 62, following the convex portions 92, and the concave bone socket 100 can be formed in a desired position in a desired orientation.

Figure 20A:
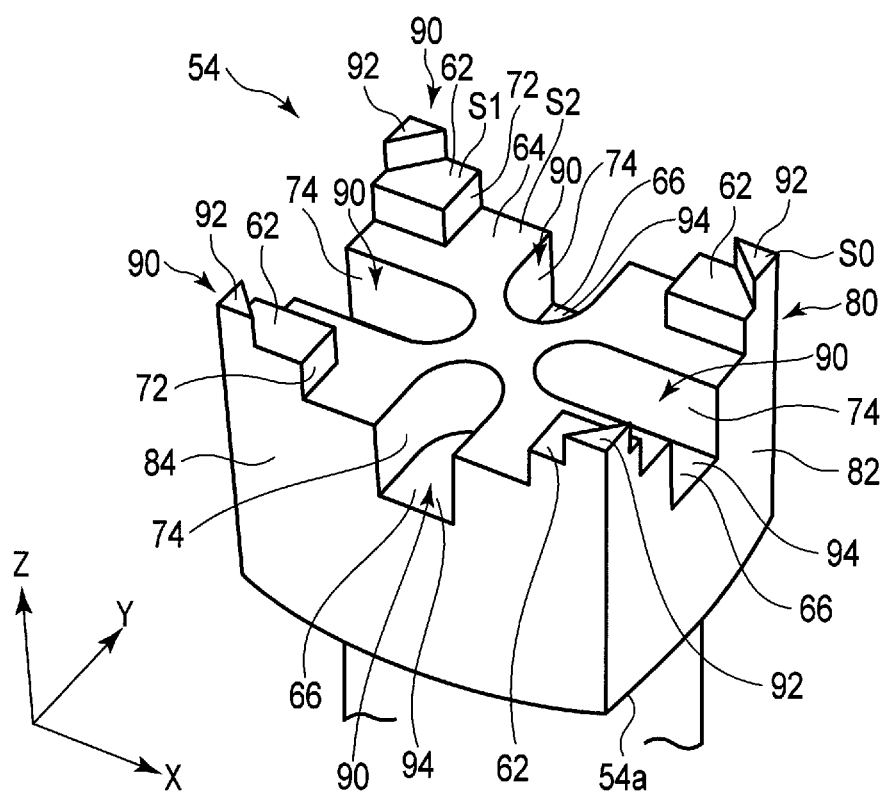
FIG. 20A is a schematic perspective view illustrating a treatment section and a vicinity of the treatment section of an ultrasonic vibration transmittable probe according to an exemplary embodiment.

As illustrated in FIG. 20A, convex portions 92 are provided at four corners of first surfaces 62, and concave portions 94 are formed on central lines Cx and Cy between end surfaces 82 and 84 of an outermost edge 80. Third surfaces 66 are respectively formed on the central lines Cx and Cy between the end surfaces 82 and 84 of the outermost edge 80 as the concave portions 94 to a second surface 64.

Figure 20B:
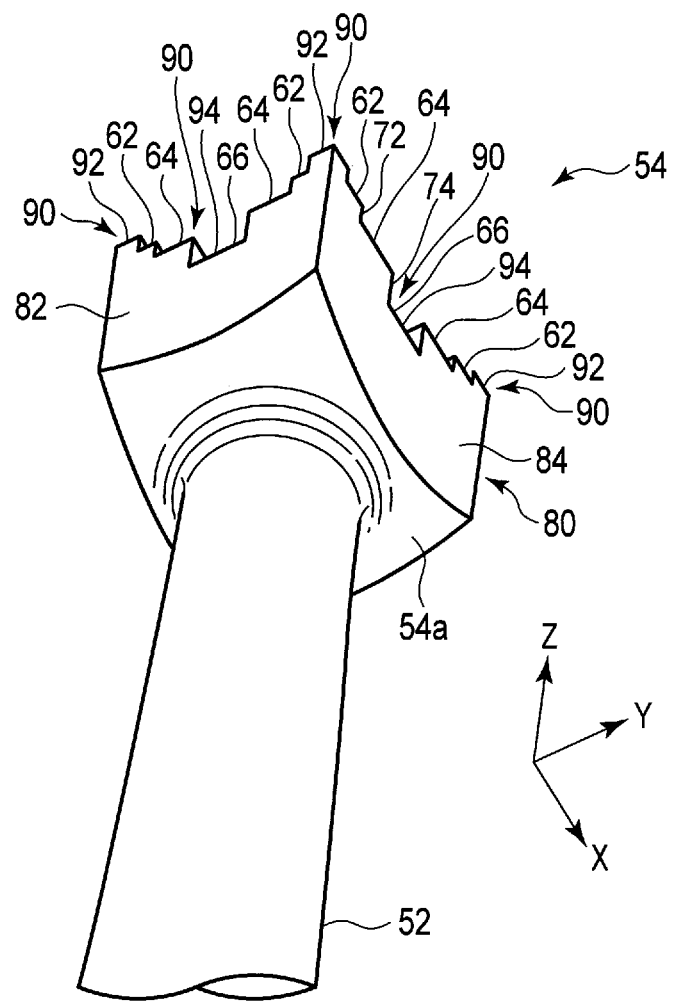
FIG. 20B is a schematic perspective view illustrating a state where the treatment section of the probe illustrated in FIG. 20A is observed by using an arthroscope in the state of the disposition illustrated in FIG. 1.

When an arthroscope 16 and a treatment section 54 of a treatment instrument 22 are disposed in the state illustrated in FIG. 1, the treatment section 54 is recognized by the arthroscope 16 as illustrated in FIG. 20B. Subsequently, both or one of the convex portion 92 and the concave portion 94 of the index 90 are or is recognized.

At this time, a surgeon can easily recognize an orientation around a longitudinal axis L of the treatment section 54 of an ultrasonic vibration transmittable probe 46 to a bone B. Since the convex portions 92 are formed at the corners of the first surfaces 62 and continue to the end surfaces 82 and 84, a positional relationship of a center position of a bone socket 100 desired to be formed, and the convex portions 92 is easily recognized. Consequently, the concave bone socket 100 can be formed with use of ultrasonic vibration in a state where the treatment section 54 to the bone B is disposed in a desired position.

Since the concave portions 94 are formed on the outermost edge 80, a position of the hole of the bone B that is to be formed and the orientation of the treatment section 54 are easily recognized.

When a proximal end side is seen from a distal end side along a longitudinal axis L, a width (dimension) along a Y-axis direction (first orthogonal direction) orthogonal to the longitudinal axis L, of the convex portion 92 is smaller than a width (dimension) along the Y-axis direction, of the first surface 62. Likewise, a width (dimension) along an X-axis direction (second orthogonal direction) is smaller than a width (dimension) along the X-axis direction, of the first surface 62. An area S0 of a distal end surface of each of the convex portions 92 is smaller than an area S1 of the first surface 62. The convex portions 92 are formed at the corners of the first surfaces 62. By the convex portions 92, four concave bone sockets are formed earlier. Consequently, it is possible to start forming the concave bone socket 100 by moving the treatment section 54 in a depth direction along the longitudinal axis L earlier, in a state where the treatment section 54 hardly causes a positional deviation in a rotation direction with respect to the longitudinal axis L. Accordingly, when the concave bone socket 100 is formed with the convex portions 92, the bone B is cut with the first surfaces 62 following the convex portions 92, and the concave bone socket 100 can be formed in a desired position in a desired orientation.

Figure 21A:
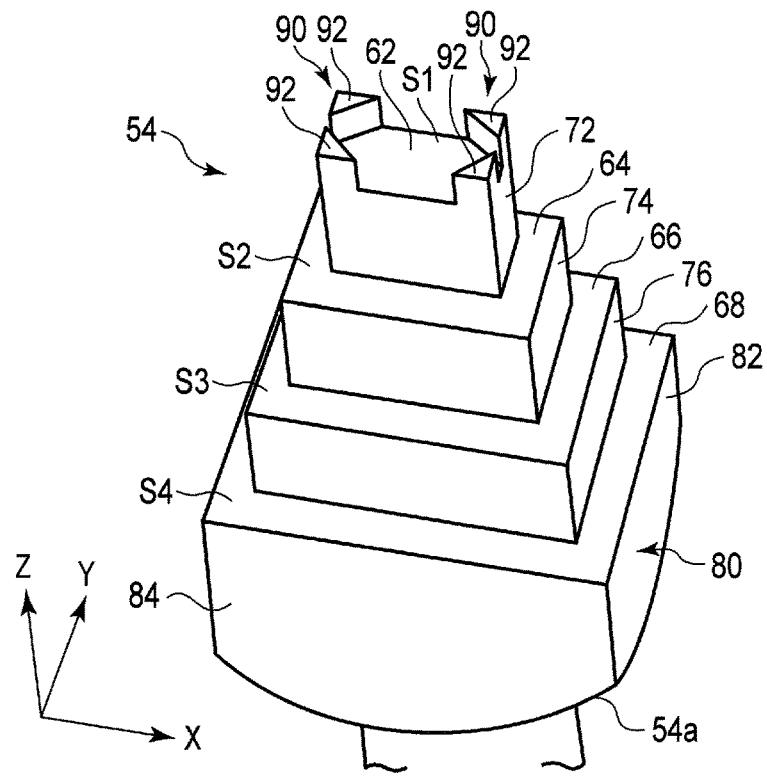
FIG. 21A is a schematic perspective view of a treatment section and a vicinity of the treatment section of an ultrasonic vibration transmittable probe according to an exemplary embodiment.

An exemplary embodiment can include a modified example of the treatment section 54 illustrated in FIG. 14A and FIG. 14B. As illustrated in FIG. 21A, a treatment section 54 is formed in a substantially pyramid shape. A first surface 62 includes convex portions 92. The convex portions 92 are respectively formed at four corners of the first surface 62.

Figure 21B:
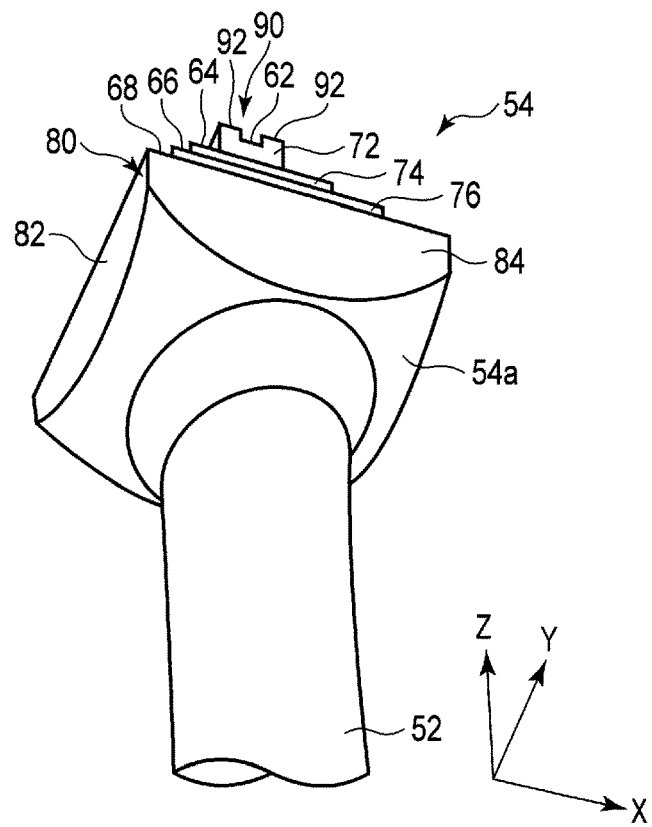
FIG. 21B is a schematic perspective view illustrating a state where the treatment section of the probe illustrated in FIG. 21A is observed by using an arthroscope in the state of the disposition illustrated in FIG. 1.

When an arthroscope 16 and the treatment section 54 of a treatment instrument 22 are disposed in the state illustrated in FIG. 1, the treatment section 54 is recognized by the arthroscope 16 as illustrated in FIG. 21B. The convex portion 92 of an index 90 is recognized.

At this time, a surgeon can easily recognize an orientation around a longitudinal axis L of the treatment section 54 of an ultrasonic vibration transmittable probe 46 to a bone B. The convex portions 92 are formed at corners of the first surface 62, and continue to first side surfaces 72, and therefore, a positional relationship of a position at a center of a bone socket 100 desired to be formed, and the convex portions 92 is easily recognized. Consequently, the concave bone socket 100 can be formed with use of ultrasonic vibration in a state where the treatment section 54 to the bone B is disposed in a desired position.

An area S0 of a distal end surface of each of the convex portions 92 is smaller than an area S1 of the first surface 62. The convex portions 92 are formed at the corners of the first surface 62. Four concave bone sockets are formed earlier by the convex portions 92. Consequently, it is possible to start forming the concave bone socket 100 by moving the treatment section 54 in a depth direction along a longitudinal axis L earlier, in a state where the treatment section 54 hardly causes a positional deviation in a rotation direction with respect to the longitudinal axis L.

Accordingly, in the examples illustrated in FIG. 18A to FIG. 21B, the orientations of the treatment sections 54 of the treatment instruments 22 to the positions where the bone sockets 100 are desired to be formed, of the bones B can be easily matched with appropriate states under the arthroscope 16.

Further, when the convex portion 92 as the index 90 is included, initial cutting is performed, and the treatment section 54 can be prevented from slipping with respect to the bone B. Consequently, according to the present embodiment, it is possible to provide the ultrasonic vibration transmittable probe and the ultrasonic treatment assembly capable of improving treatment efficiency in a case of forming a hole in bone, for example.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic vibration transmittable probe comprising:
a probe body configured to transmit ultrasonic vibration generated by an ultrasonic transducer from a proximal end side to a distal end side along a longitudinal axis of the probe body;
an ultrasonic transducer connector provided on the proximal end side of the probe body and configured to connect the ultrasonic transducer; and a treatment section provided on the distal end side of the probe body and configured to cut a treatment object with the ultrasonic vibration, the treatment section comprising:
- a first cutting surface orthogonal to or approximately orthogonal to the longitudinal axis;
- a second cutting surface proximal of the first cutting surface and orthogonal to or approximately orthogonal to the longitudinal axis, a first step being provided between the first cutting surface and the second cutting surface; and
- a third cutting surface proximal of the second cutting surface and orthogonal to or approximately orthogonal to the longitudinal axis, a second step being provided between the second cutting surface and the third cutting surface; and
- an index configured to be recognized in a field of view of an endoscope when seen from the proximal end side to the distal end side, the index being formed by a protruding portion that protrudes from the first cutting surface in a distal direction along the longitudinal axis,
- wherein the index is formed at an outermost edge of the treatment section that defines a largest outer perimeter of the treatment section formed around the longitudinal axis, and
- wherein a portion of the first cutting surface has a dimension along a first orthogonal direction that is smaller than a dimension of the second cutting surface along the first orthogonal direction, the first orthogonal direction being orthogonal to the longitudinal axis.

2. The ultrasonic vibration transmittable probe according to claim 1, wherein
   an area of the first cutting surface is smaller than an area of the second cutting surface.

3. The ultrasonic vibration transmittable probe according to claim 1, wherein the first cutting surface is planar and includes a boundary defined by a first edge portion.

4. The ultrasonic vibration transmittable probe according to claim 3, wherein a surface parallel to the longitudinal axis is provided between the first edge portion of the first cutting surface and the second cutting surface.

5. The ultrasonic vibration transmittable probe according to claim 1, wherein the second cutting surface is planar and includes a boundary defined by a second edge portion spaced from the longitudinal axis.

6. The ultrasonic vibration transmittable probe according to claim 1, wherein when the treatment section is seen from the distal end side to the proximal end side along the longitudinal axis, at least part of the second cutting surface is exposed.

7. The ultrasonic vibration transmittable probe according to claim 1, wherein a first height of the first step along the longitudinal axis is equal to or greater than a second height of the second step along the longitudinal axis.

8. The ultrasonic vibration transmittable probe according to claim 1, wherein a first height of the first step along the longitudinal axis is equal to or less than a second height of the second step along the longitudinal axis.

9. The ultrasonic vibration transmittable probe according to claim 1, wherein the outermost edge of the treatment section defining the largest outer perimeter of the treatment section formed around the longitudinal axis has a multangular shape or an oval shape.

10. The ultrasonic vibration transmittable probe according to claim 1, wherein a dimension of the first cutting surface along the first orthogonal direction partly varies among positions in a second orthogonal direction which is orthogonal to the longitudinal axis and the first orthogonal direction.

11. The ultrasonic vibration transmittable probe according to claim 1, wherein a proximal end portion of the treatment section is formed so that an area of a cross section orthogonal to the longitudinal axis becomes smaller toward the proximal end side along the longitudinal axis.

12. The ultrasonic vibration transmittable probe according to claim 1, further comprising a support section supported by a handle and provided at a node position of the ultrasonic vibration of when the ultrasonic vibration is transmitted to the probe body.

13. An ultrasonic treatment assembly comprising:
- an ultrasonic transducer configured to generate ultrasonic vibration in response to a power supply; and
- an ultrasonic vibration transmittable probe coupled to the ultrasonic transducer, the ultrasonic vibration transmittable probe comprising:
- a probe body configured to transmit the ultrasonic vibration generated by the ultrasonic transducer from a proximal end side to a distal end side along a longitudinal axis of the probe body;
- an ultrasonic transducer connector provided on the proximal end side of the probe body and configured to connect the ultrasonic transducer;
- a treatment section provided on the distal end side of the probe body and configured to cut a treatment object with the ultrasonic vibration, the treatment section comprising:
- a first cutting surface orthogonal to or approximately orthogonal to the longitudinal axis;
- a second cutting surface proximal of the first cutting surface and orthogonal to or approximately orthogonal to the longitudinal axis, a first step being provided between the first cutting surface and the second cutting surface; and
- a third cutting surface proximal of the second cutting surface and orthogonal to or approximately orthogonal to the longitudinal axis, a second step being provided between the second cutting surface and the third cutting surface; and
- an index configured to be recognized in a field of view of an endoscope when seen from the proximal end side to the distal end side, the index being formed by a protruding portion that protrudes from the first cutting surface in a distal direction along the longitudinal axis,
- wherein the index is formed at an outermost edge of the treatment section that defines a largest outer perimeter of the treatment section formed around the longitudinal axis, and
- wherein a portion the first cutting surface has a dimension along a first orthogonal direction that is smaller than a dimension of the second cutting surface along the first orthogonal direction, the first orthogonal direction being orthogonal to the longitudinal axis.

* * * * *